United States Patent
Kousteni

(10) Patent No.: US 9,717,727 B2
(45) Date of Patent: Aug. 1, 2017

(54) METHODS OF TREATING AND PREVENTING LEUKEMIA AND OTHER CANCERS OF THE BLOOD AND BONE

(71) Applicant: The Trustees of Columbia University in the City of New York, New York, NY (US)

(72) Inventor: Stavroula Kousteni, Glen Ridge, NJ (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 167 days.

(21) Appl. No.: 14/355,355

(22) PCT Filed: Nov. 16, 2012

(86) PCT No.: PCT/US2012/065458
§ 371 (c)(1),
(2) Date: Apr. 30, 2014

(87) PCT Pub. No.: WO2013/074889
PCT Pub. Date: May 23, 2013

(65) Prior Publication Data
US 2014/0303197 A1    Oct. 9, 2014

Related U.S. Application Data

(60) Provisional application No. 61/560,934, filed on Nov. 17, 2011.

(51) Int. Cl.
*A61K 31/505* (2006.01)

(52) U.S. Cl.
CPC ............... *A61K 31/505* (2013.01)

(58) Field of Classification Search
CPC .................................. A61K 31/505
See application file for complete search history.

(56) References Cited

U.S. PATENT DOCUMENTS

2006/0039903 A1    2/2006  Jameson et al.

OTHER PUBLICATIONS

Camilleri et al (Neurogastroenterol Motil. Mar. 2011 ; 23(3): 193-200).*
Sprynski et al (Leukemia (2010) 24, 1940-1950).*
Yang et al (Cell Biochem Funct 2010; 28: 334-341).*
Andrews et al. (1990) Canadian Journal of Physiology and Pharmacology 68:325.
Berger, Gray, and Roth (2009) Annual Review of Medicine 60:355.
Bundgaard, H. (1992) Advanced Drug Delivery Review 8:1.
(Continued)

*Primary Examiner* — Savitha Rao
*Assistant Examiner* — Angela Brown-Pettigrew
(74) *Attorney, Agent, or Firm* — Leason Ellis LLP

(57) ABSTRACT

The present invention relates to preventing and treating leukemia and other cancers of the blood and bone, as well as disorders of the blood, by inhibiting gut-derived serotonin. The inhibition of the gut-derived serotonin is accomplished by inhibiting Tph1, an enzyme responsible for the production of gut-derived serotonin. The present invention also relates to preventing and treating leukemia and other cancers of the blood and bone, as well as disorders of the blood, by increasing the number, growth and proliferation of osteoblasts.

12 Claims, 41 Drawing Sheets

(56) References Cited

OTHER PUBLICATIONS

Castillo and Jacobs (2010) Current Osteoporosis Reports 8:98.
Calvi et al. (2003) Nature 425:841.
Chan et al. (2009) Nature 457:490.
Christopherson et al. (2005) Cell 120:421.
Côté et al. (2003) Proceedings of the National Academy of Sciences, US 100:13525.
Dennis, J. E. and Charbord, P. (2002) Stem Cells 20: 205.
Frisch et al. (2012) Blood 119:540.
Gershon and Tuck (2007) Gastroenterology 132:397.
Gershon (2005) Journal of Clinical Gastroenterology 39:S184.
Gong, J. K. (1978) Science 199:I443.
Huse et al. (1989) Science 246:1275.
Inose et al. (2011) Journal of Bone and Mineral Research 26:2002.
Iwamoto et al. (2007) J Clin Invest. 117:1049.
Kim et al. (2008) Blood 112:4628.
Kode et al. (2012) J Clin. Invest 122: 3490.
Kulke and Mayer (1999) New England Journal of Medicine 340:858.
The Leukemia and Lymphoma Society, Facts 2010-2011.
Levesque, J. P., Helwani, F. M., and Winkler, I. G. (2010) Leukemia 24:1979.
Liu et al. (2008) The Journal of Pharmacology and Experimental Therapeutics 325:47.
Mayack, S. R. and Wagers, A. J. (2008) Blood 112:519.
Mendez-Ferrer et al. (2010) Nature 466:829.
Miyamoto et al. (2011) J Exp. Med. 208:2175.
Moellering et al. (2009) Nature 462:182.
Morse et al. (2002) Blood 100246.
Oh, I. H. and Kwon, K. R. (2010) Stem Cells 28:1243.
Park et al. (2012) Cell Stem Cell 10:259.
Patel et al. (2004) Biological Psychiatry 55:428.
Raaijmakers et al. (2010) Nature 464:852.
Serafeim et al. (2003) Blood 101: 3212.
Taichman et al. (1996) Blood 87:518.
Taichman, R. S. and Emerson, S. G. (1994) J. Exp. Med. 179:1677.
Visnjic et al. (2004) Blood 103:3258.
Wakley at al. (2007) Cell 129:097.
Wu et al. (2008) Proc. Natl. Acad. Sci. U. S. A 105:16976.
Xie et al. (2005) Bioorganic & Medicinal Chemistry Letters 15:3267.
Yadav et al., Pharmacological inhibition of gut-derived serotonin synthesis is a potential bone anabolic treatment for osteoporosis. Nat. Med., Mar. 2010, vol. 16, No. 3, p. 308-312; Especially Abstract, p. 309, col. 1.
Yadav et al. (2008) Cell 135:825.
Yoshikawa et al. (2011) J Bone Miner. Res. 26:2012.
Zhang et al. (2003) Nature 425:836.
Zhu et al. (2007) Blood 109:3706.
Alpini et al. Serotonin Metabolism Is Dysregulated in Cholangiocarcinoma, Which Has Implications for Tumor Growth. Cancer Res., Nov. 15, 2008, vol. 68, No. 22; pp. 9184-9193. Especially Abstract, p. 9188, p. 9191.
Tefferi et al., Selective serotonin reuptake inhibitors are effective in the treatment of polycythemia vera-associated pruritus. Blood, Apr. 1, 2002, vol. 99, No. 7; p. 2627. Especially Abstract.
Nocito et al., Serotonin Regulates Macrophage-Mediated Angiogenesis in a Mouse Model of Colon Cancer Allografts; Cancer Res., Jul. 1, 2008, vol. 68, No. 13, p. 5152-5158. Especially p. 5153, col. 2; Fig. 1A.
Kang et al., A multigenic program mediating breast cancer metastasis to bone. Cancer Cell, Jun. 2003, vol. 3, No. 6, p. 537-549. Especially Abstract.
Parfitt Michael A,. et al. "Bone Histomorphometry: Standardization of Nomenclature, Symbols, and Units." Journal of Bone and Mineral Research 2.6 (1987): 595-610.

\* cited by examiner

|  | WT | Leukemic mice |
|---|---|---|
| BV/TV (%) | 15.4 ± 0.6 | 13.0 ± 0.1 * |
| N.Ob/T.Ar (mm⁻¹) | 52.8 ± 7.2 | 17.5 ± 4.9 * |
| BFR (μm³/μm²/Year) | 70.4 ± 9.8 | 33.8 ± 9.6 * |
| Oc.S/B.S | 5.3 ± 0.8 | 5.0 ± 0.1 |

| | WT | Leukemic mice |
|---|---|---|
| BV/TV (%) | 18.3 ± 0.7 | 12.0 ± 0.8 * |
| N.Ob/T.Ar (mm⁻¹) | 92.6 ± 11.9 | 24.1 ± 6.0 * |
| Oc.S/B.S | ± | ± |

| | Wild Type | DTA$_{osb}$ |
|---|---|---|
| BV/TV (%) | 16.6 ± 1.0 | 12.0 ± 0.5* |
| Nb.Ob/T.Ar. (mm$^{-1}$) | 68.2 ± 7.9 | 35.8 ± 9.9* |
| OcS/BS | 8.0 ± 1.8 | 7.7 ± 1.3 |

\* $p<0.05$

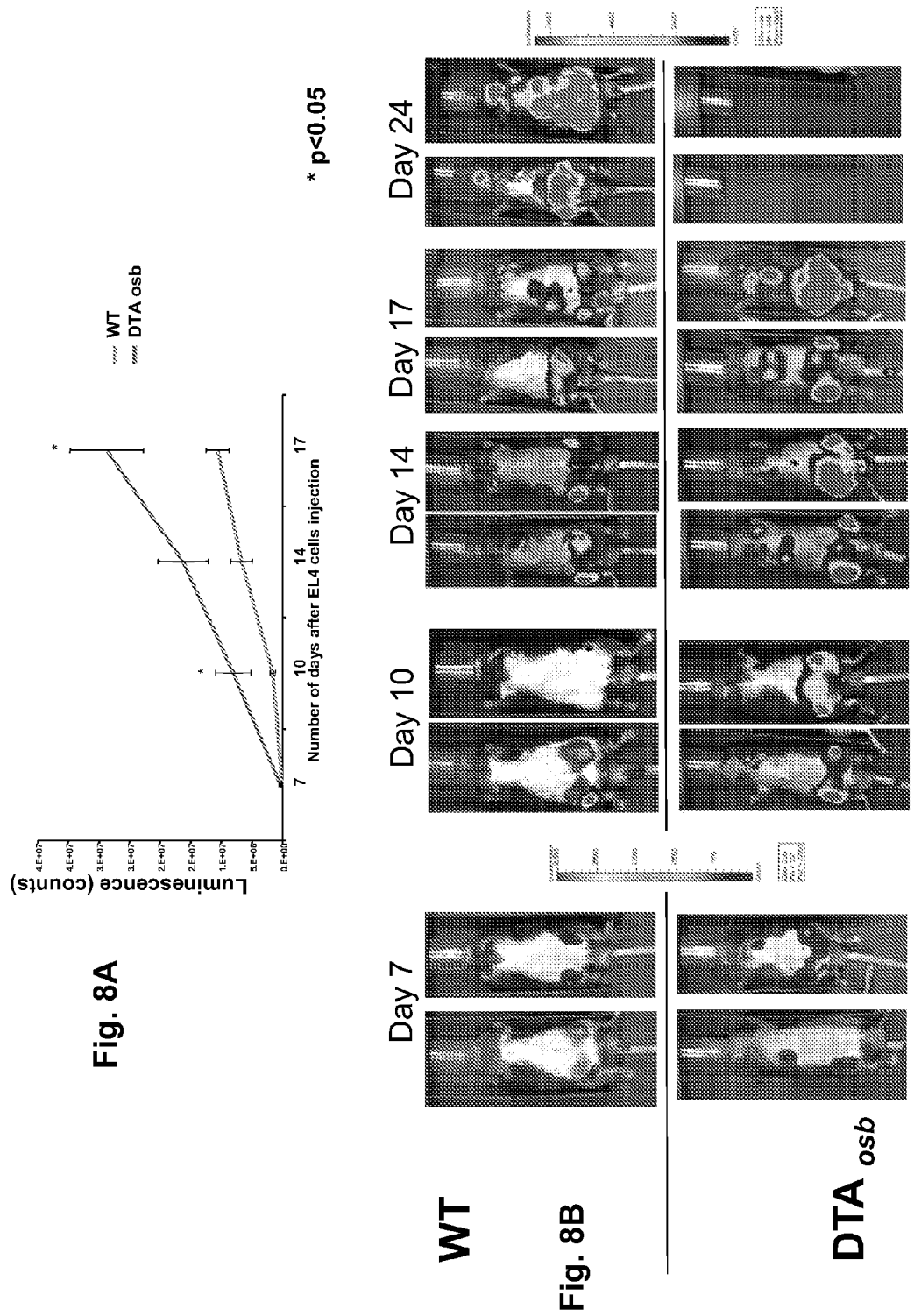

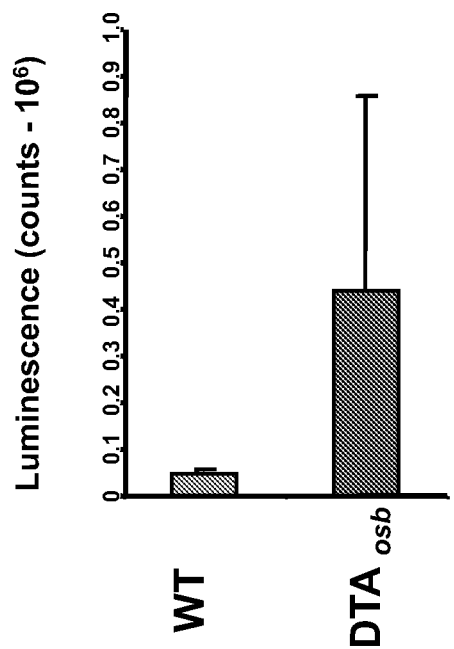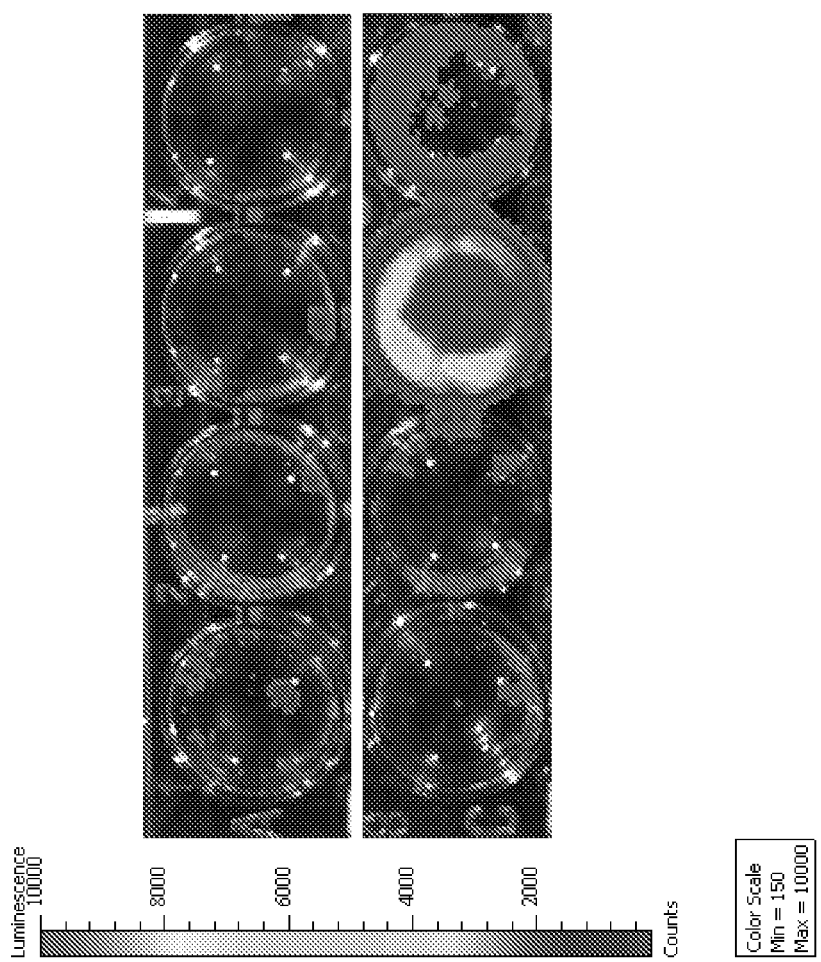
Fig. 9B
Fig. 9A

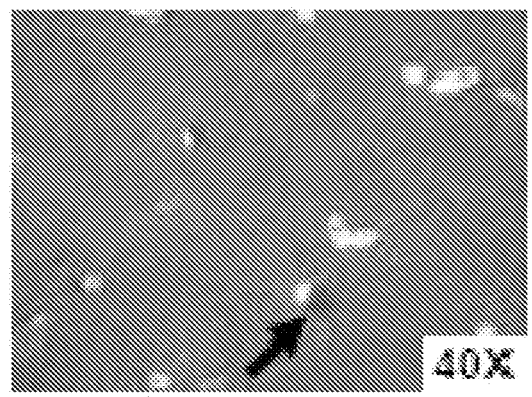
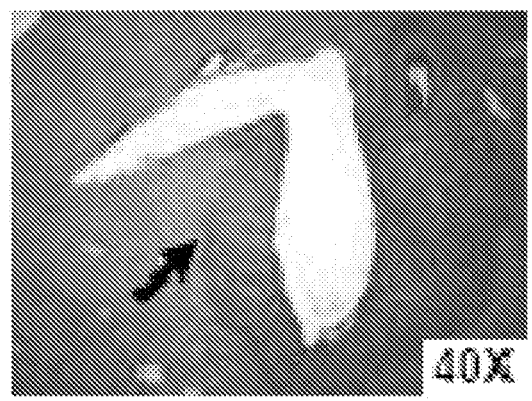
Fig. 12

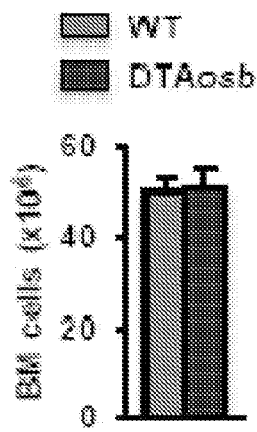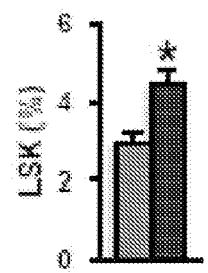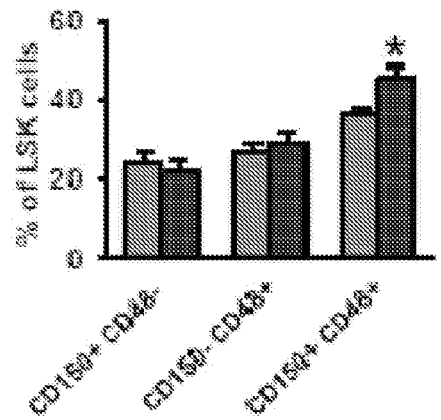
Fig. 15A  Fig. 15B  Fig. 15C
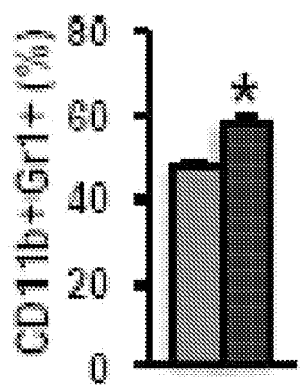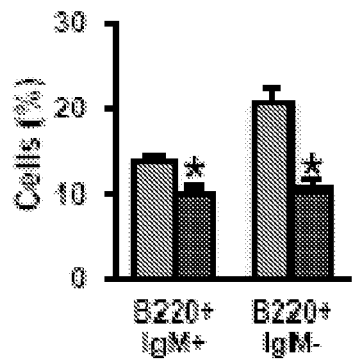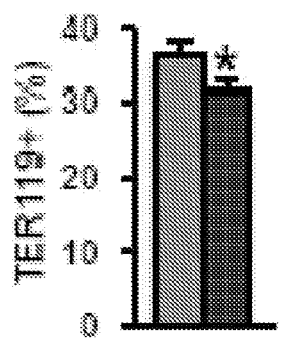
Fig. 15D  Fig. 15E  Fig. 15F
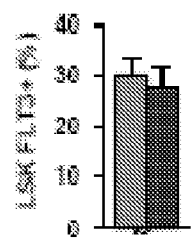
Fig. 15G

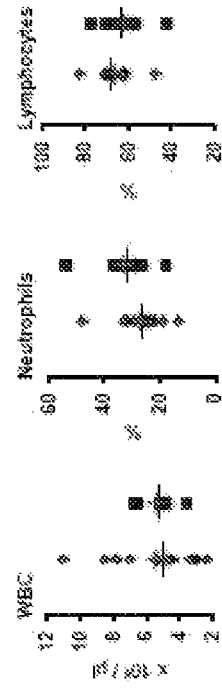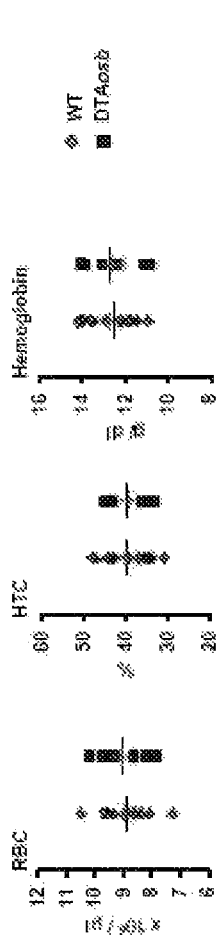
Fig. 16A Fig. 16B Fig. 16C Fig. 16D Fig. 16E Fig. 16F Fig. 16G

| | WT Vehicle | WT LP533401 | Leukemia Vehicle | Leukemia LP533401 |
|---|---|---|---|---|
| BV/TV (%) | 17.6 ± 1.1 | 21.8 ± 0.2 * | 14.1 ± 1.4 | 16.7 ± 0.8 * |
| N.Ob/T.Ar (mm⁻¹) | 73.5 ± 6.6 | 104.7 ± 2.4 * | 23.1 ± 4.7 ** | 55.0 ± 11.7 ** |
| BFR (μm³/μm²/Year) | 66.0 ± 14.3 | 60.7 ± 7.0 | NA | NA |
| Oc.S/B.S | 10.5 ± 2.6 | 12.1 ± 1.5 | 9.5 ± 1.0 | 10.8 ± 1.8 |

Fig. 24A
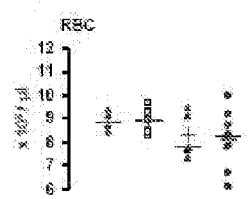
Fig. 24B
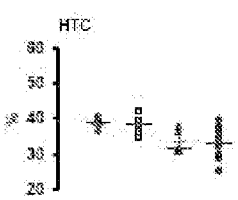
Fig. 24C
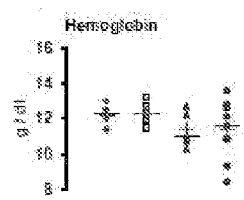
Fig. 24D
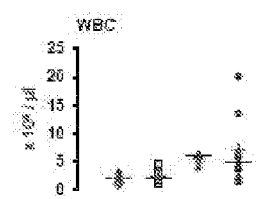
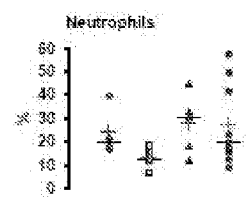
Fig. 24E
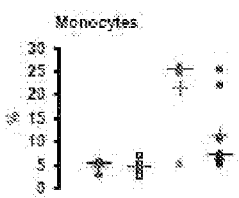
Fig. 24F
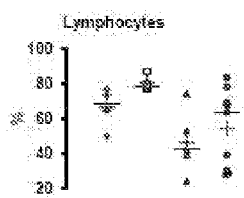
Fig. 24G

|  | WT Vehicle | Leukemia Vehicle | Leukemia LP533401 |
|---|---|---|---|
| BV/TV (%) | 18.2 ± 0.9 | 15.0 ± 1.2 * | 17.8 ± 0.9 * |
| N.Ob/T.Ar (mm⁻¹) | 117.3 ± 10.1 | 44.2 ± 9.2 * | 102.3 ± 11.5 * |
| BFR (μm³/μm²/Year) | 103.1 ± 17.7 | 54.0 ± 15.3 | 86.0 ± 16.8 |
| Oc.S/B.S | 9.4 ± 1.1 | 10.8 ± 2.7 | 12.2 ± 1.7 |

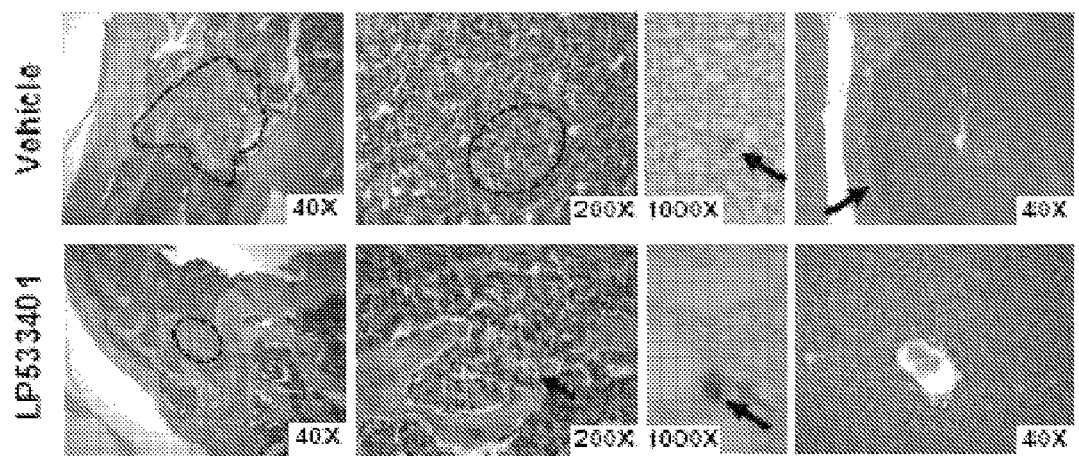

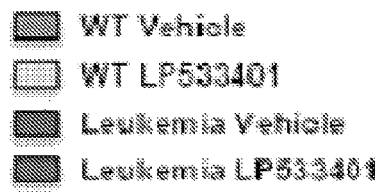
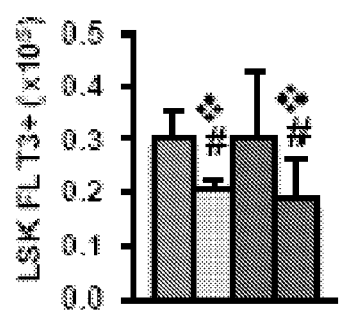
Fig. 32A
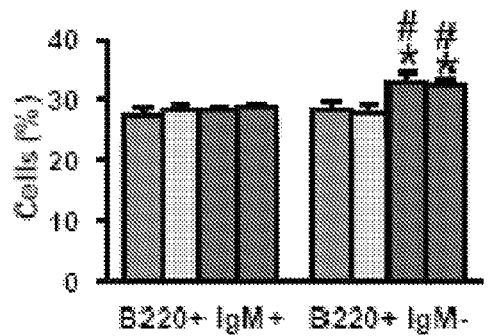
Fig. 32B
Fig. 32C
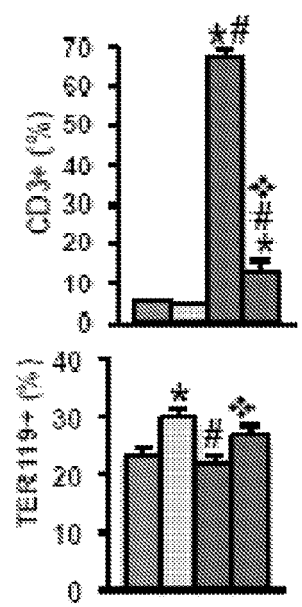
Fig. 32D
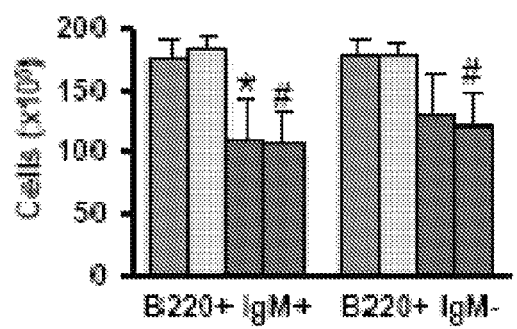
Fig. 32E Fig. 34A   Fig. 34B   Fig. 34C
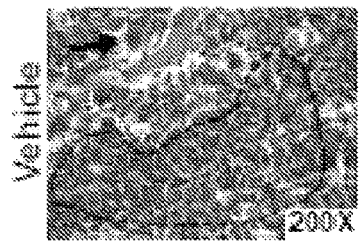
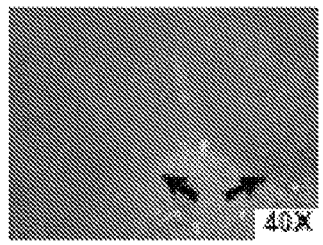
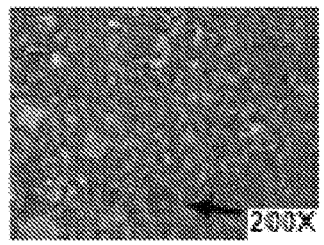
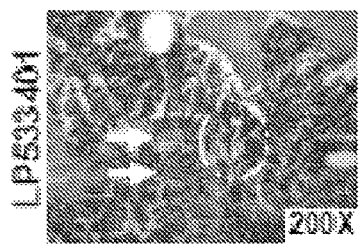
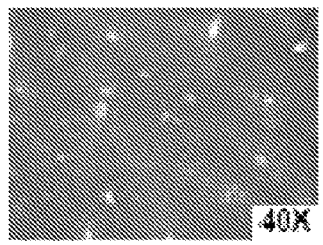
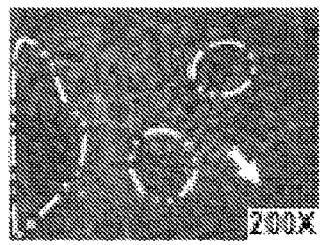
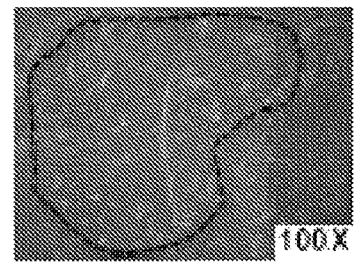
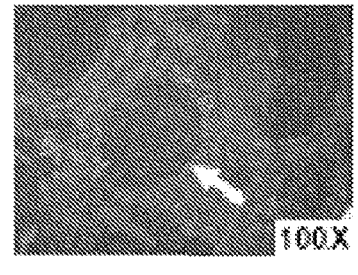
Fig. 34D   Fig. 34E

|  | WT Vehicle | WT LP533401 | Leukemia Vehicle | Leukemia LP533401 |
|---|---|---|---|---|
| BV/TV (%) | 15.7 ± 1.0 | 17.3 ± 0.8 | 12.2 ± 1.4 ** | 16.0 ± 0.5 * |
| N.Ob/T.Ar (mm⁻¹) | 71.4 ± 5.9 | 86.3 ± 6.7 | 39.6 ± 2.2 ** | 77.5 ± 5.5 ** |
| BFR (μm³/μm²/Year) | ± | ± | ± | ± |
| Oc.S/B.S | 4.3 ± 0.7 | 4.7 ± 0.7 | 5.1 ± 1.1 | 5.4 ± 0.8 |

METHODS OF TREATING AND PREVENTING LEUKEMIA AND OTHER CANCERS OF THE BLOOD AND BONE

CROSS REFERENCE TO RELATED APPLICATION

The present application claims priority to U.S. patent application Ser. No. 61/560,934 filed Nov. 17, 2011, which is hereby incorporated by reference in its entirety.

This invention was made with government support under AG032959 awarded by NIH. The government has certain rights in the invention.

FIELD OF THE INVENTION

This invention is in the field of preventing and treating leukemia and other cancers, especially those of the blood and bone, as well as other disorders of the blood, by increasing osteoblast proliferation, preferably by inhibiting serotonin.

BACKGROUND OF THE INVENTION

Hematopoiesis is the normal formation of blood cells in the bone marrow. Blood cells develop from pluripotential hematopoietic stem cells. The first step in the hematopoietic differentiation process is the commitment of the stem cell to one of two large pathways: myeloid or lymphoid. A myeloid stem cell then matures into a myeloid blast. This blast can form red blood cells, platelets or several types of white blood cells. A lymphoid stem cell matures into a lymphoid blast, which forms into one of several types of white blood cells, such as B cells or T cells. Most blood cells mature in the bone marrow and then move into the blood vessels. Hematopoiesis takes place in a region termed the bone marrow niche. In addition to hematopoietic stem cells, endothelial cells, stromal cells, adipocytes, fibroblasts, and bone cells are found in this niche.

It has long been appreciated that trabecular bone formation and establishment of hematopoiesis within the bone marrow cavity are intimately coordinated (Dennis and Charbord (2002)). Osteoblasts, the bone forming cells, in particular, are in close contact with hematopoietic stem cells, and have been highlighted as a defining component of the hematopoietic stem cell niche controlling the homing and development of neighboring hematopoietic stem cells (HSCs) (Raaijmakers et al. (2010); Castillo and Jacobs (2010); Levesque, Helwani, and Winkler (2010); Dennis and Charbord (2002)). Primitive hematopoietic cells in the bone marrow and implanted lineage-negative HSCs localize adjacent to the endosteal surface where osteoblasts reside, whereas rarely cycling HSCs sporadically attach to endosteal osteoblasts (Oh and Kwon (2010); Gong (1978)). In addition, a functional interaction between the two cell types involving engagement of the Notch1/Jag1 signaling pathway between HSCs and osteoblasts, promotes HSC proliferation (Calvi et al. (2003); Zhang et al. (2003)). Transgenic and knockout mouse models have indicated parallel, concordant alterations in osteoblast precursor numbers or mesenchymal cells of the osteolineage, and the number of long term repopulating HSCs (LT-HSCs), as well as subsequent defects in bone marrow hematopoiesis and the development of extramedullar hematopoiesis (Mendez-Ferrer et al. (2010); Wu et al. (2008); Visnjic et al. (2004); Calvi et al. (2003); Zhang et al. (2003)). Genetic evidence has now lent support to the idea that osteoblast progenitors or mesenchymal stem cells (MSCs) with osteoblastic capability are implicated in HSC mobilization and lineage determination survival and proliferation (Mendez-Ferrer et al. (2010); Wu et al. (2008); Mayack and Wagers (2008); Zhu et al. (2007); Taichman et al. (1996); Taichman and Emerson (1994)).

In a more precise manner of regulation, the information received by HSCs seems to be influenced by the differentiation stage of the osteoblast. Nestin-expressing cells of the mesenchymal osteolineage affect homing of HSC progenitors to the bone marrow (Mendez-Ferrer et al. (2010)). Osterix-expressing early osteoblast progenitors initiate ectopic HSC niche formation and regulate B lymphopoiesis (Chan et al. (2009); Wu et al. (2008)). In contrast, osteoclasts, the bone resorbing cells, appear to be dispensable for the maintenance and mobilization of HSCs (Miyamoto et al. (2011)).

The mechanisms by which osteoblasts influence hematopoiesis are just now being deciphered. Osteoblast-induced increases in HSCs and selective expansion of the erythroid lineage can be cause by elevated HIF/EPO signaling in osteoblasts. Osteoblasts also support B lymphocyte commitment and differentiation from hematopoietic stem cells (Zhu et al. 2007). However, little is known about the role of osteoblasts in hematologic diseases.

Irregular hematopoiesis can lead to numerous conditions including cancers of the blood, such as leukemia, lymphoma, and myeloma, and myelodysplastic syndromes. In these patients, the abnormal hematopoiesis leads to the generation of high numbers of abnormal, or cancerous, cells. The accumulation of these irregular cells in the marrow, blood and/or lymphatic tissue interferes with the production and functioning of normal red cells, white cells and platelets (The Leukemia and Lymphoma Society, Facts 2010-2011, page 3). Additionally, irregular hematopoiesis can cause other disorders of the blood.

Every ten minutes, someone in the United States dies from a blood cancer. There will be an estimated 54,020 deaths from leukemia, lymphoma, and myeloma this year. In 2010, it was estimated that 43,050 people would be diagnosed with leukemia, and 21,840 people would die of the disease. Moreover, leukemia causes about one-third of all cancer deaths in children younger than 15 years (The Leukemia and Lymphoma Society, Facts 2010-2011, page 1).

While there are several known treatments for blood cancers, including chemotherapy, radiation, immunotherapy, gene therapy, and stem cell transplantation, there is still a poor prognosis. In patients who are 65 years or older (65 is the median age at diagnosis), survival rates following chemotherapy are in the range of 10%. In younger patients, the survival rate is in the range of 30%, except in the very small fraction of patients. Various modifications of drug delivery and dose have had no significant impact. Additionally, all of these therapies have many unwanted side effects. Chemotherapy can cause extreme fatigue, hair loss, nausea, loss of appetite, and greater risks of infection. Radiation can cause extreme fatigue. Immunotherapy can cause headache, muscle aches, fever, weakness, and anemia. There is a risk of graft-versus-host disease with stem cell transplantation (The Leukemia and Lymphoma Society, Facts 2010-2011, page 3-6). While molecular studies have further refined an understanding of the defects in this disease, none have provided a target for therapy.

Bone cancer is a malignant tumor of the bone that destroys normal bone tissue. Malignant tumors that begin in the bone are called primary bone cancer. Cancer that metastasizes to the bones from other parts of the body is called metastatic cancer and named from the organ from which it spread. Bone cancer is treated with surgery, chemotherapy, radiation, and cryosurgery. All of these treatments have the same unwanted side effects.

Thus, there is a need for the development of additional therapies for leukemia, as well as other blood and bone cancers, those without the unwanted, potentially dangerous side effects.

The emerging role of osteoblasts in hematologic malignancies makes these cells a novel potential target for the treatment of in leukemia and other malignancies and blood disorders.

Serotonin or 5-hydroxytryptamine (5-HT) is a neurotransmitter that modulates both central and peripheral function with both synaptic and paracrine activities, acting on neurons, smooth muscle, and other cell types. Close to ninety percent (90%) of serotonin is synthesized and stored in the gastrointestinal (GI) system, where it mediates sensations between the GI tract and the brain (Berger, Gray, and Roth (2009); Gershon and Tuck (2007)). The remainder of serotonin is found in the central nervous system (CNS) where it helps to regulate mood, appetite, sleep and other behavioral functions, as well as cognitive functions.

Serotonin is synthesized from tryptophan by the enzyme tryptophan hydrolase (Tph) and aromatic amino acid decarboxylase. Two isoforms of Tph have been discovered: Tph1, primarily expressed in the pineal gland and nonneuronal tissue, such as enterochromaffin (EC) cells in the duodenum, and Tph2, exclusively expressed in the neuronal cells (Patel et al. (2004); Côtè et al. (2003)). Given that serotonin cannot cross the blood-brain barrier, these two genes are solely responsible for regulating the level of this molecule in the periphery and in the brain, respectively.

Peripheral or gut-derived serotonin (GDS) is secreted from EC cells in reaction to stimuli, such as distenstion or chemicals, and the secreted serotonin increases the motility of the gut. Several disorders are linked to the dysregulation of peripheral serotonin including GI disorders, emesis, and heart valve damage (Gershon (2005); Gershon (2003); Kulke and Mayer (1999); Andrews et al. (1990)).

Recently, gut-derived serotonin has also been shown to inhibit osteoblast proliferation and bone formation that does not affect bone resorption (Yadav et al. (2008)).

SUMMARY OF THE INVENTION

The present invention is based upon the surprising discovery that the inhibition of peripheral serotonin mitigates or completely eliminates leukemia. Administration of such an inhibitor increased survival, and resulted in no or very few leukemic blasts in femur, liver and spleen tissue in a mouse model of leukemia.

One embodiment of the present invention is a method of treating or preventing leukemia comprising administering to a subject in need thereof, a therapeutically effective amount of an agent that inhibits serotonin Types of leukemia that can be treated or prevented by this method include, but are not limited to, acute lymphocytic leukemia (ALL), chronic lymphocytic leukemia (CLL), acute myeloid leukemia (AML), and chronic myeloid leukemia (CML). In a preferred embodiment, the agent inhibits Tph1, a rate limiting enzyme in the biosynthesis of peripheral serotonin. In the most preferred embodiment, the Tph1 inhibitor is LP-533401 (Lexicon Genetics, Princeton, N.J.). In a preferred embodiment, the subject is a mammal and in the most preferred embodiment, the mammal is a human.

A further embodiment of the present invention is a method of treating or preventing cancer arising in the blood or bone comprising administering to a subject in need thereof, a therapeutically effective amount of an agent that inhibits peripheral serotonin. The cancers would include, but are not limited to, Hodgkin's lymphoma, non-Hodgkin's lymphoma, myeloma, osteosarcoma, chrondrosarcoma, Ewings sarcoma, osteoblastoma, osteoid osteoma, osteochondroma, enchondroma, chondromyxoid fibroma, aneurysmal bone cyst, unicameral bone cyst, and giant cell tumor, as well as bone tumors arising from metastasis. In a preferred embodiment, the agent inhibits Tph1, a rate limiting enzyme in the biosynthesis of serotonin. In the most preferred embodiment, the Tph1 inhibitor is LP-533401 (Lexicon Genetics, Princeton, N.J.). In a preferred embodiment, the subject is a mammal and in the most preferred embodiment the mammal is a human.

A further embodiment of the present invention is a method of treating or preventing a disorder of the blood comprising administering to a subject in need thereof, a therapeutically effective amount of an agent that inhibits peripheral serotonin. These disorders would include, but are not limited to, myeloproliferative syndrome, myelodysplastic syndrome, aplastic anemia, and anemia associated with kidney disease. In a preferred embodiment, the agent inhibits Tph 1, a rate limiting enzyme in the biosynthesis of serotonin. In the most preferred embodiment, the Tph1 inhibitor is LP-533401 (Lexicon Genetics, Princeton, N.J.). In a preferred embodiment, the subject is a mammal and in the most preferred embodiment the mammal is a human.

It was also surprisingly discovered that administration of an inhibitor of peripheral serotonin restores normal hematopoiesis and bone marrow function in subjects with abnormal hematopoiesis. Thus, a further embodiment of the present invention is a method of treating or preventing irregular hematopoiesis comprising administering to a subject in need thereof, a therapeutically effective amount of an agent that inhibits peripheral serotonin. In a preferred embodiment, the agent inhibits Tph1, a rate limiting enzyme in the biosynthesis of serotonin. In the most preferred embodiment, the Tph1 inhibitor is LP-533401 (Lexicon Genetics, Princeton, N.J.). In a preferred embodiment, the subject is a mammal and in the most preferred embodiment the mammal is a human.

It was also surprising discovered that osteoblast growth and proliferation suppresses and mitigates or completely eliminates leukemia. Thus, a further embodiment of the present invention is a method of treating or preventing leukemia comprising administering to a subject in need thereof, a therapeutically effective amount of an agent that promotes osteoblast growth and/or proliferation. Types of leukemia that can be treated or prevented by this method include, but are not limited to, acute lymphocytic leukemia (ALL), chronic lymphocytic leukemia (CLL), acute myeloid leukemia (AML), and chronic myeloid leukemia (CML). In a preferred embodiment, the agent that promotes osteoblast growth and/or proliferation can be, but is not limited to, parathyroid hormone, anti-sclerostin antibodies, kathepsin K inhibitors, and anti-Dickopff 1. In a preferred embodiment, the subject is a mammal and in the most preferred embodiment, the mammal is a human.

A further embodiment of the present invention is a method of treating or preventing cancer arising in the blood or bone comprising administering to a subject in need thereof, a therapeutically effective amount of an agent that that promotes osteoblast growth and/or proliferation. The cancers would include, but are not limited to, Hodgkin's lymphoma, non-Hodgkin's lymphoma, myeloma, osteosarcoma, chrondrosarcoma, Ewings sarcoma, osteoblastoma, osteoid osteoma, osteochondroma, enchondroma, chondromyxoid fibroma, aneurysmal bone cyst, unicameral bone cyst, and giant cell tumor, as well as bone tumors arising from metastasis. In a preferred embodiment, the agent that promotes osteoblast growth and/or proliferation can be, but is not limited to, parathyroid hormone, anti-sclerostin antibodies, kathepsin K inhibitors, and anti-Dickopff 1. In a preferred embodiment, the subject is a mammal and in the most preferred embodiment the mammal is a human.

A further embodiment of the present invention is a method of treating or preventing a disorder of the blood comprising administering to a subject in need thereof, a therapeutically effective amount of an agent that promotes osteoblast growth and/or proliferation. These disorders would include, but are not limited to, myeloproliferative syndrome, myelodysplastic syndrome, aplastic anemia, and anemia associated with kidney disease. In a preferred embodiment, the agent that promotes osteoblast growth and/or proliferation can be, but is not limited to, parathyroid hormone, anti-sclerostin antibodies, kathepsin K inhibitors, and anti-Dickopff 1. In a preferred embodiment, the subject is a mammal and in the most preferred embodiment the mammal is a human.

It was also surprisingly discovered that lack of osteoblasts leads to irregular hematopoiesis and bone marrow function. Thus, a further embodiment of the present invention is a method of treating or preventing irregular hematopoiesis comprising administering to a subject in need thereof, a therapeutically effective amount of an agent that promotes osteoblast growth and/or proliferation. In a preferred embodiment, the agent that promotes osteoblast growth and/or proliferation can be, but is not limited to, parathyroid hormone, anti-sclerostin antibodies, kathepsin K inhibitors, and anti-Dickopff 1. In a preferred embodiment, the subject is a mammal and in the most preferred embodiment the mammal is a human.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

As used in the figures, when relevant: *$p<0.05$ is related to WT Vehicle; #$p<0.05$ is related to WT LP533401; and v$p<0.05$ is related to leukemia Vehicle.

FIG. 8(A) depicts a graph of the luminescence counts in the wild-type and DTAosb mice after number of days after EL4-GRP-luciferase cell injection.

FIG. 8(B) shows cell trafficking and tumor progression of both wild-type and DTAosb mice injected with EL4-GRP-luciferase cells as assessed by an in vivo image system FIG. 9(A) is histological sections from the bone marrow of wild-type and DTAosb mice after injection with EL4-GRP-luciferase cells.

FIG. 9(B) is a graph showing the luminescence counts in the bone marrow of wild-type and DTAosb mice injected with EL4-GRP-luciferase cells.

FIG. 12 is histological sections from the liver of wild-type and DTAosb mice after injection with EL4-GRP-luciferase cells.

FIG. 15 A-G shows graphs showing the number of cell populations, both mature and hematopoietic stem cells, in the bone marrow and spleen of wild-type and DTAosb mice. FIG. 15(A) shows the difference in bone marrow cellularity, FIG. 15(B) shows the percentage of LSK cells, FIG. 15(C) shows the percentage of LSK+CD150+CD48−, LSK+CD150−CD48+ and LSK CD150+CD48+ cells, FIG. 15(D) shows the percentage of mature myeloid cells (CD11b+/Gr1+), FIG. 15(E) shows the percentage of B220+IgM+ and B220+IgM− cells, FIG. 15(F) shows the percentage of Ter119+ erythroid progenitors in the bone marrow, and FIG. 15(G) shows the percentage of lymphoid-biased multipotential progenitor population LSK+/FLT3+ cells.

FIG. 16 A-G are graphs showing the percentage increase of various cell types over six months in DTAosb mice versus wild-type. FIG. 16(A) depicts the change in white blood cells, FIG. 16(B) neutrophils, FIG. 16(C) lymphocytes, FIG. 16(D) monocytes, FIG. 16(E) red blood cells, FIG. 16(F) hematocrit, and FIG. 16(G) hemoglobin.

FIG. 19 A and B shows cell trafficking and tumor progression of both vehicle-treated mice and mice treated with LP-533401 as assessed by an in vivo image system after injection with EL4-GRP-luciferase cells.

FIG. 24 A-G are graphs showing the percentage changes of various cell types in various groups of mice: WT vehicle; WT LP-533401; Leukemia vehicle; and Leukemia LP-533401.

FIG. 28 A-C are histological sections from the bone marrow (FIG. 28(A), blood (FIG. 28(B)), and liver (FIG. 28(C)) of mice with leukemia, some vehicle treated and some treated with LP-533401.

FIG. 30 A-G are graphs showing the percentage changes of various cell types in various groups of mice: WT-vehicle, Leukemia Vehicle; and Leukemia LP-533401.

FIG. 31 A-E shows graphs showing the number of cell populations, both mature and hematopoietic stem cells, in the bone marrow and spleen of four groups of mice: WT-vehicle; WT-LP-533401; Leukemia-vehicle; and Leukemia-LP-533401.

FIG. 32 A-E shows graphs showing the number of cell populations, both mature and hematopoietic stem cells, in the bone marrow and spleen of four groups of mice: WT-vehicle; WT-LP533401; Leukemia-vehicle; and Leukemia-LP-533401. FIG. 32(A) shoes the number of LSK FLT3+ cells, FIG. 32B shows the percentage of B220+IgM+ and B220+IgM– cells, FIG. 32(C) shows the percentage of CD3+ cells, FIG. 32(D) shows the percentage of Ter119+ erythroid progenitors in the bone marrow, and FIG. 32(E) shows the number of B220+IgM+ and B220+IgM– cells.

FIG. 34 A-E is histological sections from mice after injection with WEHI/3B cells, some treated with vehicle and some with LP-533401. FIG. 34(A) is bone marrow, FIG. 34(B) is liver, FIG. 34(C) is spleen, FIG. 34(D) is bone marrow, and FIG. 34(E) is spleen.

FIG. 38 A and B are graphs depicting the expression of various osteoblast differentiating and proliferating genes relative to wild-type in four groups of mice: WT-vehicle; WT-LP-533401; Leukemia- vehicle; and Leukemia-LP-5334401.

DETAILED DESCRIPTION OF THE INVENTION

Figure 1:
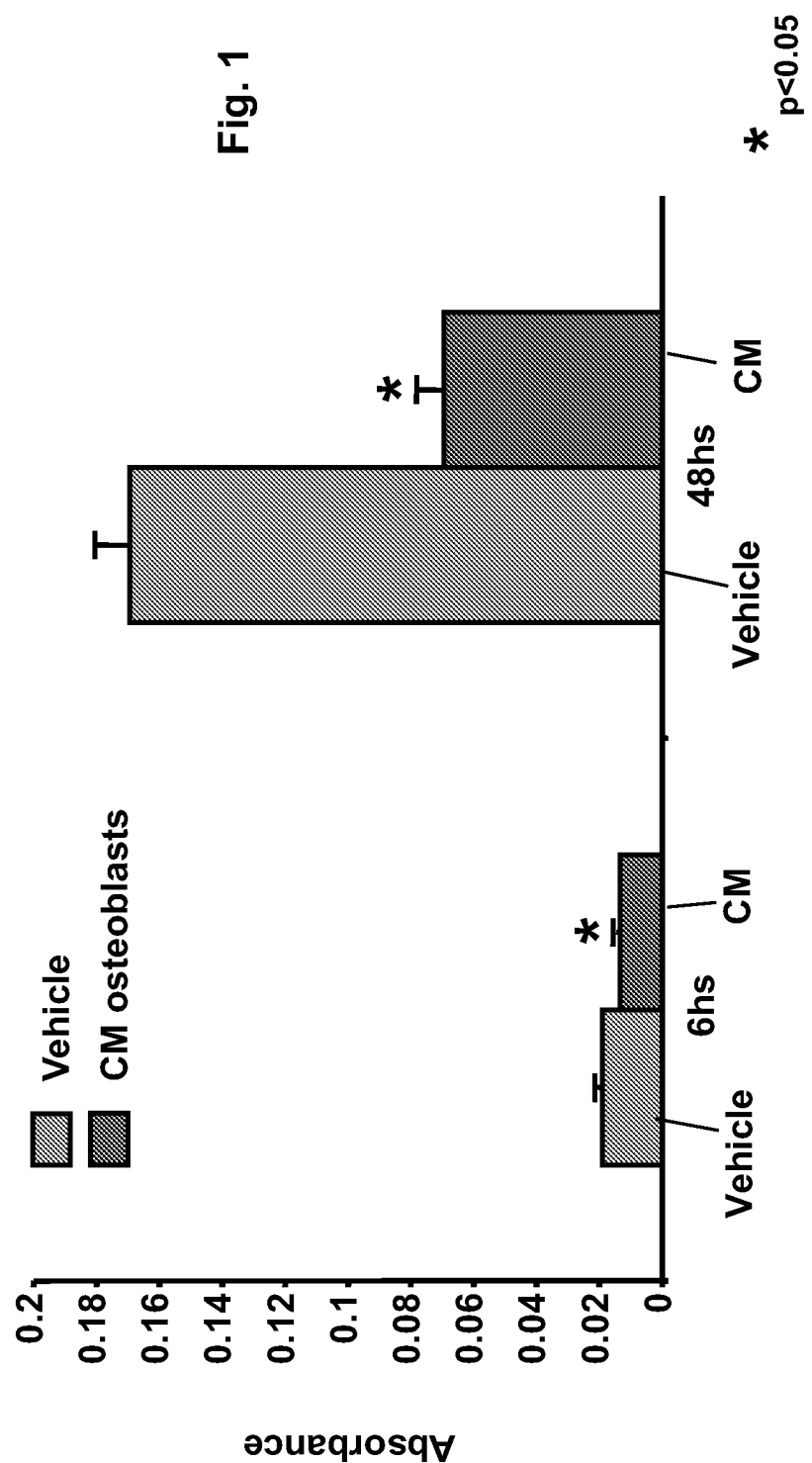
FIG. 1 is a graph depicting the results of an experiment showing that osteoblasts secreted factors that suppress leukemia cell numbers in vitro.

The present invention relates to methods of treating and preventing cancers, particularly blood and bone, more particularly leukemia, by inhibiting peripheral serotonin. The inhibition is preferably caused by the inhibition of Tph1 inhibitor, an enzyme responsible for the production of peripheral serotonin, and more preferably, LP-534401.

In addition, the present invention relates to methods of treating and preventing disorders related to abnormal hematopoiesis, such as blood disorders, by inhibiting serotonin. The inhibition is preferably caused by inhibition of a Tph1 inhibitor, more particularly LP-534401.

The present invention also relates to a method of treating and preventing cancers, particularly blood and bone, and disorders related to abnormal hematopoiesis, such as blood disorders, by increasing osteoblast number, growth and/or proliferation.

Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

"Tph1 inhibitor" is a substance that reduces the amount of 5-hydroxytryptophan produced from tryptophan by Tph1 by at least about 10% in a suitable assay, as compared to the amount of 5-hydroxytryptophan produced from tryptophan by Tph1 in the assay, in the absence of the substance. Assays for determining the level of Tph1 inhibition of an agent are described in International Patent Publication WO 2007/089335.

The terms "treat", "treatment", and the like refer to a means to slow down, relieve, ameliorate or alleviate at least one of the symptoms of the disease, or reverse the disease after its onset.

The terms "prevent", "prevention", and the like refer to acting prior to overt disease onset, to prevent the disease from developing or minimize the extent of the disease or slow its course of development.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications The term "in need thereof" would be a subject known or suspected of having or being at risk of developing cancer, specifically, blood or bone cancers, and more specifically leukemia, or other diseases related to abnormal hematopoiesis.

A subject in need of treatment would be one that has already developed the disease. A subject in need of prevention would be one with risk factors of blood or bone cancer, and/or symptoms of abnormal hematopoiesis or increase serum levels.

The term "agent" as used herein means a substance that produces or is capable of producing an effect and would include, but is not limited to, chemicals, pharmaceuticals, biologics, small organic molecules, antibodies, nucleic acids, peptides, and proteins.

Osteoblasts Role in Hematopoiesis and the Progression of Leukemia

As discussed above, non-hematopoietic cells are found in the bone marrow niche and have also been implicated in the pathogenesis of hematological malignancies. In 2007, studies began to suggest the involvement of non-hematopoietic cells in leukemia progression. For example, mesenchymal cells have been shown to protect leukemia cells from chemotherapy (Iwamoto et al. (2007)). Also, defective Rb, RARγ, and Notch signaling in hematopoietic and non-hematopoietic cells leads to myeloproliferative syndrome (MPS) in mice, which is a condition that predisposes one to acute leukemia development. MPS requires the presence of the mutation in both hematopoietic and non-hematopoietic cells (Kim et al. (2008); Wakley et al. (2007)). A more recent study has shown that osteoblasts are also involved in the hematopoietic process, showing that the deletion of Dicer1 in osteoblast progenitors induces myelodysplasia, another condition that in humans can progress to AML (Raaijmakers et al. (2010)).

The fact that perturbation of osteolineage cells can lead to the disorganization of the hematopoietic system, including development of MDS and AML (Kim et al. (2008); Wakley et al. (2007)), suggests that genetic alterations in these cells can be an initiating lesion in the multistep pathway to marrow-based hematologic malignancies. More recently the identification of a population of bone marrow derived stem/progenitor cells that are osteolineage restricted and can replenish short-lived mature osteoblast lends support to the idea that acquired genetic lesions can affect a larger pool of microenvironmental cells, particularly since these cells are capable of translocation (Park et al. (2012)). It has also been recently shown that leukemic cells compromise osteoblast function, but only transiently increase osteoclast function without increasing bone resorption (Frisch et al. (2012)), suggesting that osteoblasts are an important target of leukemic blasts.

Based upon these findings, the question was asked: is there a functional interaction between osteoblasts and leukemia blasts?

As a first step in determining whether leukemia blasts and bone cells communicate with each other, the effects of leukemia on bone mass in in vivo models of leukemia were investigated. Two different models of leukemia were used. One model used is a murine model of acute lymphoblastic leukemia and uses the cell line EL4. The second model is a murine model of acute myeloid leukemia (AML) and uses the cell line WEHI-3B. The use of two different models of leukemia in these experiments further confirmed the unexpected findings set forth herein.

Figure 2:
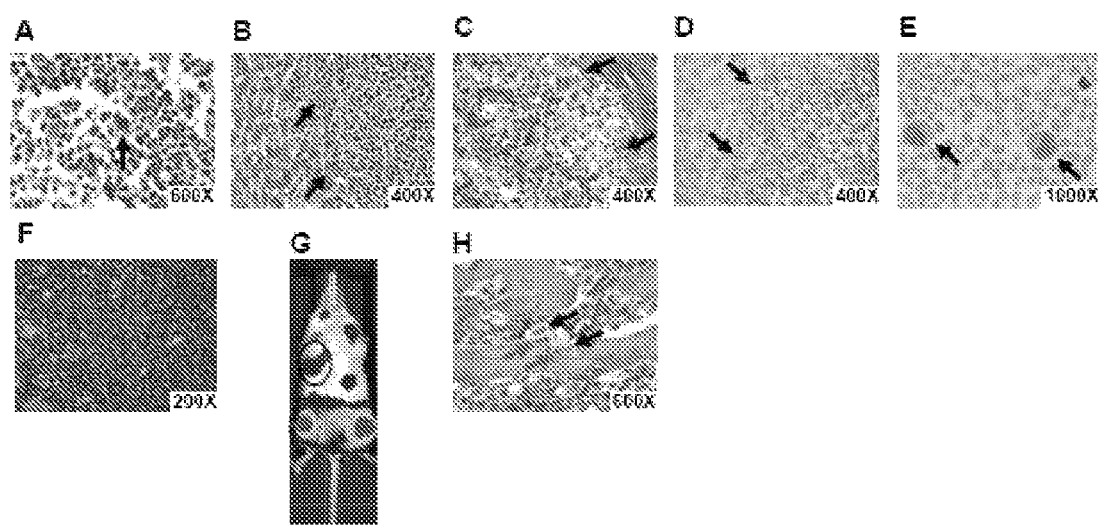
FIG. 2 A-H shows mice injected with either lymphoblastic EL4 cells transduced with a EL4-GFP-luciferase fusion gene, or myeloid-monocytic leukemia cell line, WEHI-3B, can be used as a model for leukemia.

In two different experiments, immunocompetent mice were injected with the myeloid-monocytic leukemia cell line WEHI-3B or the lymphoblastic EL4 cells (FIG. 2; Example 2). In both models, leukemia progression was associated with a marked decrease in bone mass, as well as a decrease in osteoblast number. However, osteoclast activity remained unaffected (FIGS. 3-6; Example 3). Thus, leukemia decreases bone mass by decreasing osteoblast differentiation, thus indicating that leukemia blasts effect osteoblast function.

The next question was the opposite: whether osteoblasts influence leukemia engraftment and progression. Using both in vitro and in vivo studies, this question was answered in the positive.

As a first step in addressing the question, leukemia blasts were cultured with conditioned medium from osteoblasts. It was observed that osteoblasts secrete factors that decrease leukemia blast numbers (FIG. 1; Example 1).

Figure 13B:
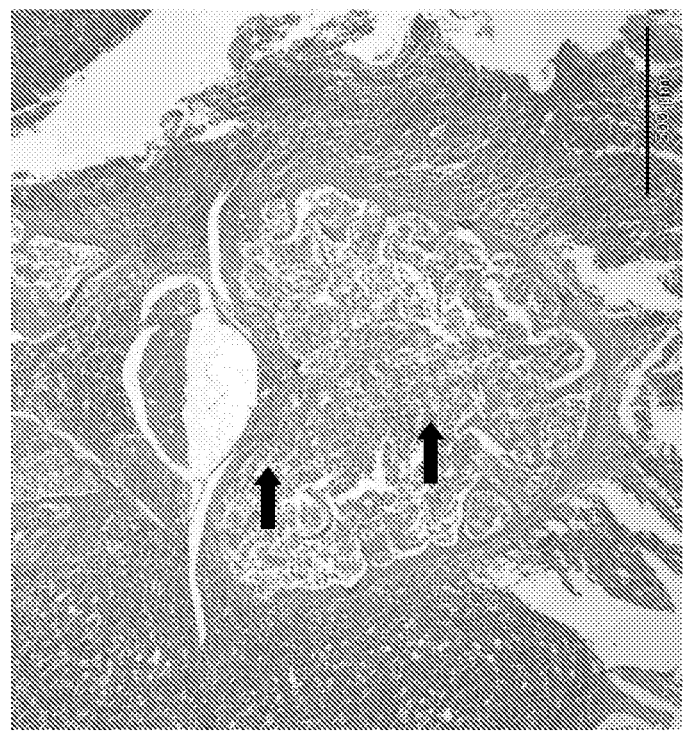
FIG. 13(B) shows a bone sample of a DTAosb mouse with malignant cells in the vertebral bodies of the spinal canal.

Additional in vivo data supports this finding as well. Using an in vivo mouse model with a 50% reduction in osteoblast number, designated DTAosb (FIG. 7; Example 4), it was shown these mice had an increased tumor burden over their wild-type counterparts (FIG. 8; Example 5). It was also shown that osteoblast ablation increased tumor cell engraftment in the bone marrow (FIG. 9; Example 6). Histological sections from the bone marrow of osteoblast-deficient and wild-type mice showed almost all of the osteoblast-deficient mice had tumor engraftment, while the wild-type mice had normal bone marrow tissue with no leukemia infiltration (FIG. 10; Example 6). Similar results were found in the peripheral blood, liver, spleen and kidney (FIGS. 11-12; Example 6). The osteoblast-deficient mice also had a significantly shorter overall survival (FIG. 14; Example 7), and greater incidence of hind-limb paralysis, indicating an increase in tumor burden in the bone marrow, since the hind-limb paralysis is caused by the invasion of malignant cells from vertebral bodies into the spinal canal (FIG. 13; Example 7). Thus, this data demonstrate the lack of osteoblasts adversely affect leukemia progression.

Because osteoblasts have been implicated in hematopoiesis, the effects of partial osteoblast ablation on hematopoiesis were investigated. The mice used in this study were not leukemic, only lacking osteoblasts, i.e., DTAosb mice. These experiments showed an increase in the population of mature myeloid cells coupled with a reduction in B-lymphopoiesis in both mature and immature cells in DTAosb mice versus their wild-type counterparts (FIG. 15; Example 8). The increase in myeloids cells and decrease in lymphocytic populations are indicative of myeloproliferative/myelodysplastic syndrome in mice that leads to leukemia. Also consistent with these observations, white blood cells remained unchanged, whereas the percentage of neutrophils increased in the blood of the DTAosb mice (FIG. 16; Example 8). Monocytes also decreased despite the increase in bone marrow CD11b+/Gr1+ cells, potentially indicating a shift of the myeloid lineage towards granulocyte differentiation at the expense of monocyte differentiation (FIG. 16; Example 8). These data taken together indicate that lack of osteoblasts changes the lineage determination of hemapoietic stem cells by altering myeloid and lymphocytic compartments which leads to an increased leukemia burden.

Thus, the data taken together, as set forth in more detail in the Examples, supports decreased osteoblast function and numbers compromising hematopoiesis, and leading to increased leukemia burden. Compromised osteoblast function may indirectly support leukemia progression due to the deregulated hematopoiesis. Indeed the data show that mice lacking osteoblasts are characterized by a hematological phenotype that favors myeloid and lymphocytic cell expansion and therefore may create a favorable environment for bone marrow failure and replacement of healthy hematopoietic cells with leukemia blasts. This effect occurs in the absence of leukemia. Moreover, reestablishment of osteoblast numbers also reestablishes normal hematopoiesis.

Furthermore, given the well-recognized role of the microenvironment and more specifically, osteoblasts in the establishment of solid tumors such as breast and prostate cancer, this data supports the role of osteoblasts in all hematologic malignancies, and other cancers.

Thus, a composition or method which increases and/or reestablishes osteoblast number and function would reestablish normal hematopoiesis, and can be used as a treatment and/or prevention of disease states arising from irregular hematopoiesis, including but not limited to, acute lymphocytic leukemia (ALL), chronic lymphocytic leukemia (CLL), acute myeloid leukemia (AML), and chronic myeloid leukemia (CML), myeloproliferative syndrome, myelodysplastic syndrome, aplastic anemia, and anemia associated with kidney disease, as well as cancers of the bone, breast, and prostate.

LP-533401 a Serotonin Inhibitor, Slows or Prevents Leukemia Progression and Restores Normal Bone Marrow Function Peripheral or gut-derived serotonin is associated with numerous processes, and it dysregulation associated with various disease states. However, the inhibition of serotonin via direct inhibition of Tph enzymes was not seriously contemplated due to the importance of serotonin in brain and CNS function. The discovery of two distinct and separate genes, TPH1 and TPH2, responsible for gut-derived and neuronal serotonin, respectively, lead to the development of drugs that specifically inhibit one or the other enzyme. The development of inhibitors specific to one or the other Tph enzyme is challenging given that Tph1 and Tph2 are 71% identical in amino acid sequence and approximately 90% identical in catalytic domain (Liu et al. (2008)).

Two such Tph1 inhibitors, LP-533401 and LP-615819, are described in Liu et al. (2008):

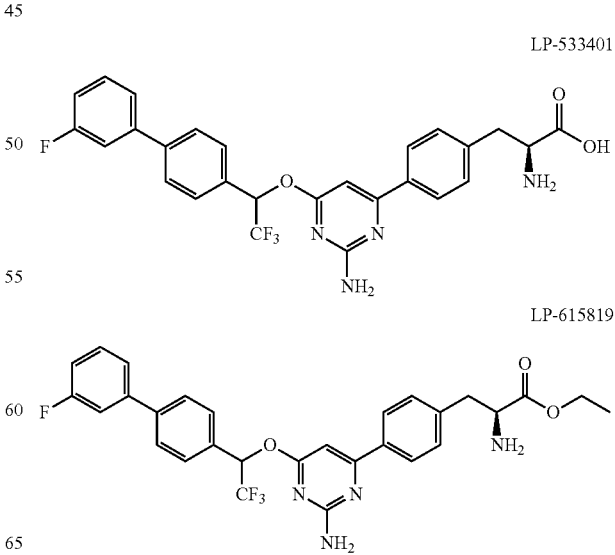

LP-615819 is a prodrug of LP-533401. In this reported study, both compounds were administered to mice twice per day over a 3-4 day period in amounts of either 30 or 90 mg/kg. After six consecutive doses, serotonin levels in the small intestine were lowered 55% and 70% in the 30 mg and 90 mg mice, respectively, while brain-derived serotonin was unchanged. Even though LP-533401 inhibits Tph2 as effectively as Tph1 in vitro, it did not cross the blood-brain barrier in vivo, and therefore did not cause a decrease in brain-derived serotonin. Liu et al. disclosed that LP-533401 and LP-615819 may be useful for treating chemotherapy-induced emesis and irritable bowel syndrome. LP-533401 has also been found to be effective against bone loss and may be a potential therapy for osteoporosis (Inose et al. (2011); Yadov et al. (2010)).

However, until now there has been no description or suggestion that Tph1 inhibitors, including LP-534401, could be effective against cancer, more specifically, cancers of the blood and bone, and most specifically, leukemia, or other disorders related to blood.

Based upon the findings that osteoblast deficiency leads to abnormal hematopoiesis and increased tumor burden and decreased survival in leukemia, it was hypothesized that the course of leukemia could be ameliorated in mice with an increased osteoblast number. Since it has been shown that gut-derived serotonin decreases osteoblast proliferation (Yadov et al. (2008)), it was proposed that inhibiting gut-derived serotonin would re-establish normal hematopoiesis as well as decrease the effects of leukemia.

This hypothesis that the inhibition of gut-derived serotonin on leukemia progression was evaluated using the same mouse models as in the earlier studies, one based upon lymphoblastic leukemia and one based upon acute myeloid leukemia.

In the first study, immunocompetent, syngenic mice injected with a lymphoma/lymphoblastic cell line, EL-4. Four groups of mice were observed: wild-type mice with no leukemia, treated with a vehicle (WT); mice with leukemia, treated with a vehicle (Leuk-veh); mice with no leukemia treated with LP-533401 (NL-LP); and mice with leukemia treated with LP-533401 (Leuk-LP).

Figure 17:
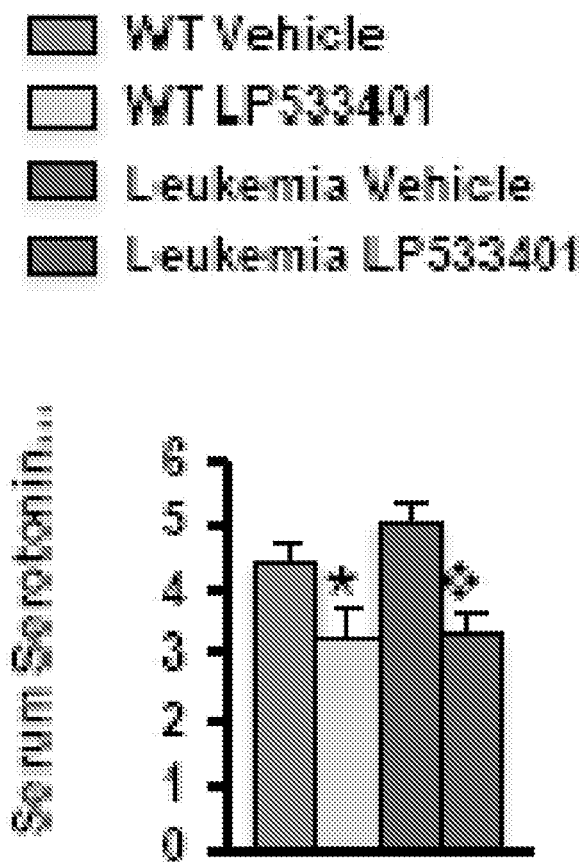
FIG. 17 is a graph depicting the difference between serum serotonin levels in four groups of mice: WT-vehicle; WT-LP; leukemia-vehicle; and leukemia-LP.

It was found that the mice treated with LP-533401 had a 30% decrease in serum serotonin levels as compared to vehicle-treated animals in both the leukemic and non-leukemic groups (FIG. 17; Example 9). As a result there was an increase in osteoblast numbers, trabecular bone volume, and bone formation rate in the LP-533401 treated mice, showing that the inhibition of gut-derived serotonin diminished bone loss observed in mice engrafted with malignant cells (FIG. 18; Example 9).

Figure 19A:
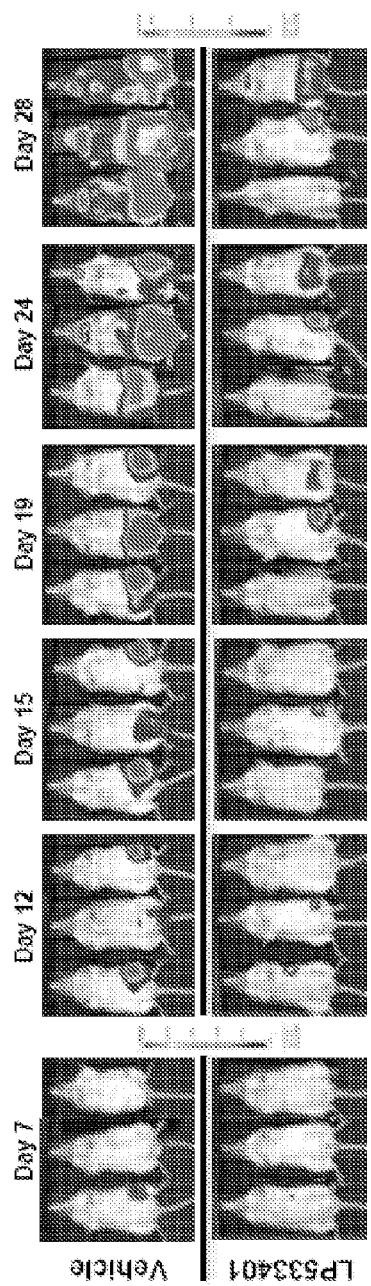
FIG. 19(A) shows day 7 through day 28 of three representative mice from both the vehicle- and LP-533401-treated groups.
Figure 19B:
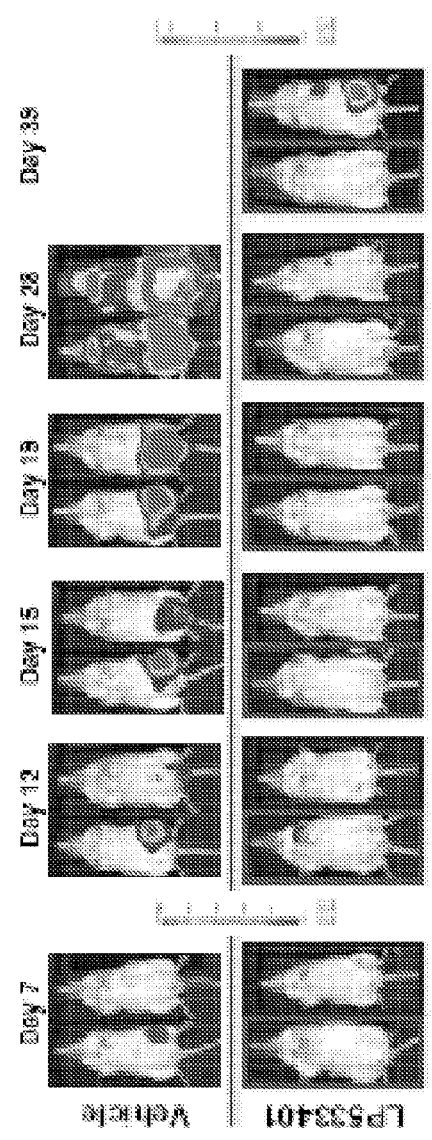
FIG. 19(B) shows day 7 through day 39 of two of the three mice in each group.

Using both bioluminescence imaging and luciferase intensity, it was shown that there was a decreased tumor burden in mice treated with LP-533401. Surprisingly, of the ten (10) leukemic mice treated with LP-533401, two (2) were cleared of the disease, one (1) developed leukemia at a very late stage and was later cleared of the disease, and two (2) never developed the disease (FIGS. 19-20; Example 9). Even more striking, the LP-533401 administration resulted in a significantly longer overall survival, indicating a beneficial effect of the compound on subjects with acute lymphoblastic leukemia (FIG. 21; Example 9). Also surprisingly, the development of hind-limb paralysis in untreated animals was almost twice that of animals treated with LP-533401, clearly indicating the decrease in tumor burden in the bone marrow of subjects treated the drug (FIG. 23; Example 9). Moreover, the osteoblast number was inversely correlated with leukemia tumor burden in these mice, further proving that the inhibition of gut-derived serotonin inhibits leukemia progression by preventing the decrease in osteoblast number (FIG. 23; Example 9).

Other evaluations confirmed these surprising findings. The anemia in the leukemic mice was ameliorated with the treatment of LP-533401 because the compound inhibits the decrease in red blood cells, hemoglobin, and hematocrit that result from leukemia (FIG. 24; Example 9). LP-533401 treatment also prevented leukemia induced suppression of reticulocyte numbers, a hallmark of leukemia (FIG. 24; Example 9). Additionally, the increase in white blood cells another hallmark of leukemia, was also prevented by treatment with LP-533401 (FIG. 24; Example 9). Lastly, LP-533401 treatment restored to normal levels the increase in neutrophils and monocytes, and the decrease in lymphocytes that is associated with leukemia establishment and progression (FIG. 24; Example 9).

When the same mice were treated with LP-533401, but sacrificed at a particular point in time, the same results were seen. Osteoblast numbers, bone volume, and bone formation rate that was decreased by leukemia, was restored by LP-533401 treatment (FIG. 25; Example 10). Tumor burden was decreased, as well as a reduction in the leukemic infiltration of the marrow (FIG. 26-29; Example 10). Mice treated with LP-533401 did not have an increase in immature lymphoblastic cells as did the leukemic mice (FIG. 28; Example 10). There was also no leukemia blasts in the liver of the LP-533401 treated mice (FIG. 28; Example 10), and prevention of lineage deregulation caused by leukemia in the LP-533401 treated mice (FIG. 30; Example 10).

Based on the previous findings that partial osteoblast ablation is deleterious to hematopoiesis, the effects of non-leukemic mice treated with LP-533401 on the hematopoietic compartment were observed. Remarkably, it was found that LP-533401 recovered normal bone marrow function in the exact opposite fashion as seen in the osteoblast-deficient mice (FIGS. 31 and 32; Example 11).

The next study showed that LP-533401 has a beneficial effect on acute myeloid leukemia using the using mice inoculated with a myelomonocytic leukemia cell line, WEHI/3B. In these experiments, the anti-leukemic properties of LP-533401 were evaluated on tumor burden at the tissue level. Four groups of mice were used: wild-type mice with no leukemia and treated with a vehicle (WT); mice with no leukemia treated with LP-533401 (NL-LP); mice with leukemia and treated with a vehicle (Leuk-veh); and mice with leukemia treated with LP-533401 (Leuk-LP).

Figure 33A:
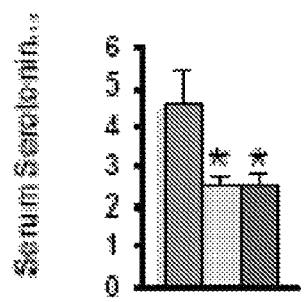
FIG. 33 A-C depicts graphs of various measurements in four groups of mice: WT-vehicle; WT-LP-533401; Leukemia-vehicle; and Leukemia-LP-533401-FIG. 33(A) serum serotonin, FIG. 33(B) spleen weight, and FIG. 33(C) body weight.
Figure 33B:
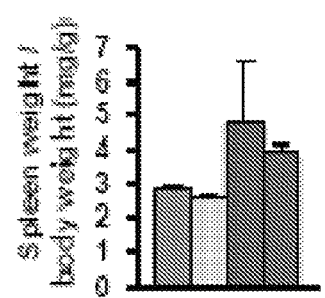
Figure 33C:
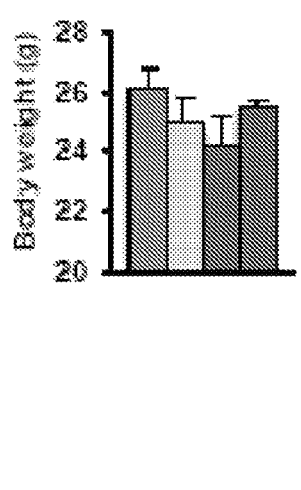

In this experiment, a 50% decrease in serum serotonin levels in mice with no leukemia treated with LP-533401 was found as compared to wild-type mice (FIG. 33; Example 12). Also treatment with LP-533401 alleviated the enlargement of the spleen seen in leukemic mice (FIG. 33; Example 12). Additionally there was no loss of body weight in leukemic mice treated with LP-533401 as seen in the non-treated mice (FIG. 33; Example 12).

Histological analysis showed LP-533401 treated mice had a reduced number of leukemia blast. Of the 14 mice treated, 10 had less than 5% blasts as compared to the 10 mice treated with vehicle (FIGS. 34 and 35; Example 12)

Figure 36:
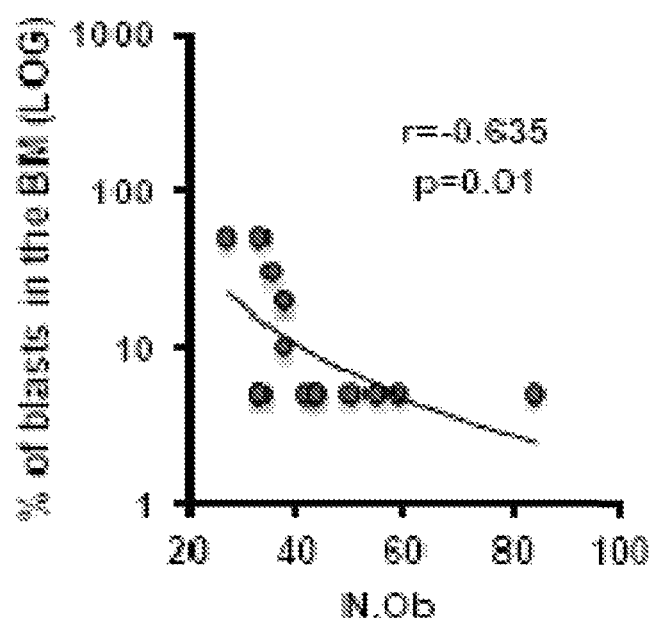
FIG. 36 is a graph correlating osteoblast numbers with tumor burden.

In this study as in the previous one, the osteoblast numbers inversely correlated with the percentage of leukemic blasts in the bone marrow (FIG. 36; Example 12), indicating that the outcome of leukemia reduction is dependent on the presence of osteoblasts.

Further parameters were looked at in this study, including trabecular bone volume, restoration of bone loss, and expression of genes related to osteoblasts. For each of these parameters, mice treated with LP-533401 scored better than the vehicle-treated leukemic mice. The mice treated with LP-533401 had higher bone volume (FIG. 37; Example 12), restoration of bone loss (FIG. 37; Example 12), and expression of osteoblast differentiating and proliferating genes closer to wild-type than vehicle treated leukemic mice (FIG. 38; Example 12). Treatment with LP-533401 ameliorated the anemia caused by leukemia (FIG. 39; Example 12).

Because a potential direct role of serotonin on hematologic malignant cells has been previously suggested, a study was performed to determine if serotonin treatment had a direct effect on the leukemia blasts. As shown in the studies below, serotonin treatment of either the myeloid or the lymphoblastic leukemia cells had no effect on their proliferation or survival. Importantly, neither implantation of serotonin-treated leukemia cells affected leukemia progression (FIGS. 40 and 41; Example 13). Therefore, the data clearly indicate that at least in these two syngeneic models of acute leukemia, the decrease in serotonin levels hinders leukemia progression by actions that do not involve direct effects on leukemia blasts.

All of the data taken together, presented above and in more detail in the Examples, show that LP-533401 decreases tumor burden, decreases anemia, increases survival, and in many cases reverses or prevents leukemia. Moreover, treatment with LP-533401 restores normal bone marrow function as well as normal osteoblast number and function. Thus, it has been shown that LP-533401 is an effective agent for the prevention and treatment of leukemia, other blood cancers, bone cancers, and blood disorders such as anemia.

Since LP-533401 is an inhibitor of Tph1, an enzyme responsible for the production of gut-derived serotonin, it reasons that other Tph1 inhibitors would act in the same beneficial manner.

Tph1 Inhibitors

Various other Tph1 inhibitors related to LP-533401 and LP-615819, including multicyclic amino acid derivatives, are described in U.S. Patent Application Publication 2007/191370, and in related applications including International Patent Publication WO 2007/089335, which references are incorporated herein by reference in their entirety.

These inhibitors, listed below, can also be used in the methods of the present invention.

(S)-2-amino-3-(4-(4-amino-6-((R)-1-(naphthalen-2-yl)ethylamino)-1,3,5-triazin-2-yl)phenyl)propanoic acid;
(S)-2-amino-3-(4-(4-amino-6-((4'-methylbiphenyl-4-yl)methylamino-1,3,5-triazin-2-yl)pheny)propanoic acid;
(S)-2-amino-3-(4-(4-morpholino-6-(naphthalen-2-ylmethylamino)-1,3,5-triazin-2-yl)phenyl)propanoic acid;
(2S)-2-amino-3-(4-(2-amino-6-(2,2,2-trifluoro-1-(2-(trifluoromethyl)phenyl)ethoxy)pyrimidin-4-yl)phenyl)propanoic acid;
(2S)-2-amino-3-(4-(2-amino-6-(2,2,2-trifluoro-1-p-tolylethoxy)pyrimidin-4-yl)phenyl)propanoic acid;
(2S)-2-amino-3-(4-(2-amino-6-(1-cyclohexyl-2,2,2-trifluoroethoxy)pyrimidin-4-yl(phenyl)propanoic acid;
(S)-2-amino-3-(4-(6-(2-fluorophenoxy)pyrimidin-4-yl)phenyl)propanoic acid;
(2S)-2-amino-3-(4-(4-(3-(4-chlorophenyl)piperidin-1-yl)-1,3,5-triazin-2-yl)phenyl)propanoic acid;
(2S)-2-amino-3-(4-(4-amino-6-(2,2,2-trifluoro-1-phenylethoxy)-1,3,5-triazin-2-yl)phenyl)propanoic acid;
(S)-2-amino-3-(5-(4-amino-6-((R)-(naphthalen-2-yl)ethylamino)-1,3,5-triazin-2-yl)pyridin-2-yl)propanoic acid;
(S)-2-amino-3-(3-(4-amino-6-(R)-1-(naphthalen-2-yl)ethylamino)-1,3,5-triazin-2-yl)-1H-pyrazol-1-yl)propanoic acid;
(S)-2-amino-3-(4'-(3-(cyclopentyloxy)-4-methoxybenzylamino)biphenyl-4-yl)propanoic acid;
(S)-2-amino-3'(4-(6-(3-(cyclopentyloxy)-4-methoxybenzylamino)pyrimidin-4-yl)phenyl)propanoic acid;
(S)-2-amino-3-(4-(6-(3-(cyclopentyloxy)-4-methoxybenzylamino)pyrazin-2-yl)phenyl)propanoic acid;
(S)-2-amino-3-(4-(5-((4'-methylbiphenyl-2-yl)methylamino)pyrazin-2-yl)phenyl)propanoic acid;
(2S)-2-amino-3-(4-(6-(2,2,2-trifluoro-1-phenylethoxy)-pyrimidin-4-yl)phenyl)propanoic acid;
(2S)-2-amino-3-(4-(6-(1-(3,4-difluorophenyl)-2,2,2-trifluoroethoxy)pyrimidin-4-yl)phenyl)propanoic acid;
(S)-2-amino-3-(4-(5-(3-(cyclopentyloxy)-4-methoxybenzylamino)-pyrazin-2-yl)phenyl)propanoic acid;
(S)-2-amino-3-(4-(5-((3-(cyclopentyloxy)-4-methoxybenzyl)-(methyl)amino)pyrazin-2-yl)phenyl)propanoic acid;
(S)-2-amino-3-(4-(5-((1,3-dimethyl-1H-pyrazol-4-yl)methylamino)pyrazin-2-yl)phenyl)propanoic acid;
(S)-2-amino-3-(4-(4-amino-6-((S)-1-(naphthalen-2-yl)ethylamino)-1,3,5-triazin-2-yloxy)phenyl)propanoic acid;
(S)-2-amino-3-(4-(4-amino-6-((R)-1-(biphenyl-2-yl)-2,2,2-trifluoroethoxy)-1,3,5-triazin-2-yl)phenyl)propanoic acid;
(2S)-2-amino-3-(4-(4-amino-6-(1-(6,8-difluoronaphthalen-2-yl)ethylamino)-1,3,5-triazin-2-yl)phenyl)propanoic acid;
(2S)-2-amino-3-(4-(4-amino-6-(2,2,2-trifluoro-1-(3'-methylbiphenyl-2-yl)ethoxy)-1,3,5-triazin-2-yl)phenyl)propanoic acid;
(S)-2-amino-3-(4-(5-(3,4-dimethoxyphenylcarbamoyl)-pyrazin-2-yl)phenyl)propanoic acid;
(S)-2-amino-3-(4-(2-amino-6-(4-(2-(trifluoromethyl)phenyl)-piperidin-1-yl)pyrimidin-4-yl)phenyl)propanoic acid;
(S)-2-amino-3-(4-(2-amino-6-((R)-1-(naphthalen-2-yl)ethylamino)pyrimidin-4-yl)phenyl)propanoic acid;
(S)-2-amino-3-(4-(2-amino-6-(methyl(R)-1-(naphthalen-2-yl)ethyl)amino)pyrimidin-4-yl)phenyl)propanoic acid;
(S)-2-amino-3-(4-(2-amino-6-((S)-2,2,2-trifluoro-1-(6-methoxynaphthalen-2-yl)ethoxy)pyrimidin-4-yl)phenyl) propanoic acid;
(S)-2-amino-3-(4-(5-(biphenyl-4-ylmethylamino)pyrazin-2-yl)phenyl)propanoic acid;
(S)-2-amino-3-(4-(5-(naphthalen-2-ylmethylamino)pyrazin-2-yl)phenyl)propanoic acid;
(S)-2-(tert-butoxycarbonylamino)-3-(4-(5-(naphthalen-2-ylmethylamino)pyrazin-2-yl)phenyl)propanoic acid;
(S)-2-morpholinoethyl 2-amino-3-(4-(5-(naphthalen-2-ylmethylamino)pyrazin-2-yl)phenyl)propanoate;
(S)-2-amino-3-(4-(2-amino-6-(2,2,2-trifluoro-1-(3'-fluorobiphenyl-4-yl)ethoxy)pyrimidin-4-yl)phenyl)propanoic acid;
(S)-2-amino-3-(4-(2-amino-6-(benzylthio)pyrimidin-4-yl) phenyl)propanoic acid;
(S)-2-amino-3-(4-(2-amino-6-(naphthalen-2-ylmethylthio) pyrimidin-4-yl)phenyl)propanoic acid;
(2S)-2-amino-3-(4-(2-amino-6-(1-(3,4-difluorophenyl)-2,2,2-trifluoroethoxy)pyrimidin-4-yl)phenyl)propanoic acid;
(2S)-2-amino-3-(4-(2-amino-6-(2,2,2-trifluoro-1-(3'-methylbiphenyl-2-yl)ethoxy)pyrimidin-4-yl)phenyl)propanoic acid;
(S)-2-amino-3-(4-(5-(3-(cyclopentyloxy)-4-methoxybenzylamino)pyridin-3-yl)phenyl)propanoic acid;

2-amino-3-(3-(4-amino-6-((R)-1-(naphthalen-2-yl)ethyl-amino)-1,3,5-triazin-2-yl)phenyl)propanoic acid;
2-amino-3-(4-(4-amino-6-((R)-1-(naphthalen-2-yl)ethyl-amino)-1,3,5-triazin-2-yl)-2-fluorophenyl)propanoic acid;
(2S)-2-amino-3-(4-(4-amino-6-(1-(adamantyl)ethylamino)-1,3,5-triazin-2-yl)phenyl)propanoic acid;
(S)-2-amino-3-(4-(5-fluoro-4-((R)-1-(naphthalen-2-yl)ethylamino)pyrimidin-2-yl)phenyl)propanoic acid;
(S)-2-amino-3-(4-(2-amino-6-(4-(trifluoromethyl)-benzylamino)pyrimidin-4-yl)phenyl) propanoic acid;
2-amino-3-(5-(5-phenylthiophen-2-yl)-1H-indol-3-yl)propanoic acid;
(S)-2-amino-3-(4-(4-(4-phenoxyphenyl)-1H-1,2,3-triazol-1-yl)phenyl)propanoic acid;
(S)-2-amino-3-(4-(4-(4-(thiophene-2-carboxamido)phenyl)-IH-1,2,3-triazol-1-yl)phenyl)propanoic acid;
(S)-2-amino-3-(4-(2-amino-6-(phenylethynyl)pyrimidin-4-yl)phenyl)propanoic acid;
(S)-2-amino-3-(4-(5-2-fluoro-4,5-dimethoxybenzylamino)pyrazin-2-yl)phenyl)propanoic acid;
(S)-2-amino-3-(4-(2-amino-6-(4-(2-methoxyphenyl)piperidin-1-yl)pyrimidin-4-yl)phenyl)propanoic acid;
(S)-2-amino-3-(4-(6-(3-(cyclopentyloxy)4-methoxybenzylamino)-2-(dimethylamino)pyrimidin-4-yl)phenyl)propanoic acid;
(S)-2-amino-3-(4-(5-(3,4-dimethylbenzylamino)pyrazin-2-yl)phenyl)propanoic acid;
(S)-2-amino-3-(4-(5-(biphenyl-2-ylmethylamino)pyrazin-2-yl)phenyl)propanoic acid
(S)-ethyl 2-amino-3-(4-(2-amino-6-(4-(trifluoromethyl)benzylamino)pyrimidin-4-yl)phenyl)propanoate;
(S)-2-amino-3-(4-(5-(cyclopentylmethylamino)pyrazin-2-yl)phenyl)propanoic acid;
(2S)-2-amino-3-(4-(2-amino-6-(3-(2-(trifluoromethyl)phenyl)pyrrolidin-1-yl)pyrimidin-4-yl)phenyl)propanoic acid;
(2S)-2-amino-3-(4-(2-amino-6-(1,2,3,4-tetrahydronaphthalen-1-yl-amino)pyrimidin-4-yl)phenyl)propanoic acid;
(S)-2-amino-3-(4-(2-amino-6-((R)-1-(naphthalen-2-yl)ethoxy)pyrimidin-4-yl)phenyl)propanoic acid;
(2S)-2-amino-3-(4-(2-amino-6-(1,2-diphenylethylamino)pyrimidin-4-yl)phenyl)propanoic acid;
(S)-2-amino-3-(4-(2-amino-6-((R)-1-(4-(benzo[b]thiophen-3-yl)phenyl)ethylamino)pyrimidin-4-yl)phenyl)propanoic acid;
(S)-2-amino-3-(4-(4-amino-6-((R)-1-(4'-methoxybiphenyl-4-yl)ethylamino)-1,3,5-triazin-2-yl)phenyl)propanoic acid;
2-amino-3-(1-(4-amino-6-((R)-1-(naphthalen-2-yl)ethyl-amino)-1,3,5-triazin-2-yl)piperidin-4-yl)propanoic acid;
(2S)-2-amino-3-(4-(4-amino-6-(1-(4-fluoronaphthalen-1-yl)ethylamino)-1,3,5-triazin-2-yl)phenyl)propanoic acid;
(S)-2-amino-3-(4-(4-amino-6-((3'-fluorobiphenyl-4-yl)methylamino)-1,3,5-triazin-2-yl)phenyl)propanoic acid;
2-amino-3-(4-(4-amino-6-((R)-1-(naphthalen-2-yl)ethyl-amino)-1,3,5-triazin-2-yl)-2-fluorophenyl)propanoic acid;
(S)-2-amino-3-(4-(2-amino-6-((R)-2,2,2-trifluoro-1-(3'-methoxybiphenyl-4-yl)ethoxy)pyrimidin-4-yl)phenyl) propanoic acid;
(2S)-2-amino-3-(4-(4-amino-6-(2,2,2-trifluoro-1-(3'-fluorobiphenyl-2-yl)ethoxy)-1,3,5-triazin-2-yl)phenyl)propanoic acid;
(2S)-2-amino-3-(4-(4-amino-6-(1-(4-tert-butylphenyl)ethylamino)-1,3,5-triazin-2-y])phenyl)propanoic acid;
(2S)-2-amino-3-(4-(2-amino-6-(2,2,2-trifluoro-1-(3'-fluorobiphenyl-4-yl)ethoxy)pyrimidin-4-yl)phenyl)propanoic acid;
(2S)-2-amino-3-(4-(4-amino-6-(6,7-dihydroxy-1-methyl-3,4-dihydroisoquinolin-2(1H)-yl)-1,3,5-triazin-2-yl)phenyl)propanoic acid;
(2S)-2-amino-3-(4-(4-amino-6-(2,2,2-trifluoro-1-(3'-methylbiphenyl-4-yl)ethoxy)-1,3,5-triazin-2-yl)phenyl)propanoic acid;
(S)-2-amino-3-(4-(4-amino-6-((R-1-(naphthalen-2-yl)ethylamino)pyrimidin-2-yl)phenyl)propanoic acid;
(S)-2-amino-3-(4-(2-amino-6-(benzylthio)pyrimidin-4-yl)phenyl)propanoic acid;
(2S)-2-amino-3-(4-(2-amino-6-(2,2,2-trifluoro-1-(4'-fluorobiphenyl-4-yl)ethoxy)pyrimidin-4-yl)phenyl)propanoic acid;
(2S)-2-amino-3-(4-(6-(3-(4-chlorophenoxy)piperidin-1-yl)pyrimidin-4-yl)phenyl)propanoic acid;
(S)-3-(4-(4-amino-6-((R)-1-(naphthalen-2-yl)ethylamino)-1,3,5-triazin-2-yl)phenyl)-2-(2-aminoacetamido)propanoic acid;
(S)-2-amino-3-(4-(6-((R)-1-(naphthalen-2-yl)ethylamino)-2-(trifluoromethyl)pyrimidin-4-yl)phenyl)propanoic acid;
(S)-2-amino-3-(4-(2-amino-6-(4-(3-chlorophenyl)piperazin-1-yl)pyrimidin-4-yl)phenyl)propanoic acid;
(S)-2-amino-3-(4-(2-amino-6-((R)-2,2,2-trifluoro-1-phenylethoxy)pyrimidin-4-yl)phenyl)propanoic acid;
(2S)-2-amino-3-(4-(2-amino-6-(1,4-diphenylbutylamino)pyrimidin-4-yl)phenyl)propanoic acid;
(2S)-2-amino-3-(4-(6-(1-(3'-chlorobiphenyl-2-yl)-2,2,2-trifluoroethoxy)pyrimidin-4-yl)phenyl)propanoic acid;
(2S)-2-amino-3-(4-(4-amino-6-(1-(biphenyl-4-yl)-2,2,2-trifluoroethoxy)-1,3,5-triazin-2-yl)phenyl)propanoic acid;
(2S)-2-amino-3-(4-(2-amino-6-(2,2,3,3,3-pentafluoro-1-(3-fluoro-4-methylphenyl)propoxy)pyrimidin-4-yl)phenyl) propanoic acid;
(S)-ethyl 2-amino-3-(4-(2-amino-6-((R)-2,2,2-trifluoro-1-(3'-methoxybiphenyl-4-yl)ethoxy)pyrimidin-4-yl)phenyl) propanoate;
(S)-2-amino-3-(4-(2-amino-6-((S)-2,2,2-trifluoro-1-(3'-methoxybiphenyl-4-yl)ethoxy)pyrimidin-4-yl)phenyl) propanoic acid;
(2S)-2-amino-3-(4-(2-amino-6-(2,2,2-trifluoro-1-(3-fluoro-3-methoxybiphenyl-4-yl)ethoxy)pyrimidin-4-yl)phenyl) propanoic acid;
(2S)-2-amino-3-(4-(2-amino-6-(1-(3'-(dimethylamino)biphenyl-2-yl)-2,2,2-trifluoroethoxy)pyrimidin-4-yl)phenyl)propanoic acid;
(2S)-2-amino-3-(4-(2-amino-6-(2,2,2)-trifluoro-1-(3'-methoxy-5-methylbiphenyl-2-yl)ethoxy)pyrimidin-4-yJ)phenyl)propanoic acid;
(2S)-2-amino-3-(4-(2-amino-6-(2,2,2-trifluoro-1-(4'-methoxy-5-methylbiphenyI-2-yl)ethoxy)pyrimidin-4-yl) phenyl)propanoic acid;
(2S)-2-amino-3-(4-(2-amino-6-(2,2,2-trifluoro-1-(3'-methoxy-3-(methylsulfonyl)biphenyl-4-yl)ethoxy)pyrimidin-4-yl)phenyl)propanoic acid;
(2S)-2-amino-3-(4-(2-amino-6-(1-(2-(cyclopropyl-methoxy)-4-fluorophenyl-2,2,2-trifluoroethoxy)pyrimidin-4-yl)phenyl)propanoic acid;
(2S)-2-amino-3-(4-(6-(1-(2-(cyclopropylmethoxy)-4-fluorophenyl)-2,2,2-trifluoroethoxy)pyrimidin-4-yl)phenyl) propanoic acid;
(2S)-2-amino-3-(4-(2-amino-6-(2,2,2-trifluoro-1-(2-(isopentyloxy)phenyl)ethoxy)pyrimidin-4-yl)phenyl)propanoic acid;

(2S)-2-amino-3-(4-(5-(2,2,2-trifluoro-1-(3'-fluorobiphenyl-4-yl)ethoxy)pyrazin-2-yl)phenyl)propanoic acid;
(2S)-2-amino-3-(4-(2-amino-6-(2,2,2-trifluoro-1-(4'-methoxybiphenyl-2-yl)ethoxy)pyrimidin-4-yl)phenyl)propanoic acid;
(2S)-2-amino-3-(4-(2-amino-6-(1-(3'-carbamoylbiphenyl-2-yl)-2,2,2-trifluoroethoxy)pyrimidin-4-yl)phenyl)propanoic acid;
(2S)-2-amino-3-(4-(2-amino-6-(1-(4'-carbamoylbiphenyl-2-yl)-2,2,2-trifluoroethoxy)pyrimidin-4-yl)phenyl)propanoic acid;
(2S)-2-amino-3-(4-(2-amino-6-(2,2,2-trifluoro-1-(4-(2-methoxyphenoxy)phenyl)ethoxy)pyrimidin-4-yl)phenyl)propanoic acid;
(2S)-2-amino-3-(4-(6-(2,2,2-trifluoro-1-(4-(2-methoxyphenoxy)phenyl)ethoxy)pyrimidin-4-yl)phenyl)propanoic acid;
(2S)-2-amino-3-(4-(6-(2,2,2-trifluoro-1-(2-(isopentyloxy)phenyl)ethoxy)pyrimidin-4-yl)phenyl)propanoic acid;
(2S)-3-(4-(6-(3'-acetamidobiphenyl-2-yl)-2,2,2-trifluoroethoxy)-2-aminopyrimidin-4-yl)phenyl)-2-aminopropanoic acid;
(2S)-3-(4-(6-(1-(4'-acetamidobiphenyl-2-yl)-2,2,2-trifluoroethoxy)-2-aminopyrimidin-4-yl)phenyl)-2-aminopropanoic acid;
(2S)-2-amino-3-(4-(2-amino-6-(1-(4-cyanophenyl)-2,2,2-trifluoroethoxy)pyrimidin-4-yl)phenyl)propanoic acid;
(S)-ethyl 2-amino-3-(4-(2-amino-6-((R)-2,2,2-trifluoro-1-p-tolylethoxy)pyrimidin-4-yl)phenyl)propanoate;
(2S)-2-ammo-3-(4-(2-amino-6-(2,2,2-trifluoro-1-(1-methoxybicyclo[2.2.2]oct-5-en-2-yl)ethoxy)pyrimidin-4-yl)phenyl)propanoic acid;
(2S)-2-amino-3-(4-(2-amino-6-(1-(4-(cyclopentyloxy)phenyl)-2,2,2-trifluoroethoxy)pyrimidin-4-yl)phenyl)propanoic acid;
(2S)-2-amino-3-(4-(6-(1-(4-(cyclopentyloxy)phenyl)-2,2,2-trifluoroethoxy)pyrimidin-4-yl)phenyl)propanoic acid;
(2S)-2-amino-3-(4-(2-amino-6-(2,2,2-trifluoro-1-(4-(3-methoxyphenoxy)phenyl)ethoxy)pyrimidin-4-yl)phenyl)propanoic acid;
(2S)-2-amino-3-(4-(2-amino-6-(1-(4,5-dimethoxybiphenyl-2-yl)-2,2,2-trifluoroethoxy)pyrimidin-4-yl)phenyl)propanoic acid;
(2S)-2-amino-3-(4-(2-amino-6-(1-(4,5-dimethoxy-3'-methylbiphenyl-2-yl)-2,2,2-trifluoroethoxy)pyrimidin-4-yl)phenyl)propanoic acid;
(2S)-2-amino-3-(4-(5-(2,2,2-trifluoro-1-(2'-methylbiphenyl-2-yl)ethoxy)pyrazin-2-yl)phenyl)propanoic acid;
(2S)-2-amino-3-(4-(6-(2,2,2-trifluoro-1-(4-(3-methoxyphenoxy)phenyl)ethoxy)pyrimidin-4-yl)phenyl)propanoic acid;
(2S)-2-amino-3-(4-(2-amino-6-(1-(2-(3,5-difluorophenoxy)phenyl)-2,2,2-trifluoroethoxy)pyrimidin-4-yl)phenyl)propanoic acid;
(2S)-2-amino-3-(4-(2-amino-6-(2,2,2-trifluoro-1-(4-(4-methoxyphenoxy)phenyl)ethoxy)pyrimidin-4-yl)phenyl)propanoic acid;
(2S)-2-amino-3-(4-(2-amino-6-(1-4'-((S)-2-amino-2-carboxyethyl)biphenyl-2-yl)-2,2,2-trifluoroethoxy)pyrimidin-4-yl)phenyl)propanoic acid;
(2S)-2-amino-3-(4-(2-amino-6-(1-(2-bromophenyl)-2,2,2-trifluoroethoxy)pyrimidin-4-yl)phenyl)propanoic acid;
(2S)-2-amino-3-(4-(5-(2,2,2-trifluoro-1-(3'-methylbiphenyl-2-yl)ethoxy)pyrazin-2-yl)phenyl)propanoic acid;
(2S)-2-amino-3-(4-(2-amino-6-(2,2,2-trifluoro-1-(4-methoxybiphenyl-2-yl)ethoxy)pyrimidin-4-yl)phenyl)propanoic acid;
(2S)-2-amino-3-(4-(5-(2,2,2-trifluoro-1-(2-(4-methylthiophen-3-yl)phenyl)ethoxy)pyrazin-2-yl)phenyl)propanoic acid;
(2S)-2-amino-3-(4-(2-amino-6-(2,2,2-trifluoro-1-(4-methoxy-3'-methylbiphenyl-2-yl)ethoxy)pyrimidin-4-yl)phenyl)propanoic acid;
(2S)-2-amino-3-(4-(2-amino-S-(2,2,2-trifluoro-1-(3'-(hydroxymethyl)biphenyl-2-yl)ethoxy)pyrimidin-4-yl)phenyl)propanoic acid;
(2S)-2-amino-3-(4-(2-amino-6-(1-(3'-cyanobiphenyl-2-yl)-2,2,2-trifluoroethoxy)pyrimidin-4-yl)phenyl)propanoic acid;
(2S)-2-amino-3-(4-(6-(1-(2-(3,5-difluorophenoxy)phenyl)-2,2,2-trifluoroethoxy)pyrimidin-4-yl)phenyl)propanoic acid;
(2S)-2-amino-3-(4-(6-(2,2,2-trifluoro-1-(4-(4-methoxyphenoxy)phenyl)ethoxy)pyrimidin-4-yl)phenyl)propanoic acid;
(2S)-2-amino-3-(4-(2-amino-6-(2,2,2-trifluoro-1-(2-(4-methylthiazol-2-yl)thiophen-3-yl)ethoxy)pyrimidin-4-yl)phenyl)propanoic acid;
(2S)-2-amino-3-(4-(2-amino-6-(2,2,2-trifluoro-1-(5-(4-methoxyphenyl)isoxazol-3-yl)ethoxy)pyrimidin-4-yl)phenyl)propanoic acid;
(2S)-2-amino-3-(4-(2-amino-6-(2,2,2-trifluoro-1-(1-phenyl-5-(trifluoromethyl)-1H-pyrazol-4-yl)ethoxy)pyrimidin-4-yl)phenyl)propanoic acid;
(2S)-2-amino-3-(4-(2-amino-6-(1-(2-(cyclohexyloxy)-4-methylphenyl)-2,2,2-trifluoroethoxy)pyrimidin-4-yl)phenyl)propanoic acid;
(2S)-2-amino-3-(4-(2-amino-6-(1-(2-(cyclopentyloxy)-4-methylphenyl)-2,2,2-trifluoroethoxy)pyrimidin-4-yl)phenyl)propanoic acid;
(2S)-2-amino-3-(4-(2-amino-6-(1-(benzo[d]thiazol-6-yl)-2,2,2-trifluoroethoxy)pyrimidin-4-yl)phenyl)propanoic acid;
(2S)-2-amino-3-(4-(2-amino-6-(2,2,2-trifluoro-1-(1-methyl-1H-imidazol-5-yl)ethoxy)pyrimidin-4-yl)phenyl)propanoic acid;
(2S)-2-amino-3-(4-(6-(1-(2-(cyclopentyloxy)-4-methylphenyl)-2,2,2-trifluoroethoxy)pyrimidin-4-yl)phenyl)propanoic acid;
(2S)-2-amino-3-(4-(6-(1-(2-(cyclohexyloxy)-4-methylphenyl)-2,2,2-trifluoroethoxy)pyrimidin-4-yl)phenyl)propanoic acid;
(2S)-2-amino-3-(4-(2-amino-6-(2,2,2-trifluoro-1-(pyridin-3-yl)ethoxy)pyrimidin-4-yl)phenyl)propanoic acid;
(2S)-2-amino-3-(4-(2-amino-6-(1-(1,3-dimethyl-1H-pyrazol-5-yl)-2,2,2-trifluoroethoxy)pyrimidin-4-yl)phenyl)propanoic acid;
(S)-2-amino-3-(4-(2-amino-6-(3'-hydroxyphenyl)pyrimidin-4-yl)phenyl)propanoic acid;
(2S)-2-amino-3-(4-(2-amino-6-(2,2,2-trifluoro-1-(3'-hydroxybiphenyl-2-yl)ethoxy)pyrimidin-4-yl)phenyl)propanoic acid;
(S)-2-amino-3-(4-(2-amino-6-(3,5-difluorophenyl)pyrimidin-4-yl)phenyl)propanoic acid;
(2S)-2-amino-3-(4-(2-amino-6-(1-(3,5'-difluorobiphenyl-2-yl)-2,2,2-trifluoroethoxy)pyrimidin-4-yl)phenyl)propanoic acid;
(2S)-2-amino-3-(4-(6-(2,2,2-trifluoro-1-(3,-fluorobiphenyl-3-yl)ethoxy)pyrazin-2-yl)phenyl)propanoic acid;
(2S)-2-amino-3-(4-(2-amino-6-(1-(5-ethoxy-2-methyl-2,3-dihydrobenzofuran-6-yl)-2,2,2-trifluoroethoxy)pyrimidin-4-yl)phenyl)propanoic acid;
(2S)-2-amino-3-(4-(2-amino-6(1-(benzofuran-5-yl)-2,2,2-trifluoroethoxy)pyrimidin-4-yl)phenyl)propanoic acid;

(2S)-2-amino-3-(4-(2-amino-6-(2,2,2-trifluoro-1-(2-m-tolylfuran-3-yl)ethoxy)pyrimidin-4-yl)phenyl)propanoic acid;

(S)-ethyl 3-(4-(2-amino-6-((R)-2,2,2-trifluoro-1-(3'-methoxybiphenyl-4-yl)ethoxy)pyrimidin-4-yl)phenyl)-2-(2-aminoacetamido)propanoate;

(2S)-2-amino-3-(4-(6-(2,2,2-trifluoro-1-(2-(4-methylthiophen-3-yl)phenyl)ethoxy)pyrazin-2-yl)phenyl)propanoic acid;

(2S)-2-amino-3-(4-(2-amino-6-(2,2,2-trifluoro-1-(5-methyl-3-phenylisoxazol-4-yl)ethoxy)pyrimidin-4-yl)phenyl)propanoic acid;

(S)-2-amino-3-(4-(2-amino-6-(3-(methylthio)phenyl)pyrimidin-4-yl)phenyl)propanoic acid;

(2S)-2-amino-3-(4-(2-amino-5-(2,2,2-trifluoro-1-(3'-(methylthio)biphenyl-2-yl)ethoxy)pyrimidin-4-yl)phenyl)propanoic acid;

(2S)-2-amino-3-(4-(2-amino-6-(1-(3'-((dimethylamino)methyl)biphenyl-2-yl)-2,2,2-trifluoroethoxy)pyrimidin-4-yl)phenyl)propanoic acid;

(S)-2-amino-3-(4-(2-amino-6-(3-(trifluoromethoxy)phenyl)pyrimidin-4-yl)phenyl)propanoic acid;

(2S)-2-amino-3-(4-(2-amino-6-(2,2,2-trifluoro-1-(3'-(trifluoromethoxy)biphenyl-2-yl)ethoxy)pyrimidin-4-yl)phenyl)propanoic acid;

(S)-3-(4-(2-amino-6-((R)-2,2,2-trifluoro-1-(3'-methoxybiphenyl-4-yl)ethoxy)pyrimidin-4-yl)phenyl)-2-(2-aminoacetamido)propanoic acid;

(2S)-2-amino-3-(4-(2-amino-6-(2,2,2-trifluoro-1-(1-methyl-5-phenyl-1H-pyrazol-4-yl)ethoxy)pyrimidin-4-yl)phenyl)propanoic acid;

(2S)-2-amino-3-(4-(2-amino-6-(2,2,2-trifluoro-1-(4-(methylsulfonyl)phenyl)ethoxy)pyrimidin-4-yl)phenyl)propanoic acid;

(S)-2-amino-3-(4-(2-amino-6-((R)-1-(3'-(dimethylamino)biphenyl-2-yl)-2,2,2-trifluoroethoxy)pyrimidin-4-yl)phenyl)propanoic acid;

(2S)-2-amino-3-(4-(2-amino-6-(1-(2-chloro-4-(methylsulfonyl)phenyl)-2,2,2-trifluoroethoxy)pyrimidin-4-yl)phenyl)propanoic acid;

(2S)-2-amino-3-(4-(2-amino-6-(2,2,2-trifluoro-1-(3-(furan-2-yl)thiophen-2-yl)ethoxy)pyrimidin-4-yt)phenyl)propanoic acid;

(2S)-2-amino-3-(4-(2-amino-6-(1-(2-(cyclopentyloxy)-4-fluorophenyl)-2,2,2-trifluoroethoxy)pyrimidin-4-yl)phenyl)propanoic acid;

(2S)-2-amino-3-(4-(2-amino-6-(2,2,2-trifluoro-1-(2-(3-methoxyphenyl)cyclohex-1-enyl)ethoxy)pyrimidin-4-yl)phenyl)propanoic acid;

(2S)-2-amino-3-(4-(2-amino-6-(2,2,2-trifluoro-1-(pyrimidin-5-yl)ethoxy)pyrimidin-4-yl)phenyl)propanoic acid;

(2S)-2-amino-3-(4-(5-(2,2,2-trifluoro-1-(3'-methoxybiphenyl-3-yl)ethoxy)pyrazin-2-yl)phenyl)propanoic acid;

(S)-2-amino-3-(4-(2-amino-6-((S)-1-(3'-(dimethylamino)biphenyl-2-yl)-2,2,2-trifluoroethoxy)pyrimidin-4-yl)phenyl)propanoic acid (2S)-2-amino-(4-(2-amino-6-(2,2,2-trifluoro-1-(2-(furan-2-carboxamido)phenyl)ethoxy)pyrimidin-4-yl)phenyl)propanoic acid;

(2S)-2-amino-3-(4-(2-amino-6-(1-(4-chloro-2-(methylsulfonyl)phenyl)-2,2,2-trifluoroethoxy)pyrimidin-4-yl)phenyl)propanoic acid;

(S)-isopropyl 2-amino-3-(4-(2-amino-6-((R)-2,2,2-trifluoro-1-(3'-methoxybiphenyl-4-yl)ethoxy)pyrimidin-4-yl)phenyl)propanoate;

(2S)-2-amino-3-(4-(6-(1-(2-(cyclopentyloxy)-4-fluorophenyl)-2,2,2-trifluoroethoxy)pyrimidin-4-yl)phenyl)propanoic acid;

(2S)-2-amino-3-(4-(6-(1-(2-(cyclohexyloxy)-4-fluorophenyl)-2,2,2-trifluoroethoxy)pyrimidin-4-yl)phenyl)propanoic acid;

(2S)-2-amino-3-(4-(2-amino-6-(2,2,2-trifluoro-1-(1-(thiophen-2-yl)cyclohexyl)ethoxy)pyrimidin-4-yl)phenyl)propanoic acid;

(2S)-2-amino-3-(4-(2-(2,2,2-trifluoro-1-(3'-methoxybiphenyl-4-yl)ethoxy)thiazol-S-yl)phenyl)propanoic acid;

(2S)-2-amino-3-(4-(2-amino-6-(1-(2-(cyclohexyloxy)-4-fluorophenyl)-2,2,2-trifluoroethoxy)pyrimidin-4-yl)phenyl)propanoic acid;

(2S)-2-amino-3-(4-(2-amino-6-(2,2,2-trifluoro-1-(1-(4-ethoxyphenyl)cyclohexyl)ethoxy)pyrimidin-4-yl)phenyl)propanoic acid;

(2S)-2-amino-3-(4-(6-(2,2,2-trifluoro-1-(4-fluoro-2-methylphenyl)ethoxy)pyrimidin-4-yl)phenyl)propanoic acid;

(2S)-2-amino-3-(4-(2-amino-6-(2,2,2-trifluoro-1-(4-fluoro-2-methylphenyl)ethoxy)pyrimidin-4-yl)phenyl)propanoic acid;

(2S)-2-amino-3-(4-(2-amino-6-(oxazol-2-yl)phenyl)methoxy)pyrimidin-4-yl)propanoic acid;

(S)-2-amino-3-(4-(2-ammo-6-(1-cyclohexyl-2,2,2-trifluoroethylideneaminooxy)pyrimidin-4-yl)phenyl)propanoic acid;

(2S)-2-amino-3-(4-(2.amino-6-(1-(2-(3-(dimethylamino)phenyl)furan-3-yl)-2,2,2-trifluoroethoxy)pyrimidin-4-yl)phenyl)propanoic acid;

(2S)-2-amino-3-(4-(2-amino-6-(2,2,2-trifluoro-1-(5-phenylthiophen-2-yl)ethoxy)pyrimidin-4-yl)phenyl)propanoic acid;

(S)-phenyl-2-amino-3-(4-(2-amino-6-((R)-2,2,2-trifluoro-1-(3'-methoxybiphenyl-4-yl)ethoxy)pyrimidin-4-yl)phenyl)propanoate;

(S)-2-amino-3-(4-(2-amino-6-((R)-1-(3'-((dimethylamino)methyl)biphenyl-4-yl)-2,2,2-trifluoroethoxy)pyrimidin-4-yl)phenyl)propanoic acid;

(S)-2-amino-3-(4-(1-(3-methoxybenzoyl)-1H-pyrazol-4-yl)phenyl)propanoic acid;

(2S)-2-amino-3-(4-(6-(2,2,2-trifluoro-1-(S-phenylfuran-2-yl)ethoxy)pyrimidin-4-yl)phenyl)propanoic acid;

(2S)-2-amino-3-(4-(2-amino-6-(1-(4-chloro-2-fluorophenyl)-2,2,2-trifluoroethoxy)pyrimidin-4-yl)phenyl)propanoic acid;

(S,E)-2-amino-3-(4-(2-amino-6-(4-(trifluoromethyl)styryl)pyrimidin-4-yl)phenyl)propanoic acid;

(2S)-2-amino-3-(4-(2-amino-6-(1-(3,4-dichlorophenyl)-2,2,2-trifluoroethoxy)pyrimidin-4-yl)phenyl)propanoic acid;

(2S)-2-amino-3-(4-(2-amino-6-(1-(4-chloro-3-fluorophenyl)-2,2,2-trifluoroethoxy)pyrimidin-4-yl)phenyl)propanoic acid;

(S)-2-amino-3-(4-(2-amino-6-((R)-1-(3'-(dimethylamino)biphenyl-4-yl)-2,2,2-trifluoroethoxy)pyrimidin-4-yl)phenyl)propanoic acid;

(2S)-2-amino-3-(4-(2-amino-6-(1-chloro-2,2,2-trifluoro-1-(4-methoxybiphenyl-2-yl)ethoxy)pyrimidin-4-yl)phenyl)propanoic acid;

(2S)-2-amino-3-(4-(6-(2,2,2-trifluoro-1-(5-phenylthiophen-2-yl)ethoxy)pyrimidin-4-yl)phenyl)propanoic acid;

(S)-2-amino-3-(4-(5-(4-phenoxyphenyl)-1H-1,2,3-triazol-1-yl)phenyl)propanoic acid;

(S,E)-2-amino-3-(4-(2-amino-6-(2-(biphenyl-4-yl)vinyl)pyrimidin-4-yl)phenyl)propanoic acid;

(S)-2-amino-3-(4-(4-amino-6-((R)-2,2,2-trifluoro-1-(3'-methoxybiphenyl-4-yl)ethoxy)pyrimidin-2-yl)phenyl)propanoic acid;

(S)-2-amino-3-(4-(4'-methoxybiphenyl-4-ylsulfonamido)phenyl)propanoic acid;

(2S)-2-amino-3-(4-(2-amino-6-(2,2,2-trifluoro-1-(6-(3-methoxyphenyl)pyridin-3-yl)ethoxy)pyrimidin-4-yl)phenyl)propanoic acid;

(2S)-2-amino-3-(4-(2-amino-6-(2,2,2-trifluoro-1-(6-(2-fluoro-3-methoxyphenyl)pyridin-3-yl)ethoxy)pyrimidin-4-yl)phenyl)propanoic acid;

2-amino-3-(5-(4'-methylbiphenyl-4-yl)-1H-indol-3-yl)propanoic acid;

2-amino-3-(5-m-tolyl-1H-indol-3-yl)propanoic acid;

(2S)-2-amino-3-(4-(2-(2-methoxyphenyl)furan-3-carboxamido)phenyl)propanoic acid;

2-amino-3-(5-(1-benzyl-1H-pyrazol-4-yl)-1H-indol-3-yl)propanoic acid;

(2S)-2-amino-3-(4-(2-amino-6-(2,2,2-trifluoro-1-(6-(thiophen-2-yl)pyridin-3-yl)ethoxy)pyrimidin-4-yl)phenyl)propanoic acid;

2-amino-3-(6-(1-benzyl-1H-pyrazol-4-yl)-1H-indol-3-yl)propanoic acid;

(S)-2-amino-3-(4-(2-(4-(trifluoromethyl)phenyl)thiazol-4-yl)methylamino)phenyl)propanoic acid;

(S)-2-amino-3-(4-((4'-methoxybiphenyl-4-ylsulfonamido)methyl)phenyl)propanoic acid;

(S)-2-amino-3-(4-(3-(2-methoxydibenzo[b,d]furan-3-yl)ureido)phenyl)propanoic acid;

(S)-2-amino-3-(4-(3-(2,2-diphenylethyl)ureido)phenyl)propanoic acid;

(S)-2-amino-3-(4-(phenylethyl)phenyl)propanoic acid;

(S)-2-amino-3-(4-(2-amino-6-((5-(1-methyl-5-(trifluoromethyl)-1H-pyrazol-3-yl)thiophen-2-yl)methoxy)pyrimidin-4-yl)phenyl)propanoic acid (2S)-2-amino-3-(4-(2-amino-6-(1,1,1-trifluoro-3-((R)-2,2,3-trimethylcyclopent-3-enyl)propan-2-1oxy)pyrimidin-4-yl)phenyl)propanoic acid (2S)-2-amino-3-(4-(2-amino-6-(3-(2-hydroxyethylcarbamoyl)piperidin-1-yl)pyrimidin-4-yl)phenyl)propanoic acid;

(2S)-2-amino-3-(4-(2-amino-6-(3-(pyridin-2-yloxy)piperidin-1-yl)pyrimidin-4-yl)phenyl)propa-ioic acid;

(S)-2-amino-3-(4-(2-amino-6-(4-chloro-3-(piperidine-1-carbonyl)phenyl)pyrimidin-4-yl)phenyl)propanoic acid;

as well as racemic mixtures and individual enantiomers of said compounds, and salts of said compounds with a physiologically acceptable acid.

Additional TPH 1 inhibitors that may be used in the present invention include:

N-[(1R,4R,9aS)-4-phenyl octahydropyrido[2,1-c][1,4]oxazin-1-yl]3,4,5-trimethoxybenzamide;

2,6-piperidinedione, 3-[3-(dimethylamino)propyl]-3-(3-methoxyphenyl)-4,4-dimethyl-, monohydrochloride; and Triptosine (CAS registry number 86248-47-7; U.S. Pat. No. 4,472,387).

Methods of making many of the therapeutic agents disclosed in the preceding paragraphs are disclosed in International Patent Publication WO 2007/089335. Such disclosures are incorporated herein by reference.

Tph1 inhibitors having the following formulas can also be used in embodiments of the present invention:

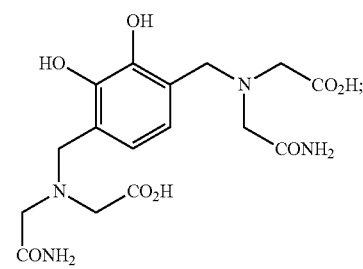

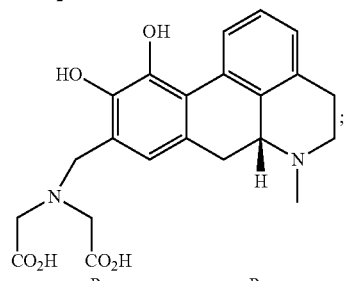

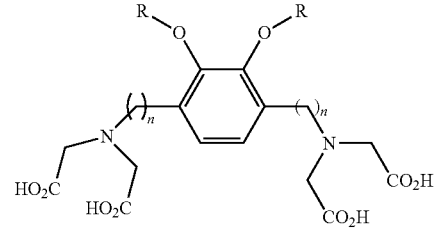

where R is hydrogen or lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); and n is 1, 2, or 3;

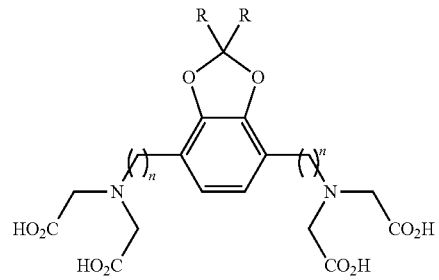

where R is hydrogen or lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); and n is 1, 2, or 3;

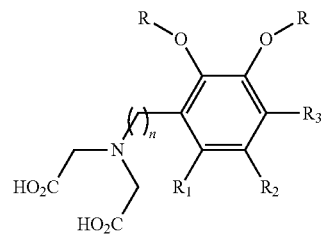

where R is hydrogen or lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); $R_1$, $R_2$, and $R_3$, are independently: hydrogen; halogen (preferably F or Cl); lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); alkoxy, where alkoxy refers to a group R'—O—, where R' is lower alkyl as defined above; amino; or nitro; and n is 1, 2, or 3;

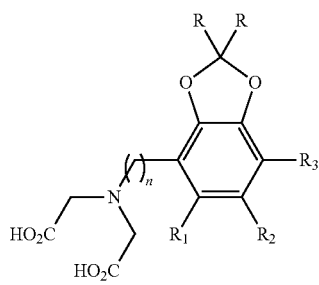

where R is hydrogen or lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); $R_1$, $R_2$, and $R_3$, are independently: hydrogen; halogen (preferably F or Cl); lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); alkoxy, where alkoxy refers to a group R'—O—, where R' is lower alkyl as defined above; amino; or nitro; and n is 1, 2, or 3;

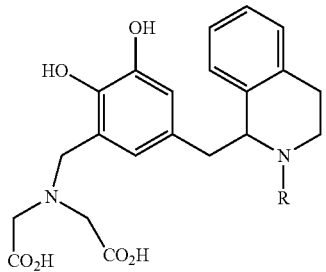

where R is hydrogen; lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); or cycloalkyl, where cycloalkyl refers a cyclic hydrocarbon group having 3 to 8 carbon atoms;

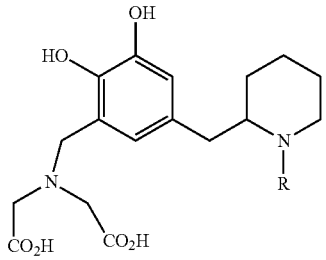

where R is hydrogen; lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); or cycloalkyl, where cycloalkyl refers a cyclic saturated hydrocarbon group having 3 to 8 carbon atoms;

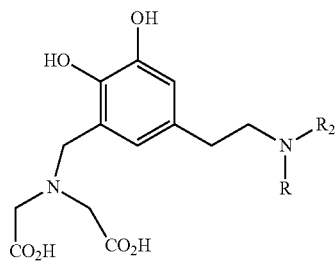

where $R_1$ and $R_2$ are, independently, hydrogen; lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); or cycloalkyl, where cycloalkyl refers a cyclic saturated hydrocarbon group having 3 to 8 carbon atoms;

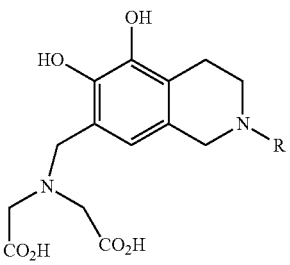

where R is hydrogen; lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); or cycloalkyl, where cycloalkyl refers a cyclic saturated hydrocarbon group having 3 to 8 carbon atoms;

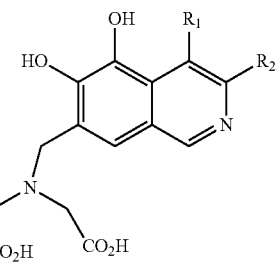

where $R_1$ and $R_2$ are, independently, hydrogen; lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); cycloalkyl, where cycloalkyl refers a cyclic saturated hydrocarbon group having 3 to 8 carbon atoms; F, Cl, or OH;

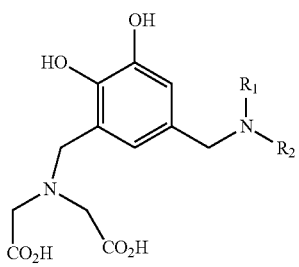

where $R_1$ and $R_2$ are, independently, hydrogen; lower alkyl, where lower alkyl refers to a straight-chain or branched-chain hydrocarbon group having 1 to 6 carbon atoms (e.g., methyl, ethyl, propyl, isopropyl, butyl, isobutyl, pentyl and hexyl); or cycloalkyl, where cycloalkyl refers a cyclic saturated hydrocarbon group having 3 to 8 carbon atoms.

Other Tph1 inhibitors which can be used in the method of the invention include pCPA and CBMIDA, the structures of which are found below:

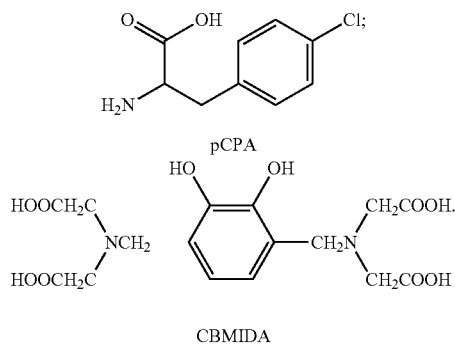

Methods of making the compounds described in the preceding paragraphs can be found in Xie et al. (2005) *Bioorganic & Medicinal Chemistry Letters* 15:3267, incorporated herein by reference in its entirety.

The present invention also encompasses the use of certain derivatives of the Tph1 inhibitors disclosed herein. For example, prodrugs of the Tph1 inhibitors could be produced by esterifying the carboxylic acid functions of the Tph1 inhibitors with a lower alcohol, e.g., methanol, ethanol, propanol, isopropanol, butanol, etc. The use of prodrugs of the Tph1 inhibitors that are not esters is also contemplated. For example, pharmaceutically acceptable carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters of the Tph 1 inhibitors are also contemplated. In some embodiments, the prodrugs will contain a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Guidance for the preparation of prodrugs of the Tph1 inhibitors disclosed herein can be found in publications such as *Design of Prodrugs*, Bundgaard, A. Ed., Elsevier, 1985; *Design and Application of Prodrugs, A textbook of Drug Design and Development*, Krosgaard-Larsen and H. Bundgaard, Ed. 1991, Chapter 5, pages 113-91; and Bumdgaard, H., *Advanced Drug Delivery Review*, 1992, 8, pages 1-38.

Tph1 inhibitors that can be used in embodiments of the present invention also include those with the general structural formula:

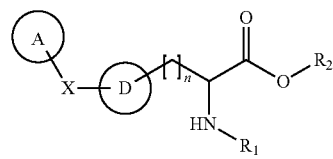

and pharmaceutically acceptable salts and solvates thereof, wherein: A is optionally substituted cycloalkyl, aryl, or heterocycle; X is a bond (i.e., A is directly bound to D), —O—, —S—, —C(O)—, —C($R_4$)=, =C($R_4$)—, —C($R_3R_4$)—, —C($R_4$)=C($R_4$)—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, -hydroxyl, or optionally substituted alkyl or aryl; each $R_5$ is independently hydrogen or optionally substituted alkyl or aryl; and n is 0-3;

and those with the general structural formula:

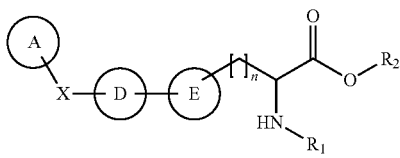

and pharmaceutically acceptable salts and solvates thereof, wherein: A is optionally substituted cycloalkyl, aryl, or heterocycle; X is a bond (i.e., A is directly bound to D), —O—, —S—, —C(O)—, —C($R_4$), —C($R_4$)—, —C($R_3R_4$)—, —C($R_4$)=C($R_4$)—, )—, —C≡C—, —N($R_5$)—, —N($R_5$)C(O)N($R_5$)—, —C($R_3R_4$)N($R_5$)—, —N($R_5$)C($R_3R_4$)—, —ONC($R_3$)—, —C($R_3$)NO—, —C($R_3R_4$)O—, —OC($R_3R_4$)—, —S($O_2$)—, —S($O_2$)N($R_5$)—, —N($R_5$)S($O_2$)—, —C($R_3R_4$)S($O_2$)—, or —S($O_2$)C($R_3R_4$)—; D is optionally substituted aryl or heterocycle; E is optionally substituted aryl or heterocycle; $R_1$ is hydrogen or optionally substituted alkyl, alkyl-aryl, alkyl-heterocycle, aryl, or heterocycle; $R_2$ is hydrogen or optionally substituted alkyl, alkyl-aryl, alkyl-heterocycle, aryl, or heterocycle; $R_3$ is hydrogen, alkoxy, amino, cyano, halogen, hydroxyl, or optionally substituted alkyl; $R_4$ is hydrogen, alkoxy, amino, cyano, halogen, hydroxyl, or optionally substituted alkyl or aryl; each $R_5$ is independently hydrogen or optionally substituted alkyl or aryl; and n is 0-3.

In the compounds disclosed in the two paragraphs immediately above:

"cycloalkyl" means a cyclic hydrocarbon having from 1 to 20 (e.g., 1 to 10 or 1 to 4) carbon atoms. Cycloalkyl moieties may be monocyclic or multicyclic, and examples include cyclopropyl, cyclobutyl, cyclopentyl, cyclohexyl, and adamantyl;

"aryl" means an aromatic ring or an aromatic or partially aromatic ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl;

"heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl;

"alkyl" means a straight chain, branched and/or cyclic ("cycloalkyl") hydrocarbon having from 1 to 20 (e.g., 1 to 10 or 1 to 4) carbon atoms. Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties;

"alkyl-aryl" means an alkyl moiety bound to an aryl moiety;

"alkyl-heteroaryl" means an alkyl moiety bound to a heteroaryl moiety; alkoxy" means an —O-alkyl group. Examples of alkoxy groups include —OCH$_3$, —OCH$_2$CH$_3$, —O(CH$_2$)$_2$CH3, —(CH$_2$)$_3$CH$_3$, —O(CH$_2$)$_4$CH$_3$, and —O(CH$_2$)$_5$CH$_3$.

Antibodies or antibody fragments that recognize and inactivate Tph1, and thus lower serum serotonin levels, can also be used in the present invention.

The terms "antibody" and "antibodies" include polyclonal antibodies, monoclonal antibodies, humanized or chimeric antibodies, single chain Fv antibody fragments, Fab fragments, and F(ab')$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful in the present invention.

Antibody fragments that have specific binding affinity for a target of interest (i.e., Tph1) can be generated by known techniques. Such antibody fragments include, but are not limited to, F(ab')$_2$ fragments that can be produced by pepsin digestion of an antibody molecule, and Fab fragments that can be generated by reducing the disulfide bridges of F(ab')$_2$ fragments. Alternatively, Fab expression libraries can be constructed. See, for example, Huse et al. (1989). Single chain Fv antibody fragments are formed by linking the heavy and light chain fragments of the Fv region via an amino acid bridge (e.g., 15 to 18 amino acids), resulting in a single chain polypeptide. Single chain Fv antibody fragments recognizing a target of interest can be produced through standard techniques, such as those disclosed in U.S. Pat. No. 4,946,778.

Once produced, antibodies or fragments thereof can be tested for recognition of the target of interest by standard immunoassay methods including, for example, enzyme-linked immunosorbent assay (ELISA) or radioimmunoassay assay (RIA). See, *Short Protocols in Molecular Biology*, eds. Ausubel et al., Green Publishing Associates and John Wiley & Sons (1992).

The amount of antibody or antibody fragment to administer will depend, inter alia, on how high the level of peripheral serotonin is compared to normal levels. Monoclonal and polyclonal anti-serotonin antibodies known in the art, or newly designed, can be used and can be administered as a single therapy or as combination therapy with Tph1 inhibitors.

Additional inhibitors of TPH1 may be identified by any methods known in the art. In particular, inhibitors of Tph1 may be identified by a method comprising:
1. providing a source of Tph1;
2. exposing the source of Tph1 to L-tryptophan in the absence of a candidate compound;
3. measuring the amount of 5-hydroxytryptophan produced by the source of Tph1 in the absence of the candidate compound;
4. exposing the source of Tph1 to L-tryptophan in the presence of the candidate compound;
5. measuring the amount of 5-hydroxytryptophan produced by the source of Tph1 in the presence of the candidate compound;
where, if the amount of 5-hydroxytryptophan produced by the source of Tph1 in the presence of the candidate compound is less than the amount of 5-hydroxytryptophan produced by the source of Tph1 in the absence of the candidate compound, the candidate compound is a Tph1 inhibitor.

Subjects Benefiting from the Inhibition of Serotonin

It has been surprisingly discovered that decreased osteoblasts cause abnormal hematopoiesis and LP-533401 reestablishes normal hematopoiesis, both in lineage and progression. Thus, any disease that is associated with abnormal hematopoietic changes and/or low osteoblast numbers would benefit from the administration of an agent that increases the growth, number and/or proliferation of osteoblasts. Also any disease which is associated with abnormal hematopoietic changes and/or low osteoblast numbers would benefit from the administration of a Tph1 inhibitor, such as LP-533401 or another agent that increases growth, number and/or proliferation of osteoblasts. These diseases would include, but are not limited to, all types of blood cancers including leukemia, lymphoma both Hodgkins and non-Hodgkins, and myeloma as well as other diseases of the blood including, but not limited to, myeloproliferative syndrome, myelodysplastic syndrome, aplastic anemia, and anemia associated with kidney disease.

In addition, because peripheral serotonin leads to decreased osteoblasts and thus abnormal bone function, subjects with primary cancers of the bone such as osteosarcoma, chrondrosarcoma, and Ewings sarcoma, as well as benign bone tumors such as osteoblastoma, osteoid osteoma, osteochondroma, enchondroma, chondromyxoid fibroma, aneurysmal bone cyst, unicameral bone cyst, and giant cell tumor (which has the potential to become malignant) would also benefit by the administration of LP-533401 or another Tph1 inhibitor or another agent that increases growth, number and/or proliferation of osteoblasts. Subjects with those bone cancers which have originated in other organs but metastasized to the bone including, but not limited to, prostate, thyroid, breast, and kidney cancers, as well as any hematological disorders affecting bone cellularity, would benefit from such therapy.

Additionally, subjects who are at risk for these diseases would also benefit from the administration of a Tph1 inhibitor, such as LP-533401, or another agent that increases the growth, number and/or proliferation of osteoblasts. Subjects who would be considered at risk for leukemia may have one or more risk factors associated with leukemia, such as smoking, or radiation exposure. Subjects who would be considered to be at risk for other blood cancers, such as Hodgkin's lymphoma, may have had exposure to viruses such as EBV, HIV, and HTLV.

Subjects who would be considered at risk for primary bone cancers may have one or more risk factors, such as exposure to high levels of radiation (like those in connection with cancer treatments), hereditary retinoblastoma, and other hereditary bone defects. Any cancer patient is at risk for metastatic bone cancer, and would benefit from administration of a Tph1 inhibitor or another agent that increases growth, number and/or proliferation of osteoblasts.

Moreover, subjects who have been found to have abnormal hematopoiesis by blood counts and/or myelograms would also benefit from the administration of a Tph1 inhibitor, more specifically LP-533401 or another agent that increases growth, number and/or proliferation of osteoblasts.

Also, subjects who have been found to have an increased level of peripheral serotonin, especially in those with any other risk factors of the various conditions would also benefit from prophylactic administration of a Tph1 inhibitor, such as LP-533401. In human subjects, serotonin levels are measured in blood and/or urine.

Pharmaceutical Compositions and Methods of Administration

The present invention encompasses the administration of inhibitors of serotonin, specifically of Tph1, and most specifically, LP-533401. Preferred methods of administration include oral; mucosal, such as nasal, sublingual, vaginal, buccal, or rectal; parenteral, such as subcutaneous, intravenous, bolus injection, intramuscular, or intraarterial; or transdermal administration to a subject. Thus, the serotonin inhibitor must be in the appropriate form for administration of choice.

Such compositions for administration may comprise a therapeutically effective amount of the serotonin inhibitor and a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

These compositions can take the form of solutions, suspensions, emulsions, tablets, pills, capsules, powders, sustained-release formulations, cachets, troches, lozenges, dispersions, suppositories, ointments, cataplasms (poultices), pastes, powders, dressings, creams, plasters, patches, aerosols, gels, liquid dosage forms suitable for parenteral administration to a patient, and sterile solids (e.g., crystalline or amorphous solids) that can be reconstituted to provide liquid dosage forms suitable for parenteral administration to a patient. Such compositions will contain a therapeutically effective amount of the compound, preferably in purified form, together with a suitable form of carrier so as to provide the form for proper administration to the patient. The formulation should suit the mode of administration.

Pharmaceutical compositions adapted for oral administration may be capsules, tablets, powders, granules, solutions, syrups, suspensions (in non-aqueous or aqueous liquids), or emulsions. Tablets or hard gelatin capsules may comprise lactose, starch or derivatives thereof, magnesium stearate, sodium saccharine, cellulose, magnesium carbonate, stearic acid or salts thereof. Soft gelatin capsules may comprise vegetable oils, waxes, fats, semi-solid, or liquid polyols. Solutions and syrups may comprise water, polyols, and sugars. An active agent intended for oral administration may be coated with or admixed with a material that delays disintegration and/or absorption of the active agent in the gastrointestinal tract. Thus, the sustained release may be achieved over many hours and if necessary, the active agent can be protected from degradation within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient over a prolonged period of time.

Pharmaceutical compositions adapted for nasal and pulmonary administration may comprise solid carriers such as powders which can be administered by rapid inhalation through the nose. Compositions for nasal administration may comprise liquid carriers, such as sprays or drops. Alternatively, inhalation directly through into the lungs may be accomplished by inhalation deeply or installation through a mouthpiece. These compositions may comprise aqueous or oil solutions of the active ingredient. Compositions for inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain anti-oxidants, buffers, baceriostats, and solutes that render the compositions substantially isotonic with the blood of the subject. Other components which may be present in such compositions include water, alcohols, polyols, glycerine, and vegetable oils. Compositions adapted for parental administration may be presented in unit-dose or multi-dose containers, such as sealed ampules and vials, and may be stored in a freeze-dried (lyophilized) condition requiring only the addition of a sterile carrier, immediately prior to use. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Selection of a therapeutically effective dose will be determined by the skilled artisan considering several factors which will be known to one of ordinary skill in the art. Such factors include the particular form of the inhibitor, and its pharmacokinetic parameters such as bioavailability, metabolism, and half-life, which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether the administration is acute or chronic, concomitant medications, and other factors well known to affect the efficacy of administered pharmaceutical agents. Thus, the precise dose should be decided according to the judgment of the person of skill in the art, and each patient's circumstances, and according to standard clinical techniques.

EXAMPLES

The present invention may be better understood by reference to the following non-limiting examples, which are presented in order to more fully illustrate the preferred embodiments of the invention. They should in no way be construed to limit the broad scope of the invention.

Example 1

Osteoblasts Secrete Factors that Suppress Leukemia Cell Numbers

To show that osteoblasts affect the leukemia cells in vitro, leukemia blasts were cultured with conditioned medium from osteoblasts.
Material and Methods
Conditioned medium (CM) was harvested after 48 hours of culture, filtered through a 0.2 μm syringe filter, and concentrated 10 times through a 3 kDa molecular weight cutoff centrifuge concentrator (Millipore). CM was diluted in fresh medium and used at a final concentration of 5 times (Christopherson et al. (2005)).
Results
As shown in FIG. 1, the leukemia cells cultured with the CM osteoblasts were suppressed in their growth. After 48 hours, there were twice as many leukemia cells cultured in the absence of CM osteoblasts than cells cultured with the osteoblasts. This result shows that factors secreted by osteoblasts inhibit the growth and proliferation of leukemia cells, in vitro.

Example 2

Creation of a Mouse Model for Leukemia

To create an in vivo mouse model for leukemia, immunocompetent syngenic mice were injected with lymphoma/lymphoblastic cells.
Materials and Methods
  Mice
  B6-albino mice, which are C57BL/6J mice that carry a mutation in the tyrosinase gene, were used for injection by the EL-4 cell line. Pigment is absent from skin, hair and eyes in the homozygotes for $Tyr^{c-2J}$ mice. B6(Cg)-Tyrc-2J mice were purchased from the Jackson Laboratory.
  BALB/cJ mice purchased from Jackson Laboratory were used for the WEHI/3B cell line.
  Cell Line
  8- to 10-week-old immunocompetent male mice were inoculated with tumor cells by tail vein injection. The EL4 cell line was established from a lymphoma-induced tumor in a C57BL mouse by 9,10-dimethyl-1,2-benzanthacene. An EL4 cell line transduced with green fluorescence protein and luciferase, EL4-GFP-Luc, was injected via the lateral tail vein of the B6(Cg)-Tyrc-2J mice (500,000 cells per mouse). The EL4-GFP-Luc fusion gene was used to allow cell trafficking and tumor progression to be assessed by an in vivo imaging system.
  WEHI/3B, a macrophage-like myelomonocytic leukemia cell line established from inbred BALB/c mice, was used. BALB/cJ mice were inoculated with $1 \times 10^6$ Wehi-3 cells.
  Imaging System
  Leukemia engraftment and progression was monitored using the Xenogen IVIS-200 System (IVIS® imaging system, Xenogen Corporation), an in vivo imaging technology platform that allows non-invasive visualization, and tracking of cellular and genetic activity within a living organism. The system consists of a CCD camera mounted on a light-tight specimen chamber, a camera controller, a cryogenic cooler, a fluorescence light source and a computer system for data acquisition and analysis. The system is capable of imaging bioilluminescence and fluorescence in living animals.
  In this study, since luminescence was being detected, luciferin as a substrate of luciferase was administered to the mice. The mice were monitored using the in vivo imaging system twice per week. Mice were anaesthetized using isoflurane, and then were injected intraperitoneally with luciferin (0.15 mg per g body weight) 10 minutes before the detection point. Mice were imaged using the in vivo system, setting the exposure time to 1 minute. Bioilluminescence intensity was recorded and counted.
  Tissue Preparation and Histopathology
  Mice were sacrificed at pre-determined time points as specified before or upon signs of illness. Each animal was weighed before blood was sampled, and visually examined for tumor development. Spleens were isolated and weighed. Spleens and tissue samples from liver were fixed in 10% neutral formalin solution for 48 hours. Osseous samples (thoracic spine, sternum, pelvis, and stifle joint) were decalcified in Decalcifier System I (Leica Microsystems, Inc.) for 48 h after fixation. All tissues were processed by routine methods and embedded in paraffin Sections of 4 or 5 μm were stained with hematoxylin and eosin (H&E) according to standard procedures.
Results
  Both cell lines engrafted into the bone marrow and liver by 7 days following injection (FIGS. 2(A), (B), (C), and (D)). Blasts were also detected in the peripheral blood (FIG.

2(E)). WEHI-3B cells also engrafted in the spleen (FIG. 2(F)). Leukemic cells were detected by bioimaging as well as by histological analysis (FIG. 2(G)). Demonstrating that osteoblasts comprise a niche for leukemia cells, engrafted leukemia blasts were detected in close contact with osteoblasts on the endosteal surface (FIG. 2(H)).

In accordance to the "Bethesda proposals for classification of lymphoid neoplasms in mice", the "simultaneous involvement of these tissues is the equivalent of bone marrow-based leukemia in humans." (Morse et al. (2002)). Thus, these mice can be used as a viable in vivo model for leukemia in humans and used to test the effects of various agents on the progression of leukemia in vivo.

Example 3

Leukemia Blasts and Bone Cells Communicate

As a first step in determining whether leukemia blasts and bone cells communicate with each other, the effect of leukemia on bone mass in murine syngeneic models of acute leukemia were investigated.
Materials and Methods
  Mice as described in Example 2 were used for analyses.
  Histomorphometry
  Histomorphometric analyses were performed on vertebral column specimens collected from 2 months old mice using undecalcified sections using the osteomeasure analysis system (Osteometrics). Lumbar vertebrae were dissected, fixed for 24 hours in 10% formalin, dehydrated in graded ethanol series, and embedded in methyl methacrylate resin according to standard protocols (Chappard et al. (1987); Parfitt et al. (1987)).
  Bone formation rate (BFR) was analyzed by the calcein double-labeling method. Calcein (Sigma) was dissolved in calcein buffer (0.15 M NaCl, 2% $NaHCO_3$) and administered by an intraperitoneal injection of 25 µg/g body weight, 6 days and 2 days before sacrificing the animals. In experiments evaluating survival rates of animals, bone formation rate was not calculated due to the unknown time of death. Unstained 4-µm sections were used for BFR measurements.
  For the analysis of parameters of osteoblast and osteoclast, 4-µm sections were stained with toluidine blue and tartrate-resistant acid phosphatase (TRAP), respectively. Type I collagen content and bone volume over trabecular volume (BV/TV) were analyzed using 7-µm sections by Von Gieson and Von Kossa staining toluidine blue, and tartrate-resistant acid phosphatase staining, respectively in undecalcified sections. Images were taken using a 10× objective on a Leica microscope outfitted with camera. Six to ten animals were analyzed for each group.
  Quantitative Real-time PCR Analysis
  Total RNA was isolated from tissues or cultured cells using Trizol, according to the manufacturer's protocol (Invitrogen). Total RNA (2 µg) was treated with DNAse I (Invitrogen), and reverse transcribed at 42° C. with SuperScript II (Invitrogen). The expression of all the genes was measured by real-time quantitative PCR with the SYBR Green Master Mix (Bio-Rad) using β actin or 18s as endogenous control.
  Biochemistry and Complete Blood Counts (CBC)
  Blood was collected by cardiac puncture in EDTA (CBCs and blood smears) or non-EDTA (serum) coated tubes. For serum preparation, blood was kept at room temperature for 15 minutes and centrifuged at 15,700 g for 10 min at 4° C. Serum osteocalcin was measured using the Osteocalcin IRMA kit (Immutopics).

Figures 3A, 3B:
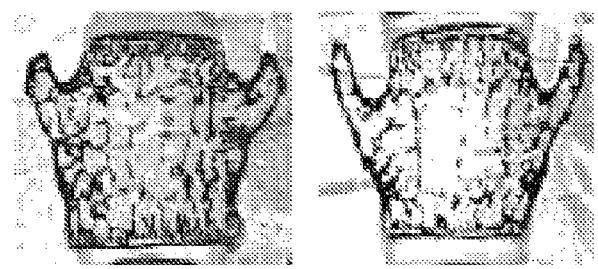
FIG. 3(A) depicts the histomorphometric bone analysis of wild-type and leukemic mice injected with WEHI-3B.
FIG. 3(B) is a table comparing the osteoblast numbers, trabecular volume, BFR and osteoclast surface per bone surface for wild-type and leukemic mice injected with WEHI-3B.
Figures 4A, 4B:
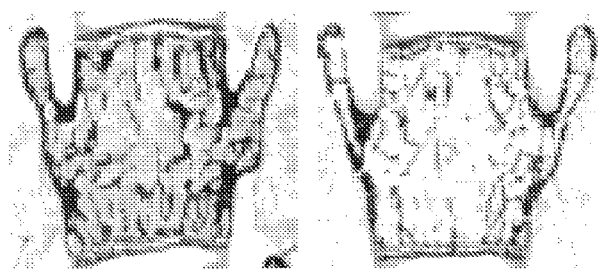
FIG. 4(A) depicts the histomorphometric bone analysis of wild-type and leukemic mice injected with EL4.
FIG. 4(B) is a table comparing the osteoblast numbers, trabecular volume, BFR and osteoclast surface per bone surface for wild-type and leukemic mice injected with EL4.
Figures 5A, 5B:
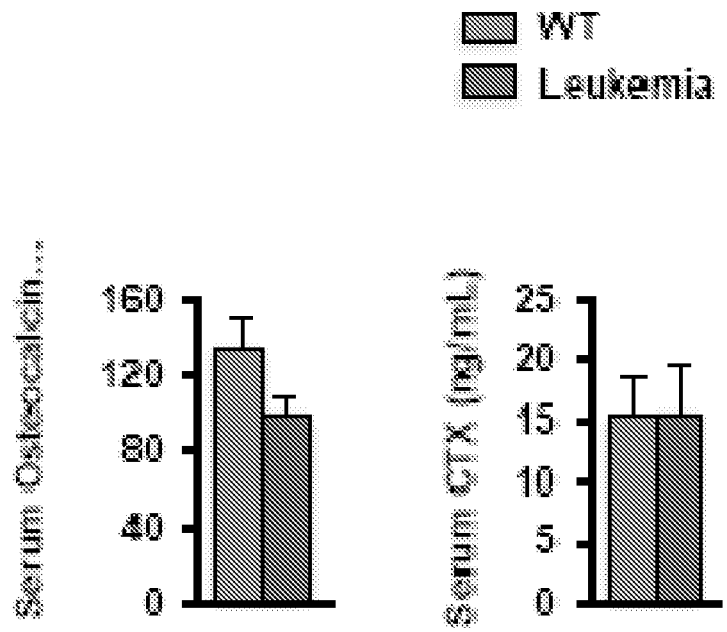
FIG. 5(A) depicts a graph of serum osteocalcin levels in leukemic and wild-type mice.
FIG. 5(B) depicts a graph of serum CTX levels in leukemic and wild-type mice.
Figure 5C:
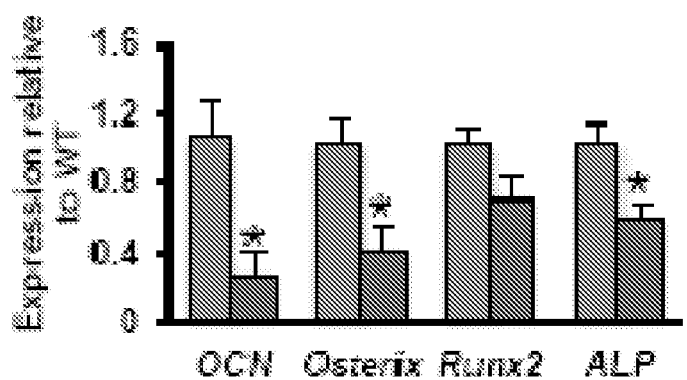
FIG. 5(C) depicts a graph of expression of osteoblast-specific formation markers, relative to wild-type, in leukemic and wild-type mice.
Figure 6:
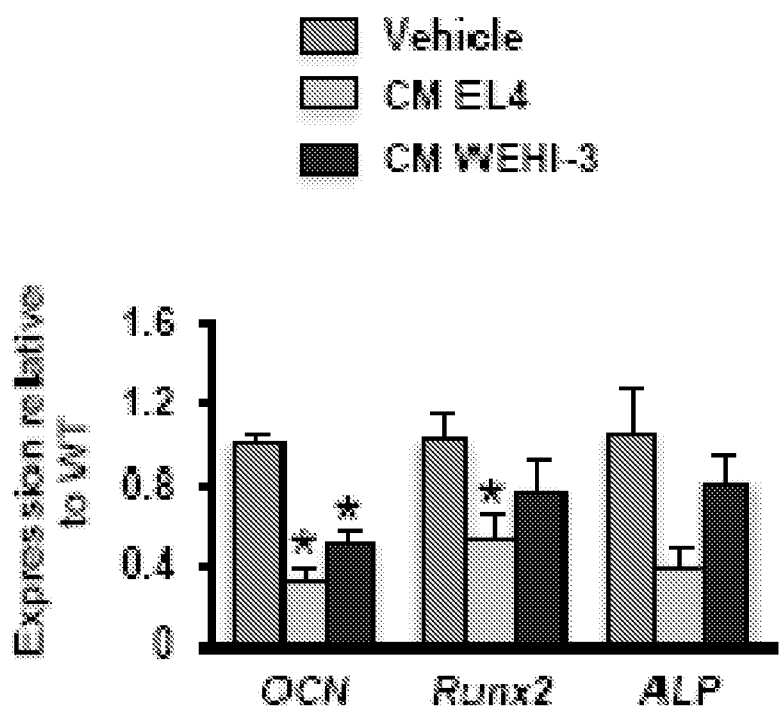
FIG. 6 shows a graph of the expression of osteoblast formation markers relative to wild-type of primary osteoblasts treated with vehicle, or CM EL4 or CM WEHI-3B.

Results
  In both models of leukemia, leukemia progression was associated with rapid, i.e, within 2 weeks, and a marked decrease in bone mass (FIGS. 3 and 4). Bone loss was due to decreased osteoblast numbers since osteoclast number and bone resorption were not affected (FIGS. 3, 4 and 5. The decrease in osteoblast numbers resulted from a decrease in their differentiation potential as evidenced by reduced expression of the osteoblast-specific formation markers osteocalcin, osterix, and Runx2 as well as alkaline phosphatase (FIG. 5(C). Serum osteocalcin levels were also decreased in leukemic mice as compared to the healthy controls, whereas serum levels of CTX, a bone resorption marker indicating osteoclast activity, were not affected (FIGS. 5(A) and (B)).
  Consistent with the in vivo observations, treatment of primary osteoblasts with conditioned medium from leukemia blasts (as described in Example 1) also suppressed their differentiation as evidenced by the decrease in the expression of osteoblast formation markers (FIG. 6).

Example 4

Creation of the DTAosb Mouse Model

Figure 7A:
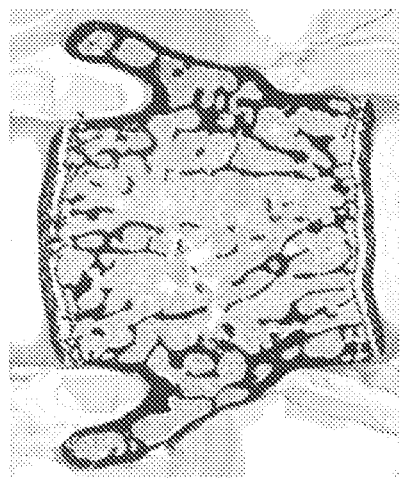
FIG. 7(A) depicts the histomorphometric bone analysis of wild-type and DTAosb mice.
Figure 7B:
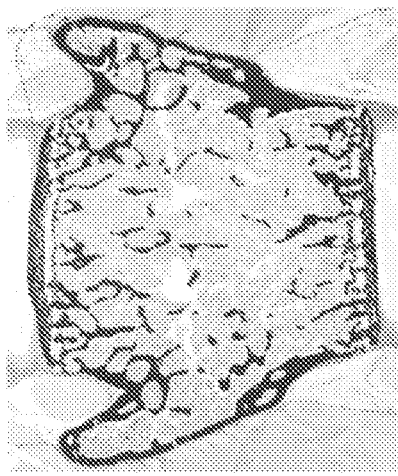
FIG. 7(B) is a table comparing the osteoblast numbers, trabecular volume and osteoclast surface per bone surface for wild-type and DTAosb mice.

In order to study the effect of osteoblast ablation on leukemia cells and leukemia progression, an in vivo mouse model lacking osteoblasts was created.
Materials and Methods
  Mice
  DTAosb mice were maintained on a C57BL/6 background. B6(Cg)-Tyrc-2J albino mice that carry a mutation in the tyrosinase gene so that pigment is absent from skin, hair and eyes in the homozygous for $Tyr^{c-2J}$ mice.
  DTAosb mice were generated by crossing $\alpha_1$(I)Collagen-Cre mice with mice in which the diphtheria toxin α subunit (DTA) has been introduced into the ubiquitously expressed ROSA26 behind a loxP-flanked STOP cassette (Yoshikawa et al. (2011)). Cre-mediated removal of the STOP cassette leads to DTA expression and cell death. In all experiments, littermates of DTA osb mice carrying the inactive form of DTA were used as wild-type control animals. Mice heterozygous for the floxed DTA allele were used in these experiments. Genotyping was performed at 3 weeks of age by PCR analysis of genomic DNA. In all experiments data presented were obtained from male animals.
  Analyses of DTAosb Versus Wild-type Mice
  Histomorphometric analyses were performed as described in Example 3.
Results
  Using the techniques set forth above and wild-type littermates as controls, DTAosb mice were created that showed a 50% reduction in osteoblast numbers, decreased trabecular volume, but no change in osteoclast surface per bone surface.
  A comparison of DTAosb mice and wild-type mice is shown in FIG. 7.
  These results show that the DTAosb mice can be used as a viable in vivo model for osteoblast deficiency.

Example 5

DTAosb Mice Injected with Leukemia Cells have a Higher Tumor Burden and More Tumor Engraftment than Wild-Type Mice In order to determine if osteoblast ablation effects leukemia progression, wild-type mice and DTAosb mice were injected with a lymphoma/lymphoblastic cells and compared using the whole-body imaging system.

Materials and Methods

The same techniques for mice, cell line and in vivo imaging from Example 2 were used.

The EL4-GFP-Luc cells were injected into both wild-type and DTAosb mice described in Example 4.

For whole-body imaging, the DTAosb mice were sacrificed by Day 17 and wild-type mice by Day 24.

Results

Using the same imaging technique used in Example 2, DTAosb mice were shown to have a higher tumor burden than the wild-type control group. This is shown both visibly in FIG. 8(B), as well as quantitatively in FIG. 8(A). Luminescence was counted from day 7 to day 17 of both wild-type and DTAosb mice. The luciferase intensity increased in the DTAosb mice dramatically at 10 days after injection with the EL4 cells (FIG. 8A). About 5 times more luminescence was detected in the bodies of the DTAosb mice, showing that they had incorporated more of the cancerous EL4 luminescent cells, i.e., leukemia cells (FIG. 8).

Example 6

Further Evidence that DTAosb Mice Injected with Leukemia Cells have a Higher Tumor Burden, and More Tumor Engraftment than Wild-Type Mice To further show that DTAosb mice have higher tumor burden and more tumor engraftment than wild-type mice, further tissue specific analyses were performed.

Materials and Methods

The same techniques for mice, and cell line from Example 2 were used. The EL4-GFP-Luc cells were injected into both wild-type and DTAosb mice described in Example 4.

For comparisons of tumor burden in bone and soft tissues, EL-4-injected groups of DTAosb and wild-type mice were sacrificed 15 days after leukemia cell injection. This is a separate experiment from the long-term, end point one shown in Example 7 where mice were observed until they died in order to measure differences in survival.

Luciferase intensity was measured by plating 4.5 million bone marrow cells into 6-well plates. Luciferin was added at a final concentration of 150 μg/mL and luciferase activity was measured at a luminometer.

Histology was performed as described in Example 2.

Results

Similar results were obtained in this experiment as in Example 5. Tumor engraftment in bone marrow only was then measured by luciferase intensity. The luciferase intensity was higher in bone marrow cells derived from mice lacking osteoblasts when compared to the controls, both visually (FIG. 9(A)) and quantitatively (FIG. 9(B)). As seen in FIG. 9(B), the luciferase activity in the bone marrow of the DTAosb mice was about 5 times that of the wild-type.

Figure 10:
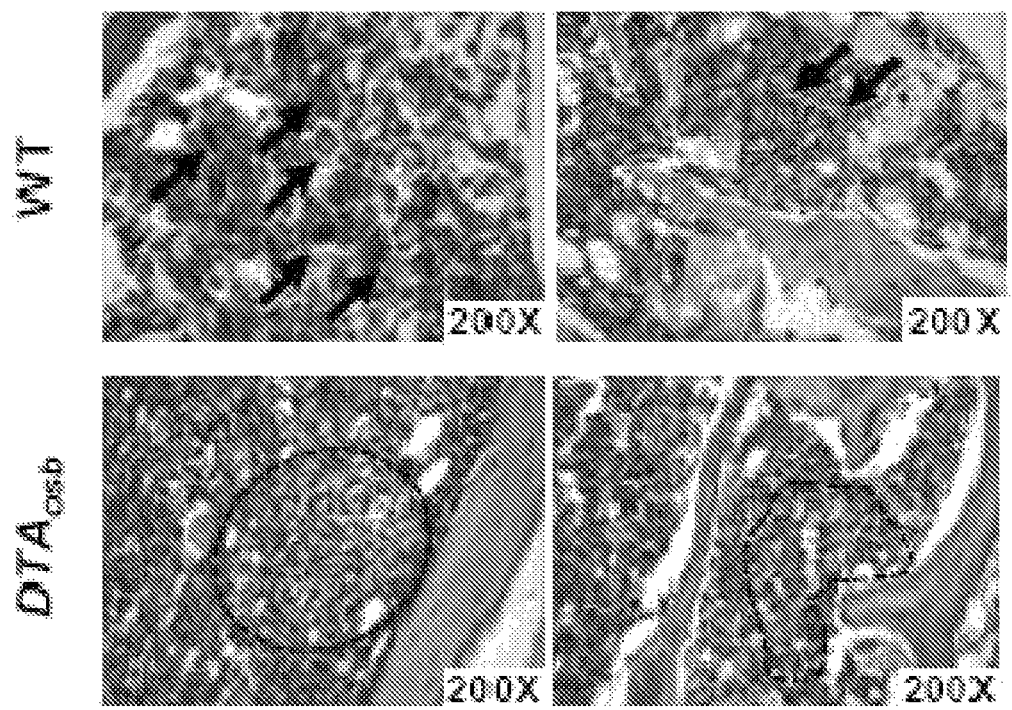
FIG. 10 is histological sections from the bone marrow of wild-type and DTAosb mice after injection with EL4-GRP-luciferase cells.

Histological sections from the DTAosb mice showed that almost all mice lacking osteoblasts had engraftment at this time point, while the majority of wild-type mice still had normal bone marrow without leukemia infiltration. The wild-type bone marrow also had evidence of trilineage hematopoiesis with megakaryocytes, erythroid and maturing myeloid cells whereas the DTAosb mice have normal marrow largely replaced by leukemic blasts (FIG. 10).

Figure 11:
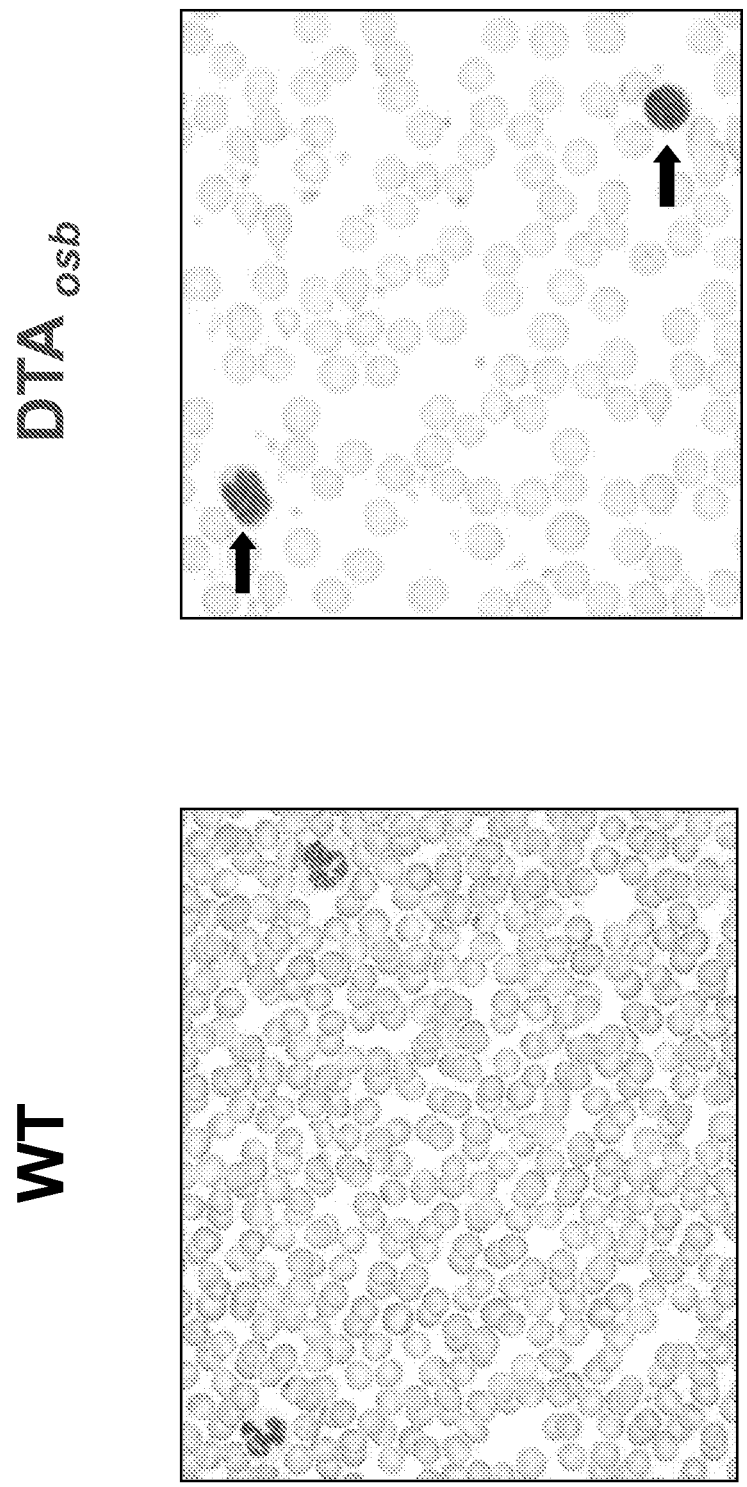
FIG. 11 is a peripheral blood smear from wild-type and DTAosb mice after injection with EL4-GRP-luciferase cells.

When peripheral blood smears were analyzed, the results were similar. Normal neutrophils were seen in the wild-type mouse. Circulating immature blasts with open chromatin, prominent nucleoli were seen in DTAosb mice (FIG. 11).

Similarly, the liver of the majority of wild-type mice at this time point appeared normal with normal hepatocytes or small focal infiltrates of blast, whereas in the DTAosb mice, there were large periportal infiltrates of blasts in all mice examined (FIG. 12). Similar results showing increased leukemia cells in DTAosb mice were obtained in the spleen and kidney.

Example 7

DTAosb Mice Injected with Leukemia Cells have Shorter Survival and Higher Incidence of Hind-Limb Paralysis than Wild-Type Mice Further evidence of increased leukemia involvement was obtained using a long-term study of hind-limb paralysis and survival.

Materials and Methods

The same techniques for mice, and cell line from Example 2 were used. The EL4-GFP-Luc cells were injected into both wild-type and DTAosb mice described in Example 4.

Hind-Limb Paralysis Analysis and Survival Analysis

Time-to-event analysis was used to assess two endpoints of interest, death and paralysis. The day which mice were inoculated with tumor cells was considered Day 1. Animals were followed up to 62 days. Mice which did not die or developed paralysis at the end of the follow-up period were right-censored. Kaplan-Meier curves were generated to illustrate time to death and paralysis, stratified by group status. Statistical significance of the between-group difference in the median time-to-endpoint was assessed by the log-rank test. Statistical analyses were performed using the EXCEL-XLSTAT and SAS softwares0. A P value less than 0.05 was considered statistically significant.

Results

Figure 13A:
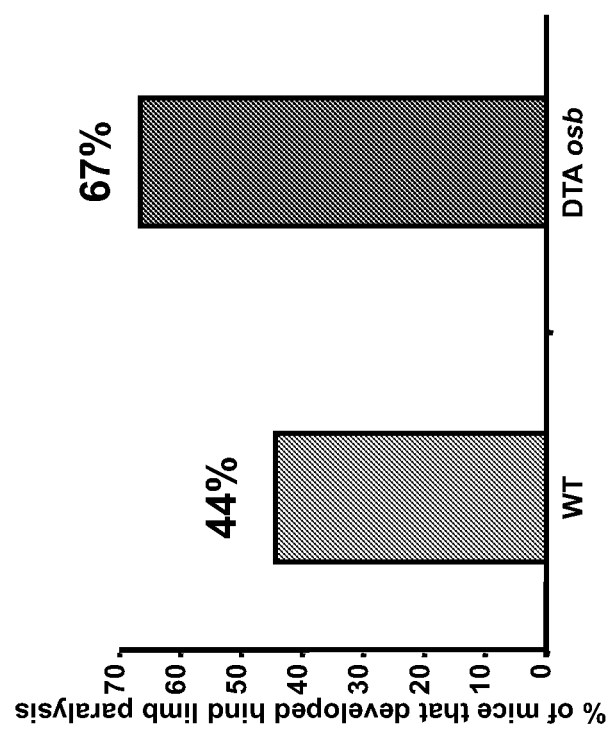
FIG. 13(A) depicts a graph showing the incidence of hind-limb paralysis in wild-type and DTAosb mice after injection with EL4-GRP-luciferase cells.

Examining further the effect of osteoblasts on leukemia progression in a long term study, it was observed in mice with osteoblast ablation, the incidence of hind-limb paralysis was higher than wild-type animals. Whereas 67% of mice lacking osteoblasts had hind-limb paralysis, only 44% wild-type littermates developed it. This observation also indicates increases in tumor burden in the bone marrow, since the hind limb paralysis is caused by the invasion of malignant cells from vertebral bodies into the spinal canal (FIG. 13).

Figure 14:
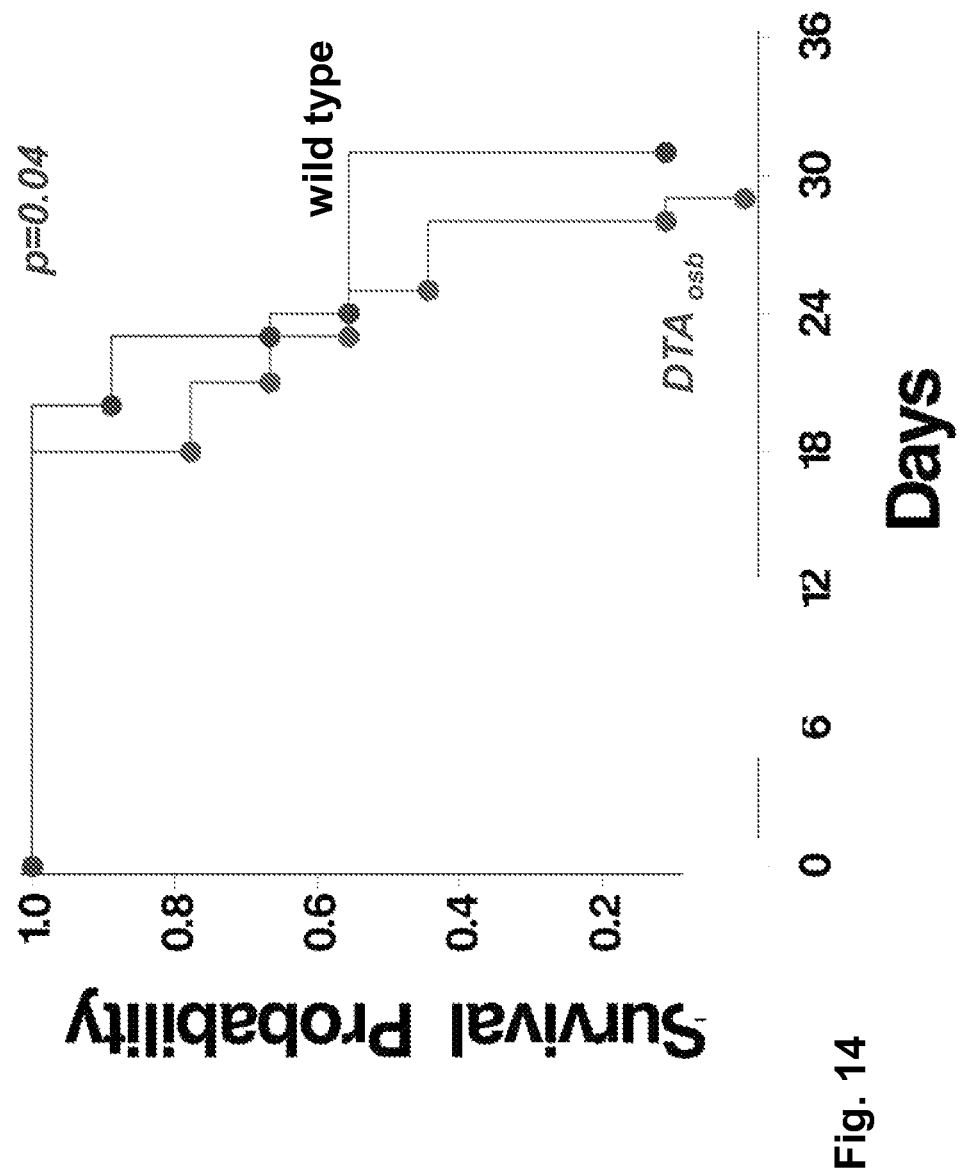
FIG. 14 depicts a graph of the survival curves of wild-type and DTAosb mice after injection with EL4-GRP-luciferase cells.

Finally, confirming that tumor burden was increased in mice with osteoblast ablation, those mice had a significantly shorter overall survival (FIG. 14).

Example 8

Osteoblast Ablation Alters Hemopoietic Lineage Determination

Since osteoblasts have been implicated in hematopoiesis and leukemia, it was investigated whether their effects on leukemia cells were direct or associated with defects in hematopoiesis by examining if partial osteoblast ablation affects hematopoietic lineages.

Materials and Methods

Using the DTAosb mice of Example 4, cells were harvested at 2 months. Cells were measured by Flow Cytometry as described below at harvest of animal.

Flow Cytometry and Cell Sorting

Freshly isolated bone marrow cells or spleen cells were resuspended in flow-staining buffer (PBS plus 2% FBS) and the primary conjugated antibodies were added. After 30 minutes incubation at 4° C., the cells were then washed twice before flow cytometry analysis. The following antibodies conjugated with fluorescein isothiocyanate (FITC), Allophycocyanin (APC) phycoerythrin (PE), PE-Cy7, APC-CY7, Pacific Blue, and Alexa 700 were used: Lineage cocktail (B220, CD19, IL-7R chain, CD3, DX5, Gr-1, Ter119, CD71 and CD41), B220 (6B2), CD19 (1D3), IgM (II/41), CD3 (KT31.1), CD4 (GK1.5), CD8 (53-6.7), Gr-1 (8C5), Mac1/CD11b (M1/70), Ter119, CD71 (C2), c-Kit (2B8), Sca-1 (E13-161-7), CD34 (RAM34), FcRII/III (2.4G2) or CD135/Flt-3 (all from Becton Dickinson, San Diego, Calif.).

The cell cycle analysis of LSK cells was determined by staining for 30 min at 37° C. with Hoechst 33342 (Molecular Probes) and pyronin Y (Sigma). Seven-color flow cytometry acquisition was performed using a LSR II flow cytometer (Becton Dickinson) and analysis using FLO-JO software (Treestar, Inc). Cells were gated for size, shape and granularity using forward and side scatter parameters. The positive populations were identified as cells that expressed specific levels of fluorescence activity above the nonspecific auto fluorescence of the isotype control. Nonspecific binding was reduced by preincubation with unconjugated anti-FcRII/III (2.4G2). For Flow sorting EL4-GFP-Luc cells were resuspended in flow staining buffer, and flow sorting was performed using FACSAria (BD). Sorted GFP positive cells were then subsequently cultured for 12 hours and injected into the mice.

Results

At 10 weeks of age DTAosb mice showed lack of any differences in bone marrow cellularity (FIG. 15(A)). In the bone marrow the hematopoietic stem and progenitor cell (HSPC) pool size, defined by Lin-Sca+c-Kit+ (LSK) cells, increased in DTAosb mice as compared to wild-type littermates (FIG. 13(B)). Specifically, the long-term repopulating LSK+CD150+CD48-HSCs (LT-HSCs) and the multipotent progenitors (MPPs, LSK+CD150-CD48+) remained unaltered whereas the LSK CD150+CD48+ short-term repopulating subset (ST-HSCs) was increased (FIG. 13(C).

Within the myeloid progenitor population (Lin-Kit+ Sca1-) the granulocyte/monocyte progenitor subset (CD34/ FcgRII/III, GMP population), the common myeloid progenitors (CMPs) and the megakaryocyte erythroid progenitors (MEPs) remained unaltered in the bone marrow of DTAosb mice (data not shown). However, the more mature myeloid cell population (CD11b+/Gr1+) increased in DTAosb mice (FIG. 15(D)). Increased myeloid activity was coupled with a reduction in B-lymphopoiesis in both mature and immature cell subsets suggesting that the hematopoietic lineage progression was altered (FIG. 15(E)). Erythropoiesis was compromised as Ter119+ erythroid progenitors in the bone marrow decreased by osteoblast depletion (FIG. 15(F)).

The lymphoid-biased multipotential progenitor population LSK+/FLT3+ showed lack of changes in DTAosb mice (FIG. 16(G)).

Consistent with these observations in the bone marrow, white blood cells (WBCs) remained unaltered, whereas the percentage of neutrophils increased and the percentage of lymphocytes decreased in the blood of DTAosb mice (FIGS. 16 (A)-(C)). Monocytes also decreased (FIG. 16(D)) despite the increase in bone marrow CD11b+/Gr1+ cells, potentially indicating a shift of the myeloid lineage towards granulocyte differentiation at the expense of monocyte differentiation. In addition, DTAosb mice did not show signs of anemia (FIGS. 16(E)-(G)).

These results indicate that osteoblast ablation alters lineage determination of HSCs by altering myeloid and lymphocytic compartments. Moreover, it leads to increased leukemia burden within the marrow cavity. The increase in myeloid populations coupled with a decrease in B-lymphopoiesis may predispose to an increase in the burden of leukemia.

Example 9

Inhibition of Gut-Derived Serotonin Suppresses Tumor Burden and Reverts Leukemia To test the hypothesis that the course of leukemia would be ameliorated in mice with an increased number of osteoblasts, a serotonin inhibitor was administered to immunocompetent syngenic mice injected with lymphoma/lymphoblastic cells in order to determine if a decrease in serotonin and an increase in osteoblasts would have an effect on leukemia.

Materials and Methods

Mice injected with the EL-4 cell line, EL4-GFP-Luc, were used as described in Example 2. The imaging system describe in Example 2 was used.

Mice were treated orally with LP-533401 (25 or 200 mg per kg of body weight per day) or vehicle. Treatments started 15 days before malignant cell injections in all sets of experiments, and continued for the indicated periods of time. LP-533401 was dissolved in polyethylene glycol (PEG) and 5% dextrose or 2.5% glucose (Sigma), and given daily by oral gavage. Mice treated with vehicle were administered, in the same way as LP533401, a solution of PEG and 5% dextrose or 2.5% glucose, daily, by oral gavage.

The mice were divided into four groups of mice:
Mice with no leukemia treated with a vehicle, i.e., non-leukemic-vehicle-treated ("WT");
Mice with no leukemia treated with LP533401, i.e., non-leukemic-LP-533401-treated ("NL-LP");
Mice with leukemia treated with a vehicle, i.e., leukemic-vehicle-treated ("Leuk-veh"); and
Mice with leukemia treated with LP-533401, leukemic-LP533410-treated ("Leuk-LP").

Treatment of the non-leukemic mice with the vehicle or LP-533401 lasted a total of 35 days and treatment of the leukemic animals with a vehicle or LP-533401 continued until the day mice were sacrificed, which occurred at different time points, depending upon the presence of signs of illness.

The various groups of mice were tested for the various parameters including serum serotonin levels, bioluminescence imaging, luciferase intensity measurement, hind-limb paralysis, blood cell counts, bone mass, osteoblast number, bone formation rate and survival.

For measurements of serum serotonin levels, mice were briefly exposed to Isoflurane (Baxter) for 30 seconds and blood was collected by cardiac puncture. Similar volumes of blood were collected from different animals for consistency in the clotting times. Serum collection from all mice was done between 9:00 am and 12:00 pm. Blood was allowed to clot on ice for 5 minutes before centrifugation at maximum speed at 4° C. for 10 minutes. The serum supernatant was removed, snap frozen and stored at −80° C. for further analysis. Serum serotonin levels were quantified by ELISA (Serotonin kit, Fitzgerald) according to manufacturer's instructions.

Bioluminescence imaging, luciferase intensity measurement, hind-limb paralysis, blood cell counts, bone mass, osteoblast number, bone formation rate and survival were determined as previously described in Examples 2, 3, and 5-7.

Results

Figures 18A, 18B:
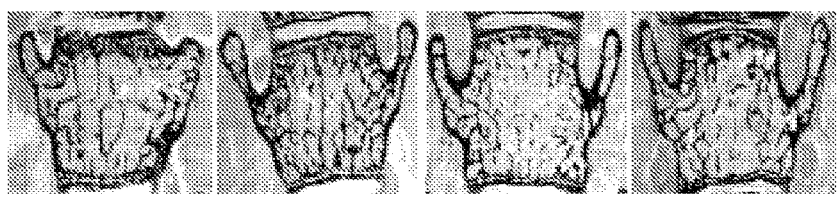
FIG. 18(A) depicts the histomorphometric bone analysis of four groups of mice: WT-vehicle; WT-LP-533401; leukemia-vehicle; and leukemia-LP-533401.
FIG. 18(B) is a table comparing the osteoblast numbers, trabecular volume, BFR and osteoclast surface per bone surface for four groups of mice: WT-vehicle; WT-LP; leukemia-vehicle; and leukemia-LP.

There was a 30% decrease in serum serotonin levels in mice treated with LP-533401 as compared to vehicle-treated animals, in both leukemic and non-leukemic groups (FIG. 17). There was also a concomitant and consequent 30% increase in bone mass due to a 30% increase in osteoblast numbers and bone formation rate (FIG. 18). In leukemic mice treated with LP-533401, inhibition of gut-derived serotonin synthesis inhibited the decrease in osteoblast numbers, bone formation rate, and trabecular bone volume (FIG. 18(B)). Bone resorption was not affected either by leukemia treatment or by serotonin inhibition.

Figure 20:
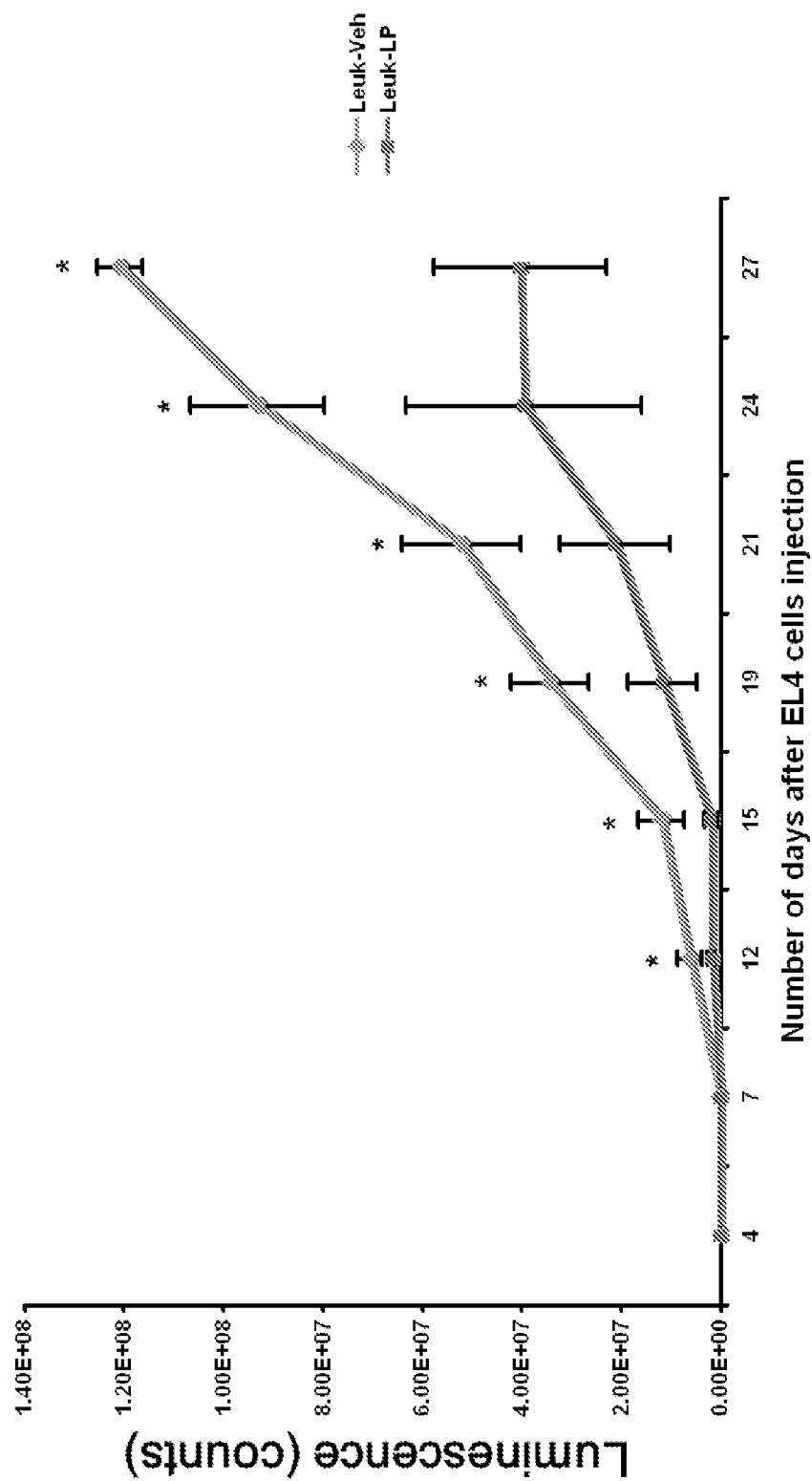
FIG. 20 depicts a graph of the luminescence counts in the vehicle-treated mice and mice treated with LP-533401 after number of days after EL4-GRP-luciferase cell injection.

Bioluminescence imaging showed decreased tumor burden in mice treated with LP-533401 (FIG. 19), which was confirmed by quantification of luciferase intensity. At day 19 after EL4 cell injection, the luciferase activity in mice treated with a vehicle has increased dramatically as compared to the LP-53340 treated mice (FIG. 20). Among ten (10) leukemic mice that were treated with LP-533401, two (2) cleared their leukemia, one (1) developed leukemia at a late stage of day 28 and then recovered, and two (2) never developed it.

Figure 21:
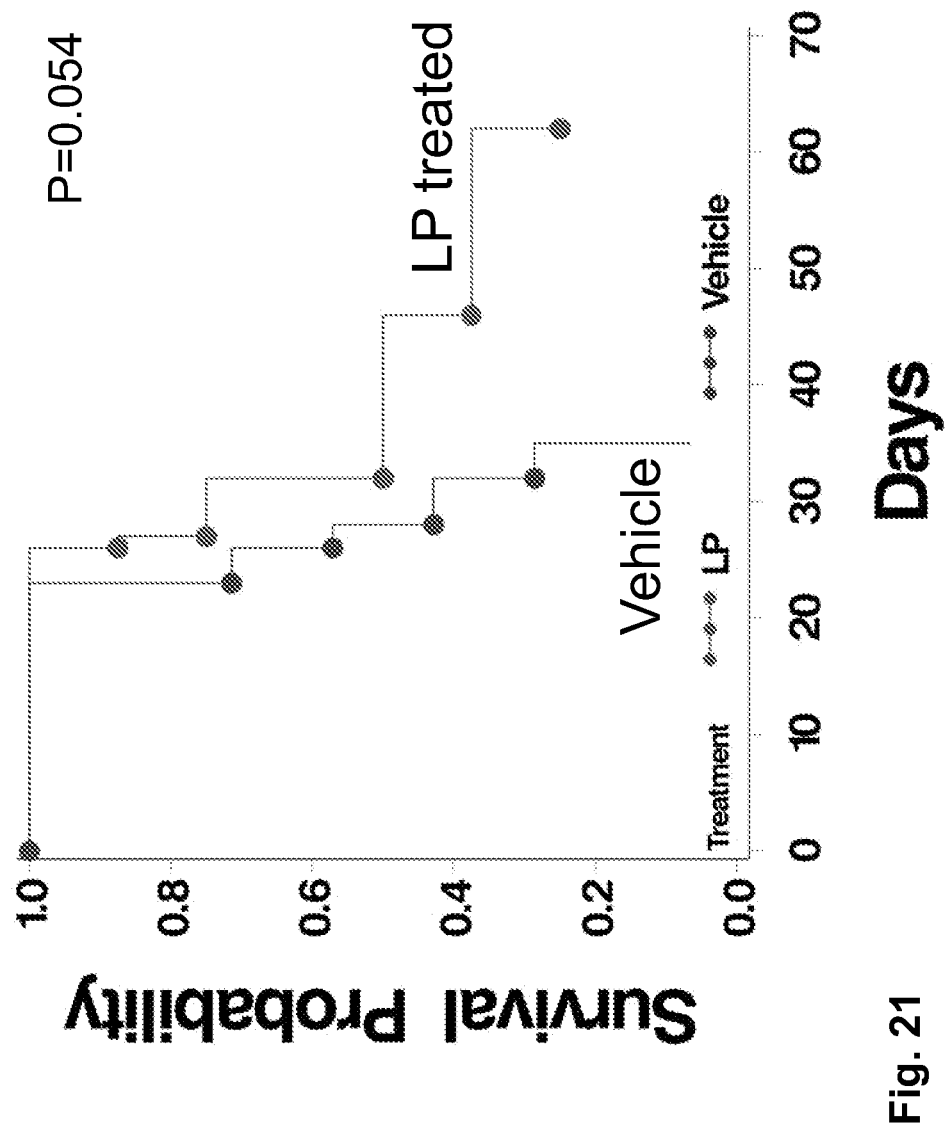
FIG. 21 depicts a graph of the survival curves of vehicle-treated mice and mice treated with LP-533401 after injection with EL4-GRP-luciferase.

LP-533401 administration resulted in a significantly longer overall survival in mice with leukemia (FIG. 21).

Figure 22:
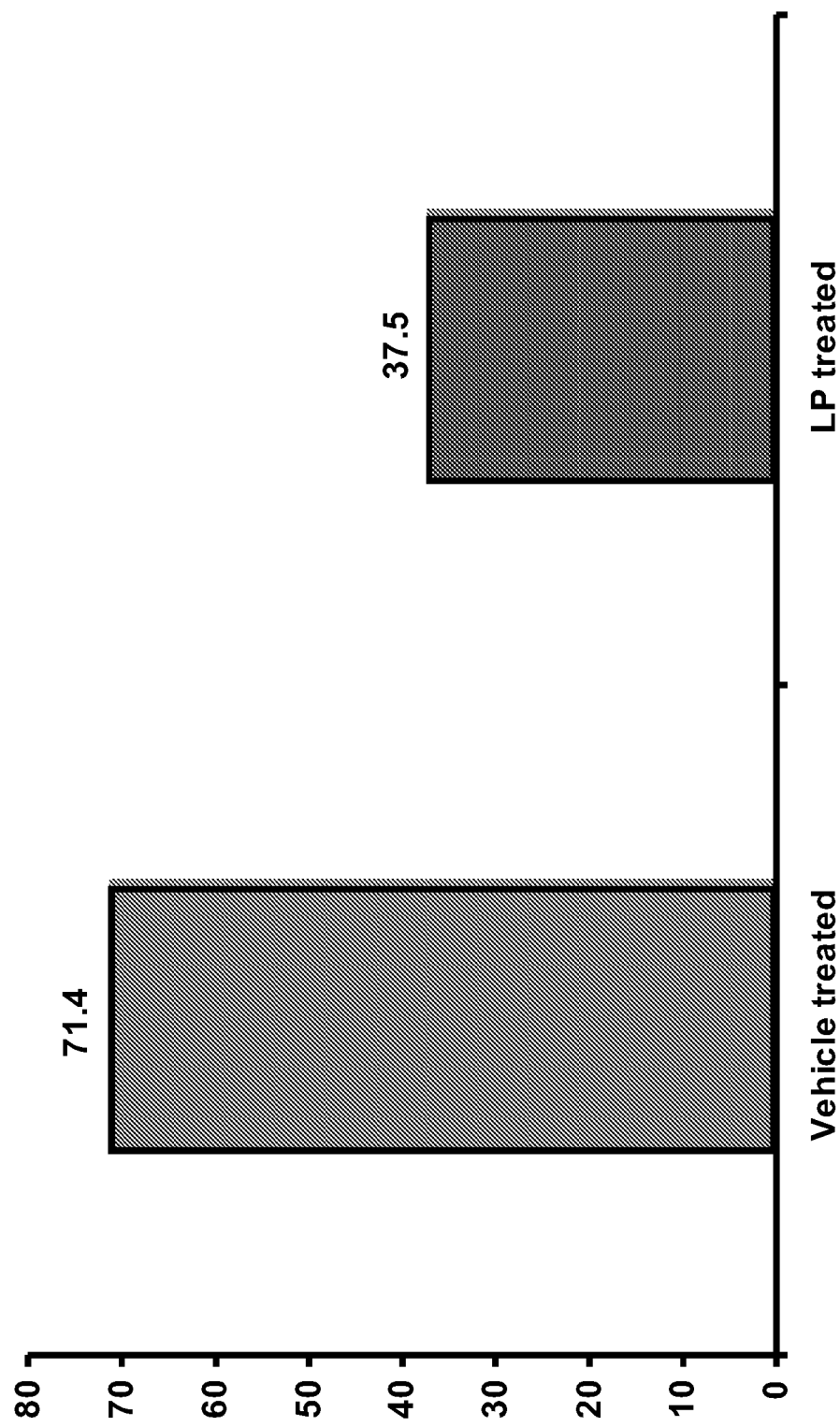
FIG. 22 depicts a graph showing the incidence of hindlimb paralysis in vehicle-treated mice and mice treated with LP-533401 after injection with EL4-GRP-luciferase cells.
Figure 23:
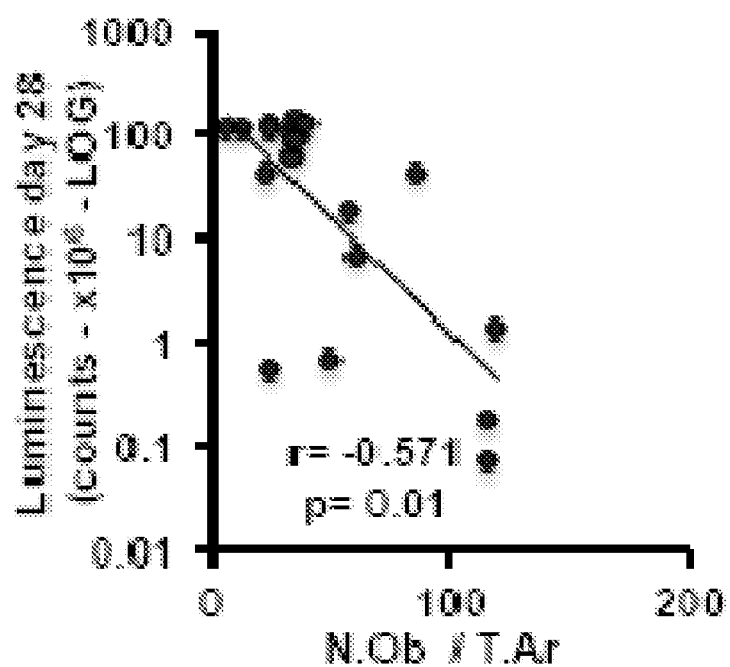
FIG. 23 is a graph correlating osteoblast numbers with tumor burden.

Moreover, 71% of vehicle-treated mice developed hindlimb paralysis, only 38% of LP-533401 treated animals developed this complication, which clearly indicates decrease in tumor burden in bone marrow in mice treated with LP-533401 (FIG. 22). Most importantly, osteoblast numbers inversely correlated with leukemia tumor burden further suggesting that inhibition of gut-derived serotonin inhibits leukemia progression by preventing the decrease in osteoblast numbers (FIG. 23).

Analysis of peripheral blood revealed that preservation of osteoblast numbers in leukemic mice treated with LP-533401 ameliorated anemia since it inhibited the decrease in red blood cells (RBCs), hemoglobin and hematocrit associated with leukemia (FIGS. 24(A), (B), (C)). The increase in WBCs, was diminished by treatment with LP-533401 (FIG. 24 (D)).

Finally, LP-533401 treatment restored to normal numbers neutrophils, monocytes and lymphocytes in leukemic mice (FIGS. 24(E), (F), and (G)). Hence, preservation of osteoblast numbers in mice with acute leukemia prevents anemia, leukocytosis and thrombocytopenia, and restores the shifts in the differentials.

Example 10

Figures 25A, 25B:
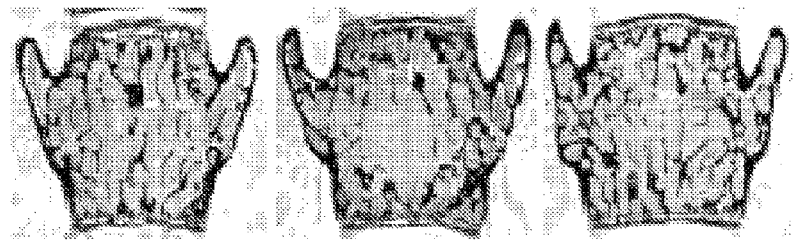
FIG. 25(A) depicts the histomorphometric bone analysis of three groups of mice: WT-vehicle; leukemia-vehicle; and leukemia-LP-533401.
FIG. 25(B) is a table comparing the osteoblast numbers, trabecular volume, BFR and osteoclast surface per bone surface for three groups of mice: WT-vehicle; leukemia-vehicle; and leukemia-LP-533401.
Figure 26A:
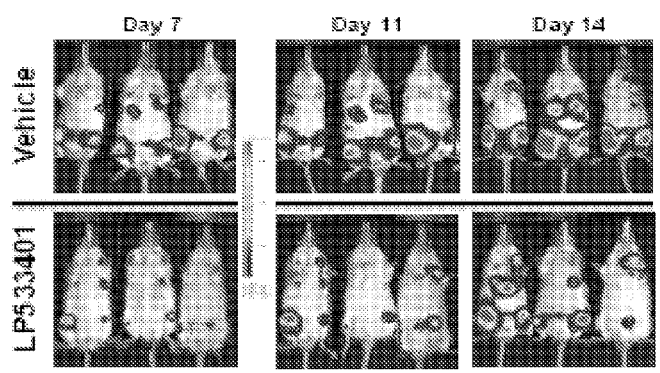
FIG. 26(A) shows cell trafficking and tumor progression of leukemic mice treated with vehicle and LP-533401 injected with EL4-GRP-luciferase cells as assessed by an in vivo image system
Figure 26B:
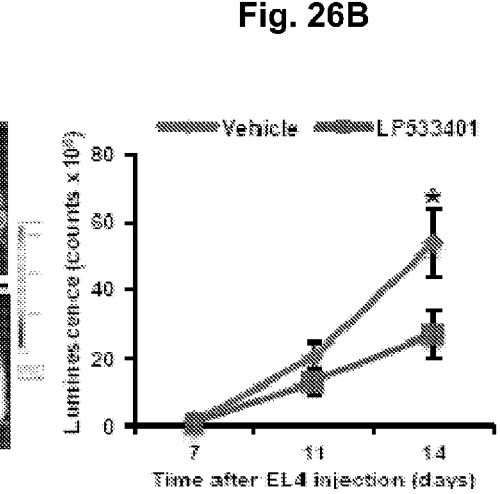
FIG. 26(B) depicts a graph of the luminescence counts of leukemic mice treated with vehicle and LP-533401 after a number of days after EL4-GRP-luciferase cell injection.
Figure 27A:
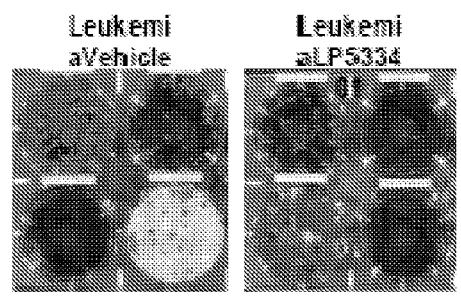
FIG. 27(A) is histological sections from the bone marrow of mice after injection with EL4-GRP-luciferase cells, some treated with vehicle and some with LP-533401.
Figure 27B:
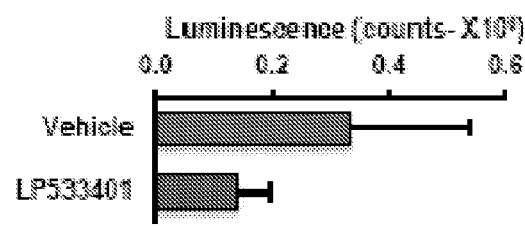
FIG. 27(B) is a graph showing the luminescence counts in the bone marrow of mice after injection with EL4-GRP-luciferase cells, some treated with vehicle and some with LP-533401.
Figure 29A:
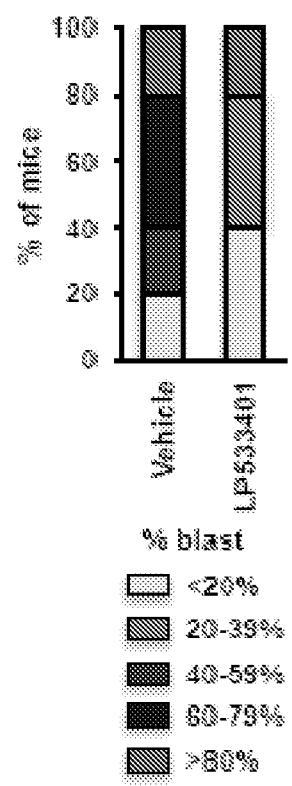
FIG. 29(A) depicts the change in percent of blasts and FIG. 29(B) megakaryocyte number.
Figure 29B:
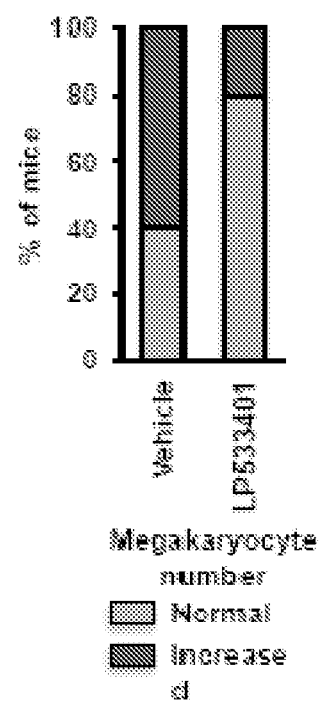
FIG. 29 A and B are graphs showing the changes of various cell types in leukemic mice, those treated with vehicle and those treated with LP-533401.

Further Evidence that Inhibition of Gut-Derived Serotonin Suppresses Tumor Burden and Reverts Leukemia To directly compare leukemia progression in mice treated with LP-5233401 and those not, a parallel group of mice were sacrificed at the same time point.
Materials and Methods The same mice and techniques used in Example 9 were used in this Example, except all of the mice were sacrificed at day 15 following EL4 cell injection
Results At this time point the decrease in bone volume, osteoblast numbers and bone formation rate caused by leukemia was ameliorated with LP-533401 treatment (FIG. 25). Neither injection with EL4 cells nor treatment with LP-533401 affected osteoclast numbers. Concomitant with the preservation of osteoblast numbers in LP-533401 treated leukemic mice, EL4 tumor burden was also decreased in whole body and in the bone marrow (FIGS. 26 and 27).

Histological analysis also indicated reduced leukemic infiltration in the marrow of LP-533401 treated leukemic mice (FIG. 28(A)). In leukemic mice treated with LP-533401 extended areas of the bone marrow remained normal whereas in untreated leukemic mice most of the marrow was heavily infiltrated with leukemia blasts. Mild myeloid hyperplasia was observed in both leukemic groups, independent of LP-533401 treatment (FIG. 29(A)). Whereas 40% of leukemic mice treated with LP-533401 had less than 20% of blasts in the bone marrow, only 20% of vehicle-treated leukemic animals presented this mild marrow infiltration (FIG. 29(A)). An additional 40% of animals from the LP-533401 treated group presented with 20 to 40% blasts in their bone marrow, as compared to 60% mice in the vehicle group, which had 40 to 80% of blasts infiltrating their marrow. The remaining 20% of mice in both groups had more than 80% blasts in the bone marrow. Megakaryocyte appearance was normal but their number increased in 60% of leukemic mice but only in 20% of LP-533401 treated leukemic animals (FIG. 29(B)). This event could be a result of deregulated hematopoiesis due to dysfunctional osteoblasts or leukemia injury. In contrast to leukemic mice, LP-533401 treated leukemic mice did not show an increase in the prevalence of immature lymphoblastic cells in the blood as compared to healthy controls suggesting clearing of leukemia from the blood (FIG. 28(B)).

In parallel, a decrease in liver leukemic involvement was also noted in leukemic mice treated with LP-533401. Whereas leukemia induced multifocal aggregates of blasts in the liver, normal or only small size focal infiltrates presented in the liver of LP-533401 treated leukemic mice (FIG. 28(C)).

Figures 30A, 30B, 30C, 30D, 30E, 30F, 30G:
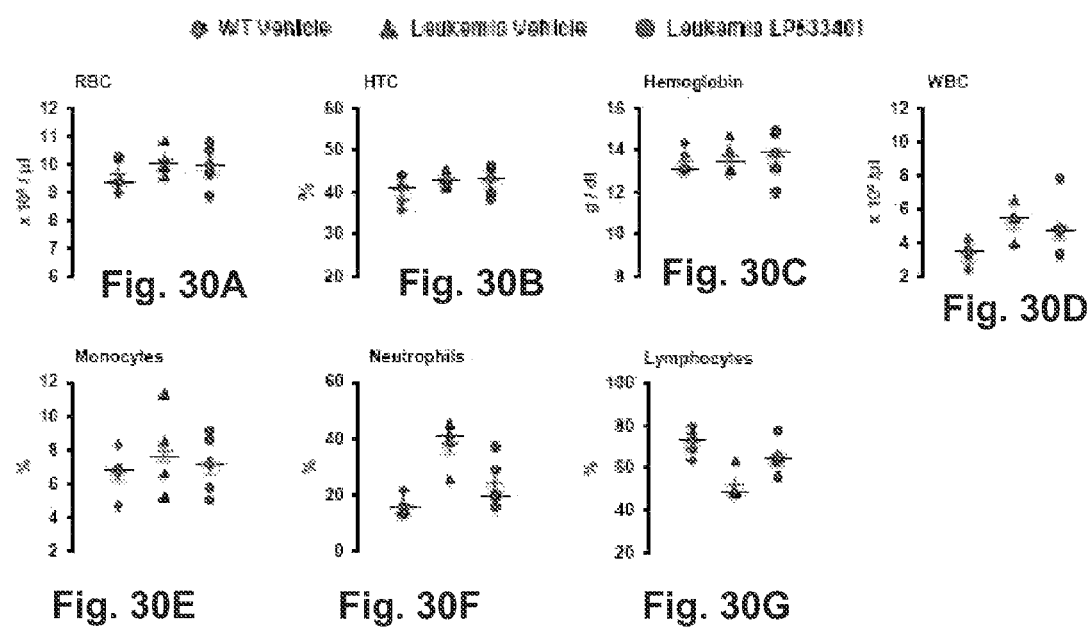
FIG. 30(A) depicts the change in red blood cells, FIG. 30(B) hematocrit, FIG. 30(C) hemoglobin, FIG. 30(D) white blood cells, FIG. 30(E) monocytes, FIG. 30(F) neutrophils, and FIG. 30(G) lymphocytes.

At this particular time point (15 days after EL4 injection), leukemia did not lead to anemia, perhaps due to the earlier stage of the disease (FIGS. 30(A), (B), and (C). However, it increased WBCs, monocytes and neutrophils and reduced lymphocyte numbers (FIGS. 30(D). (E), (F), and (G)). These changes, characteristic of lineage deregulation by leukemic cells, were all prevented in leukemic mice treated with LP-533401.

Example 11

Inhibition of Gut-Derived Serotonin has the Opposite Effect on Hematopoiesis as Osteoblast Ablation Based on the previous results demonstrating that hematopoiesis is affected in mice with partial osteoblast ablation, it was examined if non-leukemic mice treated with LP-533401 would also result in alterations in the hematopoietic compartment.
Materials and Methods The methods used in Example 8 to measure the various cell types were used.

Mice treated as described in Example 9 were examined.
Results

Figure 31A:
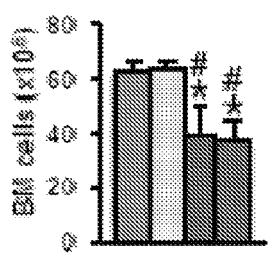
FIG. 31(A) shows bone marrow cellularity.

Treatment with LP-533401 did not affect total bone marrow cellularity (FIG. 31(A)). Leukemia reduced total bone marrow cellularity and this effect was not altered by treatment with LP-533401 (FIG. 31(A)). Non-leukemic mice treated with LP 533401 showed a decrease in LSK cells in the bone marrow compared to wild-type animals (FIG. 31(B). GMPs along with the more mature myeloid cells decreased by the LP-533401-induced increase in osteoblast number, whereas CMPS and MEPs were not affected (FIG. 31(D)). There was no effect of LP-533401 treatment in any stage of the lymphoid lineage examined, including B and T cells (FIG. 31(E); FIG. 32(C)). Ter119+ erythroid cells increased in LP-533401 treated mice (FIG. 32(D)). These changes mirrored the changes seen in DTAosb mice lacking osteoblasts and therefore confirm the effect of osteoblasts in HSC numbers and lineage differentiation populations. They indicate that osteoblast maintain LSK numbers are required for maintenance of erythroid progenitors, maintain a balance in HSC lineage determination by limiting the expansion to myeloid lineage and are required to sustain sustaining B-lymphopoiesis.

Figure 31B:
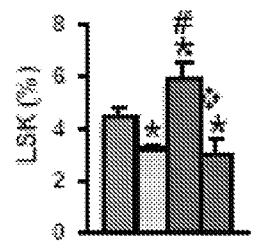
FIG. 31(B) shows percentage of LSK cells in the bone marrow.
Figure 31D:
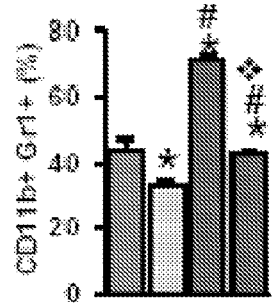
FIG. 31(D) shows percentage of CD11b+Gr1+ cells.
Figure 31C:
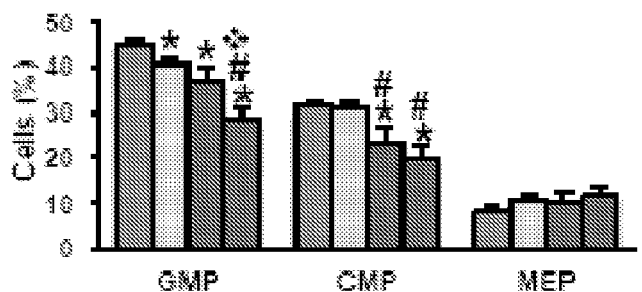
FIG. 31(C) shows percentage of GMP, CMP, and MEP cells.
Figure 31E:
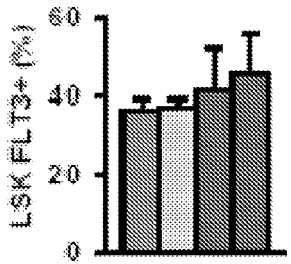
FIG. 31(E) shows percentage of LSK FLT3+ cells.

In leukemic mice, LSK cells in the bone marrow increased and this increase was hampered by treatment with LP-53340 (FIG. 31(B). The GMP and CMP populations were mildly decreased in leukemic mice; and LP-533401 further suppressed their frequencies (FIG. 31(C). MEP subsets were not affected by leukemia or LP533401 treatment (FIG. 31(C)). LP-533401 also limited the increase in CD11b+GR1+ myeloid cells observed in leukemic mice (FIG. 31(D)). The LSK FLT3+ lymphoid progenitor cell subset was not affected by leukemia or LP-533401 treatment (FIG. 31(E). However, LP-533401 treatment reduced the numbers of these cells in both healthy and leukemic mice (FIG. 32(A). Leukemia did not affect B-lymphopoiesis (FIG. 32(E)) but it reduced the numbers of B-cells in the bone marrow (FIG. 32(A)). Consistent with its lack of an effect on B-lymphopoiesis in healthy mice, LP-533401 also did not affect B-lymphopoiesis in leukemic animals. A massive increase in CD3+ cells was observed in leukemic mice (FIG. 32(C)), reflecting the fact that CD3 is a highly expressed surface marker on EL4 cells. Treatment of leukemic mice with LP-533401 prevented the increase in CD3+ cells. Similar to its effect in healthy animals, LP-533401 also increased TER119+ erythroid progenitor cells in leukemic mice (FIG. 32(D)).

Example 12

Inhibition of Gut-Derived Serotonin Decreases Tumor Burden at the Tissue Level in a Murine Model of AML The next set of experiments sought to evaluate the anti-leukemic properties of LP-533401 on tumor burden at tissue level using a murine model of AML, i.e., mice injected with a myelomonocytic leukemia cell line.

Materials and Methods

Mice

BALB/cJ mice purchased from Jackson Laboratory and injected with WEHI/3B, as described in Example 2, were used.

Mice were treated as described in Example 9 and classified as:

Mice with no leukemia treated with a vehicle, i.e., non-leukemic-vehicle-treated ("WT");
Mice with no leukemia treated with LP-533401, i.e., non-leukemic-LP-533401-treated ("NL-LP");
Mice with leukemia treated with a vehicle, i.e., leukemic-vehicle-treated ("Leuk-veh"); and
Mice with leukemia treated with LP-533401, i.e., leukemic-LP 533410-treated ("Leuk-LP").

All mice were sacrificed after 2 weeks for the following assessments:

Serum serotonin levels as measured in Example 9;
Body weight as described in Example 2
Spleen weight as described in Example 2;
Histological analysis of the femur, spleen and liver as described in Example 2;
Trabecular Bone Volume (Bv/TV) as described in Example 3;
and
Gene Expression analysis by PCR as described in Example 3.

Results

A 50% decrease in serum serotonin levels was found in NL-LP mice as compared to wild-type mice (FIG. 33(A)).

Macroscopic examination, i.e, weighing, of the spleen showed treatment with LP-533401 alleviated the enlargement of the spleens seen in leukemic mice (FIG. 33(B)).

In mice treated with vehicle, there was a decrease in body weight in leukemic as compared to non-leukemic animals. In the group treated with LP-533401, this weight loss was not observed (FIG. 32(C)).

Figure 35A:
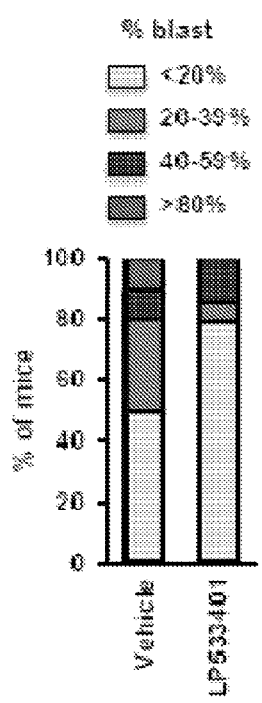
FIG. 35(A) depicts the change in percent of blasts, FIG. 35(B) myeloid:erythroid ratio and myeloid hyperplasia, and FIG. 35(C) megakaryocyte number.
Figure 35B:
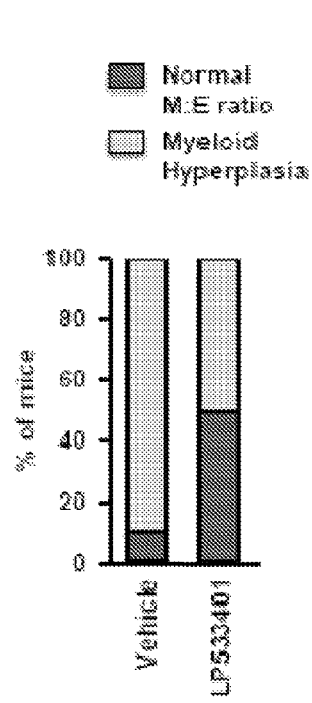
FIG. 35 A-C are graphs showing the changes of various cell types in leukemic mice, treated with vehicle and LP-533410.
Figure 35C:
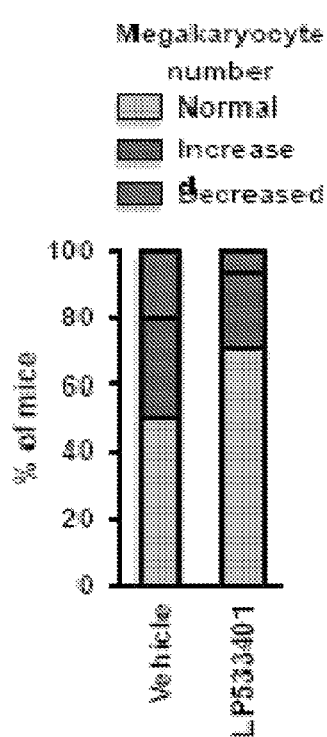

Mice treated with LP-533401 had also reduced number of leukemia blasts (FIG. 34): a blast percentage of 20% or more was seen in the bone marrow in 50% of mice treated with vehicle and in only 28% of animals treated with LP-533401 (FIG. 35(A). Among 14 mice treated with LP-533401, 10 (71%) had less than 5% marrow blasts compared to 10 mice treated with vehicle. Moreover, the myeloid:erythroid ratio was normal in 50% of the LP-533401 treated leukemic mice, whereas myeloid hyperplasia was observed in 90% of vehicle-treated animals (FIG. 35(B)). Megakaryocyte numbers also returned to normal in 70% of leukemic mice treated with LP-533401 (FIG. 35(C)).

Similar to the results with the EL4 cells in Example 9, WEHI-3B-induced leukemia outcome appeared to depend on the presence of osteoblasts since osteoblast numbers inversely correlated with the percentage of leukemic blasts in the bone marrow (FIG. 36). Similar to the suppression of leukemia burden in the bone marrow, LP-533401 treatment limited leukemia infiltration in the liver and spleen (FIG. 34). The extensive blast infiltration observed in leukemic mice was either eliminated or limited to rare periportal or focal collections of blasts (FIG. 34(B)). Moreover, splenic red pulp was normal in the LP-533401 treated leukemic mice with mature myeloid and erythroid progenitor colonies and normal megakaryocytes noted FIGS. 34 (C) and (E).

Figures 37A, 37B:
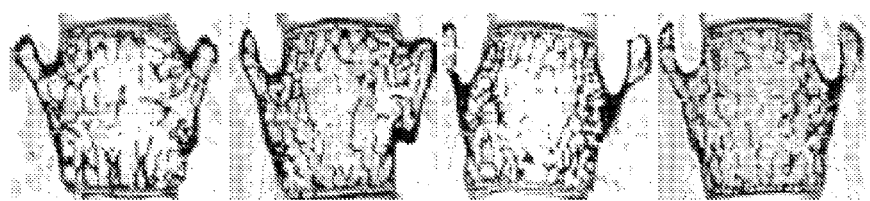
FIG. 37(A) depicts the histomorphometric bone analysis of four groups of mice: WT-vehicle; WT-LP-533401; Leukemia-vehicle; and Leukemia-LP-533401.
FIG. 37(B) is a table comparing the osteoblast numbers, trabecular volume, BFR and osteoclast surface per bone surface for four groups of mice: WT-vehicle; WT-LP-533401 Leukemia-vehicle; and Leukemia-LP-533401.
Figures 38A, 38B:
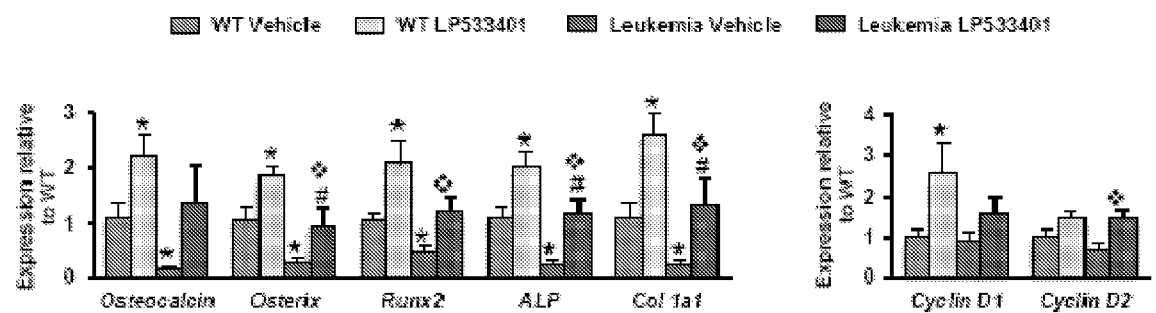
FIG. 38(A) shows osteocalcin, osterix, Runx2, ALP, and Col 1a1.
FIG. 38(B) shows cyclin D1 and cyclin D2.

The suppressive effect on leukemia in this mouse model was due to increased osteoblast numbers, and bone formation rate in LP-533401 treated leukemic mice (FIG. 37). In addition, LP-533401 prevented the decrease in trabecular bone volume, osteoblast numbers and bone formation rate caused by leukemia. As expected, osteoclast numbers were not affected either by leukemia or by treatments with LP-533401. At the molecular level the rescuing effect of LP-533401 in leukemia-induced bone loss resulted from its ability to restore normal osteoblast numbers and function. Indeed, expression of the osteoblast differentiating genes osteocalcin, osterix, Runx2, alkaline phosphatase, and collagen 1a1 was reduced in the femur of leukemic as compared to healthy mice (FIG. 38(A)). LP-533401 treatment was able to normalize the expression of the osteoblast differentiating genes in leukemic mice. In addition to inhibiting the leukemia-induced decrease in osteoblast differentiation, LP-533401 promoted the proliferation of osteoblasts in leukemic mice as shown by the increase in cyclin D1 and D2 expression in bone (FIG. 38(B)).

Figure 39B:
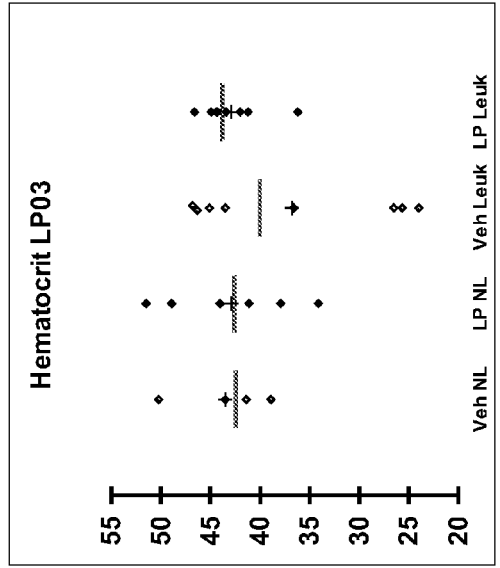
FIG. 39 A-C are graphs showing the percentage changes of various cell types in various groups of mice: vehicle-NL (wild-type); LP-NL; Veh-Leuk; and LP-Leuk.
FIG. 39(A) depicts the change in red blood cells, FIG. 39(B) hematocrit, and FIG. 39(C) hemoglobin.
Figure 39A:
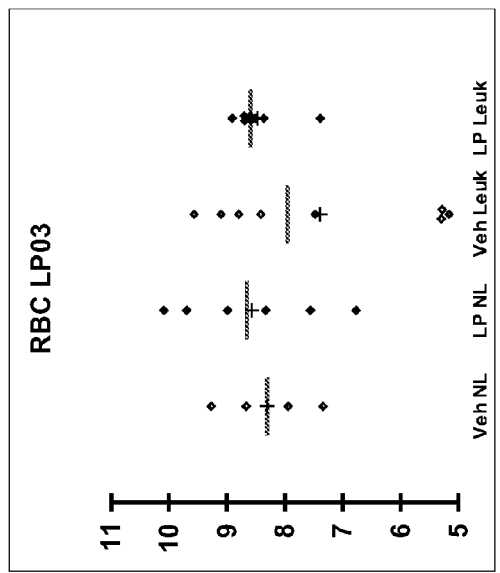
Figure 39C:
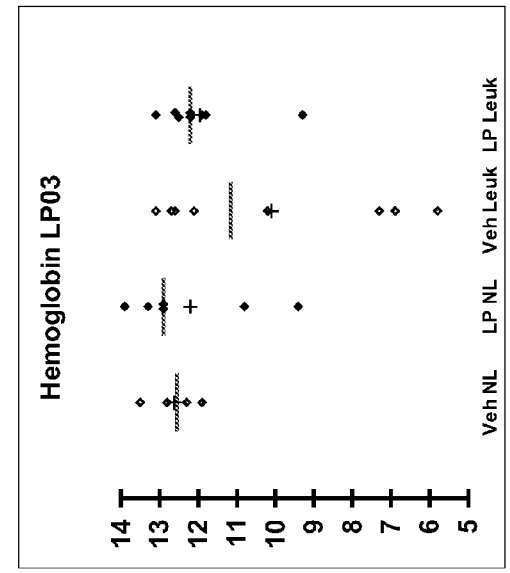

In agreement with the finding of the leukemia-limiting effect of LP-533401, the anemia observed in leukemic mice was inhibited in LP-533401-treated mice (FIG. 39).

Example 13

The Tph-1 Inhibitor LP-533401 Hinders Leukemia by Osteoblast-Specific, Leukemia Blast-Independent Actions In order to determine if the protective effects of LP-533401 in leukemia is due to its osteoanabolic actions on osteoblasts, not on action on the leukemia blasts directly.

Materials and Methods

EL4 cells and WEH-3B cells, as described in Example 2, were treated with either LP-533401 or serotonin LP-533401 treatments were performed at 0.1 to 1-fold the amount equivalent to the LP-533401 serum concentration in mice treated with this compound. Serotonin was given at concentrations ranging from 25 to 100 µM, doses at which it affects the proliferation of cells expressing serotonin receptors (Kode et al. (2012); Yadav et al. (2008) Serafeim et al. (2003)).

EL4 cells treated with LP-533401 or serotonin were then injected into syngeneic mice as described in Example 2 to monitor leukemia engraftment, as commonly described for evaluating potential direct effects of compounds on leukemia cells (Moellering et al. (2009)).

Results

Figure 40:
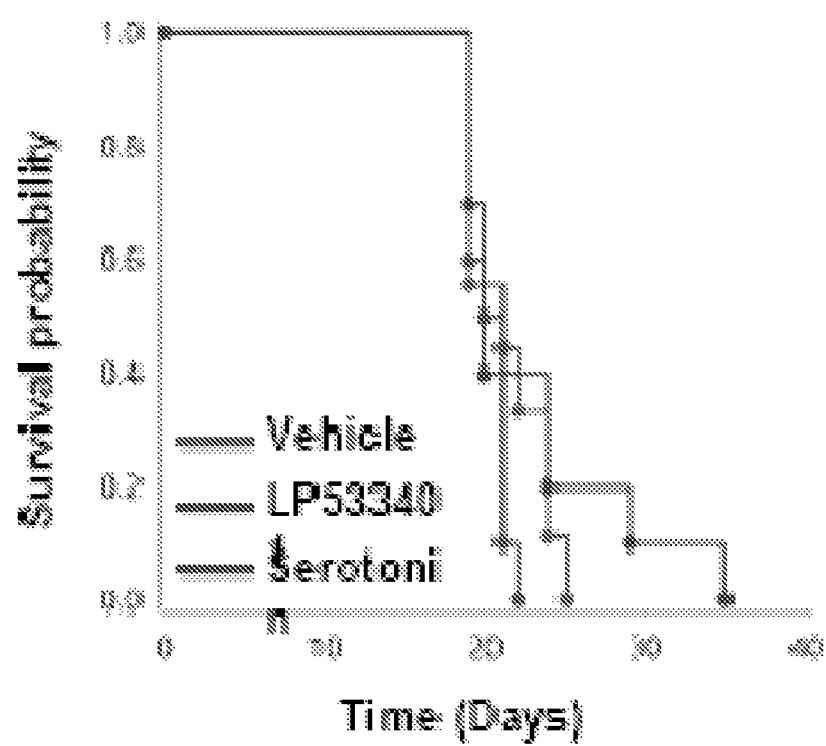
FIG. 40 depicts a graph of the survival curves of mice after injection with EL4-GRP-luciferase cells, treated with vehicle, LP-533401, or serotonin.
Figure 41A:
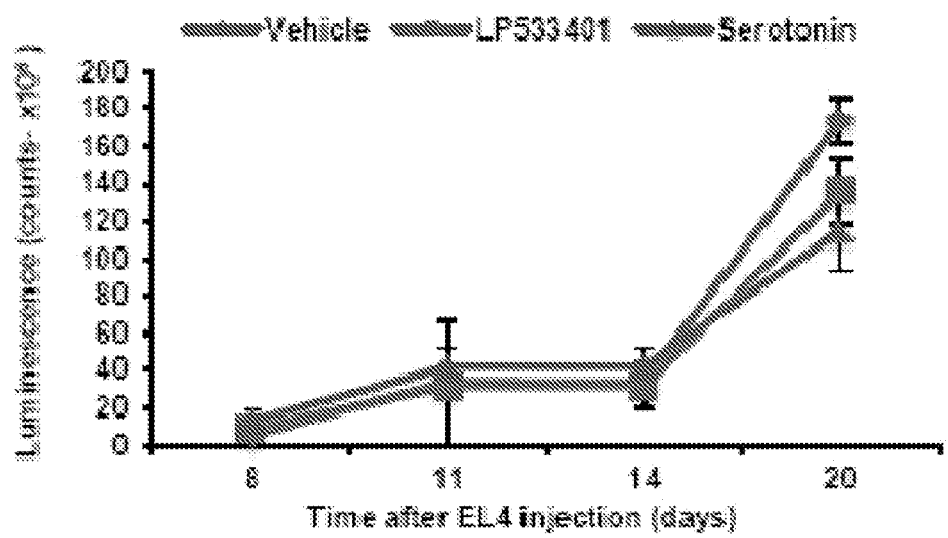
FIG. 41(A) depicts a graph of the luminescence counts in mice after injection with EL4-GRP-luciferase cells, treated with vehicle, LP-533401, or serotonin.
Figure 41B:
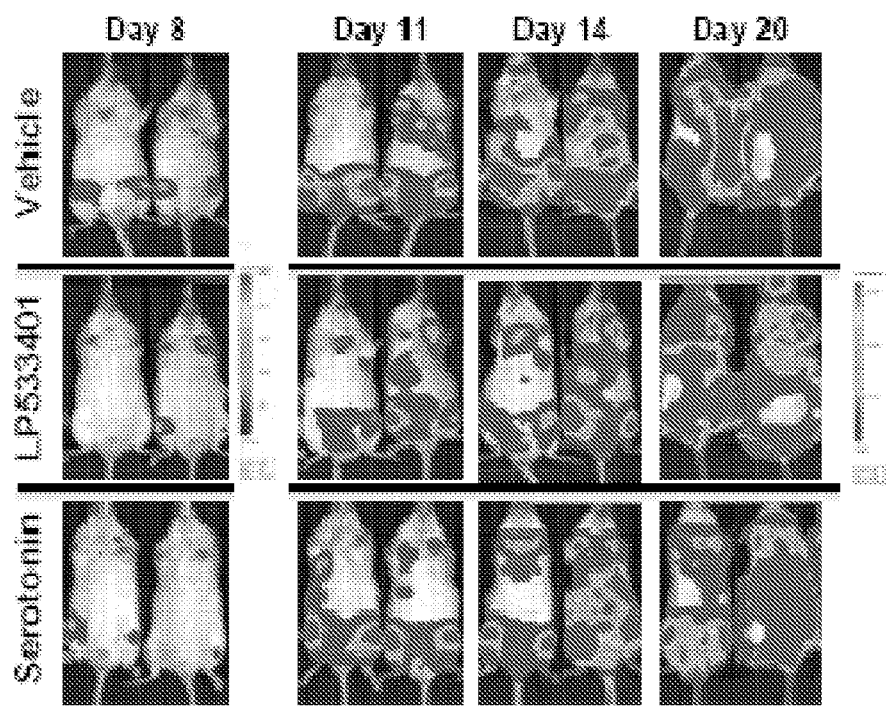
FIG. 41(B) shows cell trafficking and tumor progression of mice injected with EL4-GRP-luciferase cells, treated with vehicle, LP-533401, or serotonin as assessed by an in vivo image system

As shown in FIGS. 40 and 41, neither of the two treatments altered leukemia outcome since leukemia burden and lethality were the same in mice injected with vehicle-treated EL4 cells and LP-533401 or serotonin-treated cells.

REFERENCES

Andrews et al. (1990) *Canadian Journal of Physiology and Pharmacology* 68:325
Ausubel et al. *Short Protocols in Molecular Biology*, eds. Green Publishing Associates and John Wiley & Sons (1992).
Berger, Gray, and Roth (2009) *Annual Review of Medicine* 60:355
Bundgaard, H. (1992) *Advanced Drug Delivery Review* 8:1
Bundgard H., *Design of Prodrugs*, Elsevier, 1985;
Castillo and Jacobs (2010) *Current Osteoporosis Reports* 8:98
Calvi et al. (2003) *Nature* 425:841
Chan et al. (2009) *Nature* 457:490
Chappard et al. (1987) *Acta Histochem.* 81:183
Christopherson et al. (2005) *Cell* 120:421
Côtè et al. (2003) *Proceedings of the National Academy of Sciences*, US 100:13525
Dennis, J. E. and Charbord, P. (2002) *Stem Cells* 20: 205
Frisch et al. (2012) *Blood* 119:540
Gershon and Tuck (2007) *Gastroenterology* 132:397
Gershon (2005) *Journal of Clinical Gastroenterology* 39:S184
Gershon (2003) *Review of Gastroenterology Disorders* 3 (suppl. 2):S25
Gong, J. K. (1978) *Science* 199:1443
Huse et al. (1989) *Science* 246:1275
Inose et al. (2011) *Journal of Bone and Mineral Research* 26:2002
Iwamoto et al. (2007) *J Clin Invest.* 117:1049
Kim et al. (2008) *Blood* 112:4628
Kode et al. (2012) *J Clin. Invest* 122: 3490
Krosgaard-Larsen and H. Bundgaard, Ed. 1991, *Design and Application of Prodrugs, A textbook of Drug Design and Development Chapter 5*, pages 113-91; and
Kulke and Mayer (1999) *New England Journal of Medicine* 340:858
The Leukemia and Lymphoma Society, Facts 2010-2011
Levesque, J. P., Helwani, F. M., and Winkler, I. G. (2010) *Leukemia* 24:1979
Liu et al. (2008) *The Journal of Pharmacology and Experimental Therapeutics* 325:47
Mayack, S. R. and Wagers, A. J. (2008) *Blood* 112:519
Mendez-Ferrer et al. (2010) *Nature* 466:829
Miyamoto et al. (2011) *J Exp. Med.* 208:2175
Moellering et al. (2009) *Nature* 462:182
Morse et al. (2002) *Blood* 100246
Oh, I. H. and Kwon, K. R. (2010) *Stem Cells* 28:1243
Park et al. (2012) *Cell Stem Cell* 10:259
Patel et al. (2004) *Biological Psychiatry* 55:428
Parfitt et al. (1987) *J. Bone Miner. Res.*, 2:595
Raaijmakers et al. (2010) *Nature* 464:852
Serafeim et al. (2003) *Blood* 101: 3212
Taichman et al. (1996) *Blood* 87:518
Taichman, R. S. and Emerson, S. G. (1994) *J. Exp. Med.* 179:1677
Visnjic et al. (2004) *Blood* 103:3258
Wakley at al. (2007) *Cell* 129:097
Wu et at (2008) *Proc. Natl. Acad. Sci. U. S. A* 105:16976
Xie et al. (2005) *Bioorganic & Medicinal Chemistry Letters* 15:3267
Yadav et al. (2010) *Nature Medicine* 16:308
Yadav et al. (2008) *Cell* 135:825
Yoshikawa et al. (2011) *J Bone Miner. Res.* 26:2012
Zhang et al. (2003) *Nature* 425:836
Zhu et al. (2007) *Blood* 109:3706

The invention claimed is:

1. A method of treating or preventing leukemia comprising administering to a subject in need thereof a therapeutically effective amount of LP-533401.

2. A method of treating or preventing cancer of the blood or bone comprising administering to a subject in need thereof a therapeutically effective amount of LP-533401.

3. A method of treating or preventing a disorder or disease of the blood comprising administering to a subject in need thereof a therapeutically effective amount of LP-533401.

4. A method of treating or preventing irregular hematopoiesis comprising administering to a subject in need thereof a therapeutically effective amount of LP-533401.

5. The method of claim 1, wherein the subject is a mammal.

6. The method of claim 1, wherein the subject in human.

7. The method of claim 2, wherein the subject is a mammal.

8. The method of claim 2, wherein the subject in human.

9. The method of claim 3, wherein the subject is a mammal.

10. The method of claim 3, wherein the subject in human.

11. The method of claim 4, wherein the subject is a mammal.

12. The method of claim 4, wherein the subject in human.

* * * * *